(12) United States Patent
Jaques et al.

(10) Patent No.: US 11,371,002 B2
(45) Date of Patent: Jun. 28, 2022

(54) SINGLE USE BIOREACTOR

(71) Applicant: Lonza Ltd, Visp (CH)

(72) Inventors: Colin Mark Jaques, Slough (GB);
Mohsan Waseem Khan, Slough (GB);
Rita D'Ornelas P. De Barros Costa,
Slough (GB); Anthony Beaney, Slough
(GB); David Valentine, Slough (GB)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 17/019,516

(22) Filed: Sep. 14, 2020

(65) Prior Publication Data

US 2021/0002597 A1    Jan. 7, 2021

Related U.S. Application Data

(63) Continuation of application No. 15/613,954, filed on Jun. 5, 2017, now Pat. No. 10,801,003.
(Continued)

(51) Int. Cl.
*C12M 1/00*    (2006.01)
*C12M 1/06*    (2006.01)
(Continued)

(52) U.S. Cl.
CPC ........... *C12M 23/28* (2013.01); *B01F 23/231* (2022.01); *B01F 27/053* (2022.01);
(Continued)

(58) Field of Classification Search
CPC ...... C12M 23/14; C12M 23/26; C12M 23/28; B01F 7/00033
See application file for complete search history.

(56) References Cited

U.S. PATENT DOCUMENTS 5,656,491 A    8/1997   Cassani et al.
7,629,167 B2  12/2009   Hodge et al.
(Continued)

FOREIGN PATENT DOCUMENTS

DE    202007005868    7/2007
JP    S5035529        4/1975
(Continued)

OTHER PUBLICATIONS

PCT/EP2017/063631 International Search Report and Written Opinion dated Nov. 15, 2017.

*Primary Examiner* — Jonathan M Hurst
(74) *Attorney, Agent, or Firm* — Dority & Manning, P.A.

(57) ABSTRACT

A single-use bioreactor is provided. The single-use bioreactor may include a bioprocess container, a shell, at least one agitator, at least one sparger, at least one gas filter inlet port for the sparger(s) and headspace overlay, at least one fill port, at least one harvest port, at least one sample port, and at least one probe. In examples, at least one controller may monitor and control one or more parameters associated with the single-use bioreactor A method to cultivate and propagate mammalian cells is also provided. The method may include cultivating under suitable conditions and in a suitable culture medium in a first single-use bioreactor, transferring the medium containing the cells obtained by propagation from the at least one mammalian cell is into a second single-use bioreactor, transferring the medium containing the cells obtained by propagation from the at least one mammalian cell is into a third single-use bioreactor, and cultivating the cells in the third bioreactor.

21 Claims, 37 Drawing Sheets

Related U.S. Application Data

(60) Provisional application No. 62/345,381, filed on Jun. 3, 2016.

(51) Int. Cl.
  B01F 23/231 (2022.01)
  B01F 27/053 (2022.01)
  B01F 27/86 (2022.01)
  B01F 27/191 (2022.01)
  B01F 27/113 (2022.01)
  B01F 35/513 (2022.01)

(52) U.S. Cl.
  CPC ........ B01F 27/1134 (2022.01); B01F 27/191 (2022.01); B01F 27/86 (2022.01); B01F 35/513 (2022.01); C12M 23/14 (2013.01); C12M 23/26 (2013.01); C12M 27/02 (2013.01); C12M 27/20 (2013.01); C12M 29/00 (2013.01); C12M 29/06 (2013.01); B01F 2215/0431 (2013.01); B01F 2215/0459 (2013.01)

(56) References Cited

U.S. PATENT DOCUMENTS

| | | |
|---|---|---|
| 7,897,379 B2 | 3/2011 | Kenney et al. |
| 8,177,082 B2 | 5/2012 | Cattadoris et al. |
| 8,178,345 B2 | 5/2012 | Bennett et al. |
| 8,216,828 B2 | 7/2012 | Cattadoris et al. |
| 8,298,054 B2 | 10/2012 | Hodge et al. |
| 8,870,443 B2 | 10/2014 | Greller et al. |
| 9,045,721 B2 | 6/2015 | Martin et al. |
| 9,388,373 B2 | 7/2016 | Rao et al. |
| 9,540,606 B2 | 1/2017 | Kunas et al. |
| 9,880,067 B2 | 1/2018 | Isailovic |
| 9,926,522 B2 | 3/2018 | Totani et al. |
| 2005/0239198 A1 | 10/2005 | Kunas et al. |
| 2005/0239199 A1 | 10/2005 | Kunas et al. |
| 2007/0172945 A1* | 7/2007 | O'Kennedy ........... C12M 23/14 435/325 |
| 2008/0118974 A1 | 5/2008 | Martin et al. |
| 2009/0305626 A1 | 12/2009 | Hope |
| 2010/0015696 A1* | 1/2010 | Claes ..................... C12M 23/26 435/303.3 |
| 2010/0216229 A1 | 8/2010 | Kenney et al. |
| 2011/0013474 A1* | 1/2011 | Ludwig .................... B01F 7/22 366/102 |
| 2011/0280797 A1 | 11/2011 | Mohtadi ie tla |
| 2011/0312087 A1* | 12/2011 | Khan ..................... C12M 27/02 435/325 |
| 2012/0077429 A1 | 3/2012 | Wernimont et al. |
| 2013/0101982 A1* | 4/2013 | Goodwin ............... C12M 23/26 435/3 |
| 2013/0280797 A1 | 10/2013 | Rao et al. |
| 2014/0087465 A1 | 3/2014 | Yoshikawa et al. |
| 2015/0037882 A1 | 2/2015 | Rowley et al. |
| 2015/0117142 A1 | 4/2015 | Staheli et al. |
| 2015/0125930 A1 | 5/2015 | Gebauer et al. |
| 2015/0258513 A1 | 9/2015 | Morrissey et al. |
| 2016/0097074 A1 | 4/2016 | Collins et al. |
| 2016/0194591 A1* | 7/2016 | Castan ..................... C12N 1/20 435/348 |
| 2017/0107476 A1 | 4/2017 | Polley et al. |
| 2017/0259231 A1 | 9/2017 | Zahnow et al. |
| 2017/0266632 A1 | 9/2017 | Matttson et al. |
| 2018/0010082 A1 | 1/2018 | Jaques et al. |

FOREIGN PATENT DOCUMENTS

| | | |
|---|---|---|
| JP | S5712992 | 1/1982 |
| JP | S61160698 | 10/1986 |
| JP | 2012044943 | 3/2012 |
| JP | 2012135318 | 7/2012 |
| JP | 2014121302 | 7/2014 |
| JP | 2015503361 | 2/2015 |
| WO | WO8601531 | 3/1986 |
| WO | WO2017072201 | 5/2017 |

\* cited by examiner

SINGLE USE BIOREACTOR

CROSS REFERENCE TO RELATED APPLICATIONS

This application is a continuation of U.S. patent application Ser. No. 15/613,954 filed in the United States Patent and Trademark Office having a filing date of Jun. 5, 2017, which claims priority to U.S. Provisional Application No. 62/345,381, filed on Jun. 3, 2016, the contents of which are incorporated herein by reference. U.S. Provisional Application No. 62/354,216, filed Jun. 24, 2016, and the following publications U.S. Patent Publication No. 2011/0312087, U.S. Patent Publication No. 2017/0107476, WO Publication No. WO 2017/072201, are each hereby incorporated by reference in their entirety.

BACKGROUND ART

Bioreactors, or apparatuses in which biological reactions or processes can be carried out on a laboratory or industrial scale, are used widely within the biopharmaceutical industry. Bioreactors can be used in fed-batch applications, wherein substrates are supplied at certain times to a bioreactor and wherein products remain in the bioreactor until the end of the reaction time, or in perfusion applications, wherein a continuous supply of substrate is supplied to the bioreactor while damaging by-products are continuously removed. Bioreactors can also be used in continuous batch applications, Since the late 1990's there has been increasing interest in single use bioprocessing solutions within the biopharmaceutical industry. These solutions reduce the capital costs and validation time for new facilities, improve plant throughput by reducing turnaround time between batches, and reduce the burden of cleaning validation.

This interest in single use bioprocessing solutions has included the bioreactor unit operation. As a result, single use bioreactors (SUBs) are becoming standard work horses in the biopharmaceutical industry. These SUBs are supplied by vendors as off the shelf designs, limiting the cell culture engineer's ability to match the geometry of the SUB to the geometry of their existing stirred tank reactor (STR) capacity. For example, the first generation of SUBs departed from conventional stirred tank bioreactor (STR) geometry in terms of impeller number and orientation and sparger hole diameter. Moreover, one marked feature of single use bioreactors SUB bioreactors was that they could be operated at lower volumes than conventional STRs, bringing considerable operational flexibility. This practice, however, further negated the principle of geometric similarity.

The availability of single use bioreactors designed to facilitate universal use in development, in manufacturing operations, and in commercialization of biologics through the cultivation of cells, such as eukaryotic (mammalian) cells, is limited by the state of art. These limitations stem, in part, from: (i) lack of scalability to large scale operations up to 20,000 L, such as up to 100,000 L; (ii) lack of scalability to a small scale (~10 mL or even ~1 mL) development model to permit process development and process characterization in a meaningful manner where the small-scale data produced shows similar and comparable performance to that observed at manufacturing scale; (iii) inadequate mixing and aeration due to the vessel selection and agitator design parameters; and (iv) inadequate design of addition ports to permit application of feeds that are bolus, small volume, concentrated and typically non-physiological in pH and osmolality and/or continuously applied feeds or perfusate/retentate at flow rate ranging from 0.1% v/v per hour to 12.5% v/v per hour.

The current state of the art has additional limitations, such as (i) inadequate design of harvest ports to permit high flow rate without collapsing the harvest tube under the suction head of a pump; (ii) inability to demonstrate process comparability with existing validated bioreactors; (iii) introduction of biologically-active components from the material of contact; and (iv) the sequestering of biologically active medium components or cell-derived metabolites onto the vessel surface, which can result in those components and metabolites becoming limiting or unavailable to the cell present in the bulk aqueous phase.

The current state of art for single use bioreactors is limited to a vessel working volume of from 10 L and up to 2,000 L. The lack of availability of suitable small scale (such as less 10 mL) development models limits the ability of the cell engineer to perform meaningful process development and process characterization experiments to support manufacturing and commercialization of cell culture processes. Meanwhile, the lack of availability of disposable bioreactors greater than 2,000 L prevents the ability to benefit from the cost of goods reduction that can result from scaling up to beyond 2,000 L.

Moreover, below the 50 L scale, the disposable vessels are constructed of different materials, typically rigid polycarbonate-based plastics, than those used in vessels designed for a greater than 50 L scale, which tend to be constructed from flexible low-density polyethylene-based plastics. These materials of construction have different extractable/leachable profiles of components; these different profiles which may affect the growth, metabolism, or synthesis of proteins by the cells in different ways. The hydrophobicity of these materials of construction is also different, as is their ability to adsorb hydrophobic components present within the medium. As such, based on the material of construction used in the bioreactor vessel, the feeding and/or the production of actively-growing cells on the material surface are potentially different.

Current disposable bioreactor designs rely on principles for mixing and aeration characteristics which are unproven beyond the narrow scale described in the state of art. The disposable vessel mixing principles described in the state of art include (i) orbital shaking or rocking to create surface ripples, which permits mixing of the surface layer with the liquid bulk; (ii) an acentrically positioned impeller on an impeller shaft or an impeller mounted off-center on conical shaped vessel bottom which permits axial mixing by vortexing of fluid around the impeller zone; (iii) centrally mounted impeller(s) in an unbaffled vessel with a complex base/base plate design to permit axial deflection of radial flowing liquid bulk; and (iv) non-circular vessel (cube) stirred vessels to overcome the lack of axial flow due to lack of baffles.

With regard to bioreactor designs utilizing orbital shaking or rocking, the effectiveness of surface aeration and mixing is limited by a decrease in the surface area as compared to volume as the scale increases; as such, the use of such design can be limited to bioreactors scaled to less than 500 L. For scales of operation of 2000 L and beyond, the hydrodynamic forces needed to create energetic ripples that could penetrate the liquid surface and transfer the mass and energy deep into the liquid bulk would require considerable mechanical strength in the steel holding vessel, disposable bioprocess container, motor and the gearing needed to move the bioprocess container in an orbital motion or tilt it beyond the horizontal plane.

With regard to acentrically positioned impellers, a single impeller mounted off-center offers some advantage in allowing a contiguous change in operating volume during a fed-batch process without having to consider the impact of the liquid surface being cut by the un-submerged rotating impeller. The off-center mounted impeller relies on a vortex of liquid around the impeller zone to create a net axial flow around the liquid bulk. This vortex, however, can create cyclic strains on the impeller shaft, which can lead to material fatigue and failure. Therefore this mode of mixing is limited to relatively low agitation rates and average energy dissipation rates, which can result in bioreactors that are less well mixed than those stirred bioreactors able to operate at higher agitation rates and P/V. The low agitation and energy dissipation rates can also limit scale up of such bioreactors. An additional consequence associated with a lack of power dissipation resulting from off-center agitation includes lower sensitivity of the volumetric oxygen mass transfer coefficient $k_La$ (h−1) to P/V, resulting in a bioreactor that is reliant on sparged gases to meet the cellular oxygen uptake requirement of cell culture processes. This uptake requirement can be achieved by employing sintered (microporous spargers) and/or greater sparge rates, which in turn can result in less favorable foaming characteristics due to the vessel operating under a greater interfacial shear environment. An alternative approach for mitigating this high interfacial shear regime is to increase the oxygen driving force (such as by greatly enriching the blend of oxygen in the sparge gases); however, this approach is also limited due to the concomitant buildup of metabolic $CO_2$, due to poorer mixing in the vessel, and $k_La$ production that can result with off-center agitated bioreactors.

With the single-mounted off-center impeller, relatively high and potentially problematic levels of 'localized' impeller-zone shear regimes are required to match the average energy dissipation rate, P/V, produced with a dual or multiple impeller agitated bioreactor. The scope for optimizing the impeller design/selection is limited by the mechanical strength and integrity of the off-center impeller shaft and the potential changes in the rheological properties of the cell culture process fluid (changes may be required to limit the mass and energy transfer from local to bulk) for vessels operating in fed-batch mode, with viable cell concentrations reaching $40\times10^6$ cells/mL to $50\times10^6$ cells/mL and a packed cell volume of 10% v/v, or for vessels operating in perfusion mode, with viable cell concentrations reaching 200 to $400\times10^6$ cells/mL and a packed cell volume of up 40% v/v.

With regard to centrally mounted impellers in unbaffled vessels, the lack of baffles in stirred bioreactors prevent the deflection of radial flow and under higher agitation rates and P/V's risk the formation of a vortex, which can lead to undesirable surface foaming within the bioreactor. In addition, without baffles within the bioreactor, the full capability of the impeller's power dissipation ability is not realized. Therefore the impellers are working sub-optimally in providing mixing and volumetric oxygen mass transfer coefficient, $k_La$, for any given agitation rate. Unbaffled bioreactors can create localized high shear zones and separate mixing zones within the bioreactor, which become more apparent when such design are scaled up to larger scale (e.g. more than 2,000 L). To promote the effect of baffles in an unbaffled bioreactor, previous designs have selected the base plate of the shell and the bioprocess container bottom design with a weir or ramp such that the radial flow at the bottom of the vessel is axially deflected. Whilst this may create axial flow, this flow is created around a localized point at the bottom of the vessel; as such, the strength of the axial flow can decay along the vertical axis of such a vessel unless the impellers within such vessels are agitating at relatively high power dissipation.

With regard to a non-circular vessel geometry, such as a cubic geometry, the radial flow produced by an impeller can deflect upon impacting each of the four sides of the vessel. Such design offer advantages for installation into a steel shell as each corner of the flat-packed bioprocess container can be easily aligned with the corners of the steel shell during installation. However, such bioreactors also have flat bottoms, resulting in some areas of concerns when compared with baffled cylindrical bioreactors having a curved base plate or bottom. Due to the perpendicular flat surfaces of the cube bioreactor, the counter current fluid flow produced by the agitator and deflection from vessel boundary results in greater occurrence of 'dead zones' along the edges and corners. To prevent occurrence of dead zones in the corners, hydrodynamic forces can be increased with scale up or greater power dissipation can be applied; however, both of these alternatives can result in greater mechanical fatigue of the seams at edge/corners. In addition, the fluid circulation off the bottom of flat bottomed bioreactors is less energetic due to production of counter-current flows from agitator-driven flows and deflection-driven flows from vessel bottom, resulting in less ability to keep cells and/or solids suspended in a flat bottomed bioreactor as compared to bioreactors having base plates designed around the ASME F&D-like geometry. In fact, cell/biomass sedimentation may become more acute in such bioreactors when used in a perfusion mode due to the higher cell concentration (typical 200 to $400\times10^6$ cells/mL are expected) and higher percent solids (typical pack cell volume of up 40% v/v are expected) obtained following cell retention within the bioreactors.

In current bioreactor designs, surface aeration is inadequate to provide the cellular oxygen uptake rate needed for most fed-batch applications and is highly unlikely to support cell growth in a perfusion mode where cells are retained within the bioreactor. Additionally, current bioreactors designed to deliver culture aeration through the surface are limited in their ability to be scaled up due to the ever reducing surface area to volume ratio. This means that, as such designed vessels are scaled up, the efficiency of and capacity for surface aeration deteriorates.

Where there are design inadequacies related to impeller or vessel geometries, the sinter or microporous spargers, such as sinter/microporous (having micrometer pores), a "combi-sparger" (composed of a mixture of 5 to 800 micrometer to sub-millimeter pores), or an open tube/pipe sparger, have been employed. Sintered spargers can produce fine or small gas bubbles that are more easily dispersed within the vessel bulk; in addition, due to their small size, the buoyancy forces of the gas bubbles are small, leading to greater residence time within the liquid bulk and oxygen mass transfer coefficient, $k_La$, at any given sparge rate. However, sintered spargers produce greater interfacial cell shear regimes and less effective metabolic $CO_2$ stripping, both of which are critical aspects in ensuring bio-comparability of cell culture processes during scale up and during vessel design transfer. Furthermore, the scale up of sintered spargers is not well understood and can lead to excessively fast linear velocity or pressure from sparge gases emerging from the sparge hole/pore lead to cellular damage. Similarly, the use of an open pipe sparger design with a bioreactor restricts the impeller design to a high shear type proximal to the sparger to permit bubble break up. Agitation rates are restricted to higher power dissipation to permit gas bubble breakage and distribution into the liquid bulk. Such bioreactors need to operate at higher shear mixing and aeration regimes to support the oxygen mass transfer requirement needed for fed-batch and perfusion cell culture processes as compared to bioreactors using other types of spargers such as variable sparger hole spargers.

With regard to inadequate designs of addition ports that permit application of feeds that are non-physiological in nature, such as feeds that have a very high or low pH or a high osmolality and can result upon exposure to cells in cell damage and death, current disposable bioreactors typically rely on addition ports that discharge onto the culture surface. While surface discharge may overcome the complex problem of routing the dip tube within the bioreactor and preventing the inadvertent siphoning of bioreactor content out through the dip tube, such bioreactors can suffer from creation of micro-zones of non-physiological environments at and just below the liquid surface. These zones will persist until the non-physiological materials are carried into the circulation zones produced by the impeller or into the flow deflected from the vessel boundaries and eventually blended into the bulk.

With regard to the harvest port and tubing design of current bioreactors, for perfusion modes of operation, the dip tube need to be appropriately sized to permit unobstructed flow of culture out of the bioreactor and into a coupled cell retention device and to allow return from the cell retention device back into the bioreactor without foaming and shearing of the cells or cell aggregates. An additional feature of such addition ports with external tubing attached, under high flow rate the dip tubing can collapse and impede the flow due to 'suction head' created upstream of the pump head that is driving the flow. The benefit of unimpeded flow of cell culture during perfusion mode or during harvest phase of a fed-batch process is critical to ensure the cells are not mechanically damaged whilst passing through such tubings, as mechanical damage can result in release of cellular factors (e.g. enzymes such as glutathione reductase, thioredoxin, and thioredoxin reductase or metabolites such as NADPH) which can adversely affect the performance of the process and quality of the product made. Secondly, unimpeded flow of cell culture can result in the culture not becoming hypoxic or anoxic whilst passing through such tubings and thereby prevent activation of the released cellular factors which can adversely affect the performance process and quality of the product during further processing. However, the harvest port and tubing design of all current disposable bioreactors are inadequate in these respects.

In the biomanufacturing and drug development industries, the production of products of cells, especially proteins, including receptor proteins, antibodies, peptides, exosomes, cellular fraction organelles, or whole cells, antibiotics or amino acids, and the like, must be of high quality to meet or exceed regulatory and customer requirements. The facility where such drug substances are often manufactured as multi-product. Therefore, there is an increased demand in the industry for single use bioreactors. There is also a demand for a SUB that can be scaled up during the production process so that the physicochemical environment, in view of dissolved oxygen, culture pH, temperature and shear sensitivity, and the nutritional environment, in view of concentration gradients that can inhibit the cell, are maintained. The current lack of scalability prevents the development of processes that can be consistently applied to the production of cell culture products. Indeed, the state of the art is such that cell culture product characteristics are inconsistent across scales, and production processes are for that reason typically modified at different scales to avoid the risk of inconsistent production. This is time consuming and expensive.

In comparison to the deficiencies presented by previous bioreactor designs, the present disclosure relates to single use bioreactors featuring enhanced operating characteristics and methods for the cultivation of cells using these single-use bioreactors.

SUMMARY OF DISCLOSURE

One of the objects of the present disclosure is to provide single-use bioreactors and methods, which allow the cultivation of mammalian cells in scalable volumes. Furthermore, it is an object of the present disclosure to provide single-use bioreactors and methods, which allow the cultivation of mammalian cells under optimal conditions, even if grown in large scale volumes and therefore allow a process performance and product quality independent of the size of the single-use bioreactor.

It is a further object of the disclosure to provide single-use bioreactors capable of producing products corresponding to products produced in similarly sized stainless steel STR bioreactors. It is a further object of the disclosure to provide single-use bioreactors featuring enhanced operating characteristics.

It is an object of the present disclosure to provide single-use bioreactors which allow the cultivation of mammalian cells in a homogenous environment with respect to process parameters such as pH, dissolved oxygen tension (DOT) and temperature, maintaining a well-mixed cell suspension and blending nutrient feeds within the bioreactor. In a preferred embodiment, the single-use bioreactor of the present disclosure would have integrated media and feed preparation to support both perfusion and fed batch. Ideally, this would be an automated facility ready to batch media and feeds as required and integrate with the production and inoculum systems as required.

The design of the single-use bioreactors according to the present disclosure can ensure a homogenous environment with respect to process parameters such as pH, dissolved oxygen tension (DOT) and temperature, maintaining a well-mixed cell suspension and blending nutrient feeds within the single-use bioreactor. This provides the necessary physicochemical environment for optimal cell growth, product accumulation and product quality. The present disclosure provides single-use bioreactors and methods which allow the cultivation of mammalian cells under optimal conditions, even if grown in large scale volumes and therefore allow a process performance and product quality independent of the size of the single-use bioreactor.

It is also an object of the present disclosure to provide single-use bioreactors with proportions that can be scaled from laboratory scale to industry scale bioreactors and vice versa. The design of the single-use bioreactors according to the present disclosure has this flexibility because it maintains geometric similarity.

In general, the present disclosure is directed to a bioreactor system and method. The present disclosure is also directed to a single use bioreactor that is well suited to incubating cell cultures and thereafter being disposed. The single use bioreactor of the present disclosure can be scaled to any suitable size and is designed to fit in pre-existing stainless steel structures. The bioprocess system and method of the present disclosure contain many unique aspects and features.

According to one aspect of the disclosure, a single-use bioreactor is provided. The single-use bioreactor may include a bioprocess container, a shell, at least one agitator, at least one sparger, at least one gas filter inlet port for the sparger(s) and headspace overlay, at least one fill port, at least one harvest port, at least one sample port, and at least one probe.

In one embodiment, the present disclosure is directed to a bioreactor comprising a bioprocess container. The bioprocess container is made from a liquid impermeable and flexible shape-conforming material. For instance, the bioprocess container can be made from a flexible film, such as a multi-layer film. In one embodiment, for instance, the film is comprised of a polyethylene polymer, such as a low density polyethylene that has been modified to form a hydrophilic surface. The hydrophilic surface is for contact with cell cultures within the bioreactor and improves wettability. In one embodiment, the polyethylene polymer is modified by being subjected to irradiation, photo or plasma induction, or oxidation.

The bioprocess container can have a top, a bottom, and at least one side wall therebetween. The bioprocess chamber can define a hollow enclosure for receiving a culture media. The hollow enclosure can have any suitable volume, such as 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters.

The bioreactor can include at least one inlet port for feeding materials into the hollow enclosure of the bioprocess container. A mixing device comprising a rotatable shaft coupled to at least one agitator can extend into the hollow enclosure of the bioprocess container. In one embodiment, the rotatable shaft can be collapsible. For instance, the rotatable shaft can include at least one impeller made from a hydrophilic polymer material that is collapsible or foldable towards the rotatable shaft.

The bioreactor can also include at least one baffle configured to extend adjacent to the side wall of the bioprocess container in a longitudinal direction. The baffle can have a shape that extends radially inward from the side wall an amount sufficient to affect fluid flow in the hollow enclosure during mixing of a culture media by the mixing device. The baffle can be collapsible and/or foldable. In one embodiment, for instance, the baffle can define an inflatable fluid bladder making the baffle capable of being inflated and deflated. The baffle can be integral with the bioprocess container meaning that the baffle is formed into the flexible shape-forming material. Alternatively, the baffle can be separate from the bioprocess container. The baffle can be configured to be placed inside the hollow enclosure or can be placed outside the hollow enclosure. When placed outside the hollow enclosure, the side wall of the bioprocess container conforms around the shape of the baffle. For example, in one embodiment, the baffle can be removably attached to an outer metallic shell. The bioprocess container can be placed in the metallic shell for conforming around the shape of the baffle. The bioreactor, in one embodiment, can include from about two to about six baffles that are spaced around a circumference of the hollow enclosure of the bioprocess container.

In one embodiment, the bioprocess container has a diameter and the one or more baffles extend radially inward a distance of from about 3% to about 20%, such as from about 5% to about 15% of the diameter of the bioprocess container.

The bioreactor can further include at least one sparger. The sparger, for instance, may comprise a ballast sparger that comprises a gas tube having a longitudinal portion and a lateral portion. The longitudinal portion can extend vertically into the hollow enclosure of the bioprocess container. The lateral portion, on the other hand, can be located at an end of the longitudinal portion below the agitator. The lateral portion can define a plurality of holes for releasing a gas into a culture media contained within the bioprocess container. In one embodiment, the plurality of holes are drilled. The lateral portion can have any suitable shape. In one embodiment, the lateral portion can be configured to engage the rotatable shaft of the mixing device for stabilizing the shaft. The rotatable shaft may extend through the lateral portion or can be housed within a shaft receiving member formed into the lateral portion.

In one embodiment, the bioreactor includes a first subsurface sparger and a second supersurface sparger. The plurality of holes in the subsurface sparger can be larger or smaller than the plurality of holes on the supersurface sparger. In one embodiment, the plurality of holes are drilled.

In one embodiment, the bioreactor can include at least one feed line that extends into the hollow enclosure for feeding fluids into the bioprocess container. The feed line can include a subsurface fluid outlet positioned adjacent the agitator. The fluid outlet can be associated with a fluid control device that only permits fluid to flow out of the fluid outlet and prevents fluid flow in an opposite direction. For instance, the fluid control device may comprise a one-way valve.

In another embodiment, the bioreactor can include a feed line positioned at the top of the bioprocess container. The feed line can include a supersurface fluid discharge positioned above a volume of culture media residing in the bioprocess container. The supersurface fluid discharge can be located such that a fluid flowing through the fluid discharge makes direct contact with a culture media contained within the bioprocess container. In one embodiment, the agitator can form a circumference when rotated and the supersurface fluid discharge of the feed line can be positioned above the circumference of the agitator such that fluids flowing through the fluid discharge contact the culture media within the circumference.

The bioreactor can be placed in operative association with a load cell for indicating a mass of a culture media contained within the hollow enclosure. The bottom of the bioprocess container can have a dome-shape for facilitating drainage. For instance, the bioprocess container can include a drain line located at the bottom of the bioprocess container. A fluid collecting device can be positioned inbetween the hollow enclosure of the bioprocess container and the drain line. The fluid collecting device can have a shape configured to induce a vortex flow of fluids from the bioprocess container into the drain line. In one embodiment, the drain line has a cross-sectional area that is proportional to the volume of the hollow enclosure. For example, for exemplary purposes, the drain line can have a cross-sectional area of from about 0.3 mm$^2$ to about 0.7 mm$^2$, such as from about 0.4 mm$^2$ to about 0.6 mm$^2$ per liter of volume of the hollow enclosure.

In one embodiment, the bioprocess container can include a plurality of ports for connecting to a plurality of supply lines for feeding fluids to the bioprocess container. Each port and corresponding supply line can include matching indicators for assisting a user in connecting the supply lines to the respective ports. The matching indicators, for instance, may comprise color such that each port and corresponding supply line are color-coded. Matching indicia can also be applied to feed lines and any corresponding ports and to spargers and any corresponding connectors.

In one embodiment, the bioprocess container can include ports that comprise universal connectors. The ports can have a first end and a second end. The first end can be for forming a reconnectable attachment to a respective supply line. Each supply line can include a fluid filter positioned upstream from the corresponding ports.

The present disclosure is also directed to a bioreactor system. The bioreactor system can include a bioprocess container made from a liquid impermeable and flexible shape-conforming material. The bioprocess container can have a top, a bottom, and at least one side wall therebetween. The bioprocess chamber can define a hollow enclosure for receiving a culture media. The bioprocess container can also include a plurality of inlet ports for feeding materials into the hollow enclosure. A drain line can be positioned at the bottom of the bioprocess container for draining fluids. A mixing device can extend into the hollow enclosure of the bioprocess container and can comprise a rotatable shaft coupled to at least one agitator.

The bioreactor system can further include at least one sensor in operative association with the bioprocess container for monitoring at least one parameter within the hollow enclosure. The at least one sensor can comprise a pH sensor, a dissolved carbon dioxide sensor, a dissolved oxygen sensor, a load cell, a temperature sensor, or a tachometer. A controller can be placed in communication with the at least one sensor. The controller can be configured to receive information from the at least one sensor and, based on the information, to control a fluid supply for varying a flow rate of a fluid from the fluid supply into the hollow enclosure of the bioprocess container for maintaining the at least one parameter of a culture media contained within the hollow enclosure within preset limits.

For example, in one embodiment, the bioreactor system can include a carbon dioxide gas supply in fluid communication with the bioprocess container and a liquid alkali supply also in fluid communication with the bioprocess container. The at least one sensor can comprise a pH sensor and the controller can be configured to regulate pH levels of a culture media within the preset limits by adding amounts of carbon dioxide gas from the carbon dioxide gas supply for selectively lowering the pH or by adding amounts of an alkali from the liquid alkali supply for selectively increasing the pH. In one embodiment, the system can include a first pH sensor and a second pH sensor both in communication with the controller.

In yet another embodiment, the bioreactor system can include an oxygen gas supply and the at least one sensor can comprise a dissolved oxygen sensor. The controller can regulate dissolved oxygen levels within a culture media within preset limits by periodically adding amounts of oxygen gas from the oxygen gas supply to a culture media based on information received from the dissolved oxygen sensor.

In still another embodiment, the bioreactor system can include a carbon dioxide gas supply and wherein the at least one sensor comprises a dissolved carbon dioxide sensor. The controller can be configured to regulate dissolved carbon dioxide levels within a culture media within preset limits by periodically adding amounts of carbon dioxide gas from the carbon dioxide gas supply to a culture media based upon information received from the dissolved carbon dioxide sensor.

In still another embodiment, the bioreactor system can include a thermal jacket surrounding the bioprocess container. The thermal jacket can be in fluid communication with at least one of a heated fluid or a chilled fluid. The bioreactor system can further include a temperature sensor for sensing a temperature of a culture media contained within the bioprocess container. The temperature sensor can be in communication with the controller. The controller can be configured to receive information from the temperature sensor, and, based on the information, control flow of a fluid into the thermal jacket for increasing or decreasing the temperature of a culture media contained in the bioprocess container for maintaining a culture media within preset temperature limits.

In another embodiment, the bioreactor system can further include a tachometer for monitoring a rotational speed of the rotatable shaft coupled to the at least one agitator. The tachometer can be in communication with the controller. The controller can be in communication with a motor that rotates the shaft. The controller can be configured to control the motor in a manner that rotates the shaft at a predetermined speed based upon information received from the tachometer.

The controller may comprise one or more microprocessors.

In one embodiment, the controller can be configured to receive information from multiple sensors in order to control multiple parameters within the bioreactor.

In one embodiment, one or more of the sensors described above can be integrated into the bioprocess container and can be disposable with the bioprocess container.

The present disclosure is also directed to a bioreactor comprising a bioprocess container made from a liquid impermeable and flexible shape-conforming material. The bioprocess container can have a top, a bottom, and at least one side wall therebetween. The bioprocess chamber can define a hollow enclosure for receiving a culture media. At least one feed line can extend into the hollow enclosure for feeding a fluid into the bioprocess container.

In one embodiment, the feed line includes a subsurface fluid outlet positioned adjacent to an agitator. The fluid outlet can be associated with a fluid control device that only permits fluid to flow out of the fluid outlet and prevents fluid flow in an opposite direction.

In an alternative embodiment, the feed line can comprise a supersurface fluid discharge positioned above a volume of a culture media residing in the bioprocess container. The supersurface fluid discharge can be located such that a fluid flowing through the fluid discharge makes direct contact with a culture media contained within the bioprocess container without contacting the side wall.

In one embodiment, the bioreactor can include a first feed line that includes the subsurface fluid outlet and a second feed line including the supersurface fluid discharge. In one embodiment, the bioreactor can contain from about one to about five, such as from about two to about three feed lines that have a supersurface fluid discharge.

In yet another embodiment, the present disclosure is directed to a method for producing a single use bioreactor.

The method includes the steps of constructing a bioprocess container from a liquid impermeable and flexible shape-conforming material. The bioprocess container having a top, a bottom, and at least one side wall therebetween. The bioprocess chamber defines a hollow enclosure for receiving a culture media. The hollow enclosure can have a volume of from about 10 liters to about 20,000 liters. The bioprocess container includes a plurality of inlet ports for feeding materials into the hollow enclosure of the bioprocess container. Each inlet port has a diameter.

A mixing device is inserted into the hollow enclosure. The mixing device comprises a rotatable shaft coupled to at least one agitator. At least one sparger is also inserted into the hollow enclosure of the bioprocess container. The sparger comprises a gas tube that has a longitudinal portion and a lateral portion. The longitudinal portion extends vertically into the hollow enclosure. The lateral portion is located at an end of the longitudinal portion below the agitator. The lateral portion defines a plurality of holes for releasing a gas into a culture media contained within the bioprocess container. The plurality of holes have a diameter.

A drain line is connected to the bottom of the bioprocess container. The drain line has a cross-sectional area.

In accordance with the present disclosure, the diameter of the inlet ports, the diameter of the plurality of holes on the sparger, and the cross-sectional area of the drain line are proportional to the volume of the hollow enclosure. The drain line, for instance, can have a cross-sectional area of from about 0.3 mm$^2$ to about 0.7 mm$^2$ per liter of volume of the hollow enclosure.

The present disclosure is also directed to a bioreactor comprising a bioprocess container made from a liquid impermeable and flexible shape-conforming material. The bioprocess chamber can define a hollow enclosure for receiving a culture media and can include at least one inlet port. A mixing device comprising a rotatable shaft coupled to a plurality of agitators can extend into the hollow enclosure of the bioprocess container.

In accordance with the present disclosure, the bioreactor can further include a cell retention chamber in fluid communication with the hollow enclosure of the bioprocess container. A filtrate outlet can be placed in fluid communication with the cell retention chamber. The filtrate outlet includes a biofilter that is permeable to liquids but impermeable to biological materials contained in a culture media. The filtrate outlet is for removing liquids from the cell retention chamber continuously or periodically. A flow regulator is configured to alternate flow of a culture media between the hollow enclosure of the bioprocess container and the cell retention chamber for carrying out a perfusion process.

The flow regulator, for instance, can be in communication with a pressurized gas source and a vacuum source. The flow regulator can be configured to alternatively apply a vacuum or a gas pressure to a fluid contained in the cell retention chamber for recycling fluids back and forth between the hollow enclosure of the bioprocess container and the cell retention chamber.

In one embodiment, the flow regulator can include a reciprocating diaphragm that alternates between applying pressure and applying a suction force to the fluid contained in the cell retention chamber.

The present disclosure is also directed to a bioreactor comprising a bioprocess container made from a liquid impermeable and flexible shape-conforming material. The bioprocess container defines a hollow enclosure for receiving a culture media. A mixing device comprising a rotatable shaft coupled to at least one agitator can extend into the hollow enclosure of the bioprocess container. In accordance with the present disclosure, the agitator can be collapsible onto the rotating shaft. For instance, the agitator can comprise an impeller comprising at least one blade element. The blade element can be foldable towards the rotatable shaft. In one embodiment, the rotatable shaft is coupled to a first impeller and a second impeller and both impellers can include at least one blade element that is foldable. A retaining ring can be positioned on the shaft. The retaining ring can include an agitator engaging position and an agitator disengaging position for holding the agitator in an upright position during mixing or in a collapsed and folded position respectively.

In one embodiment, the rotatable shaft comprises a metallic reinforcing rod surrounded by a shaft sleeve. The metallic reinforcing rod, which can be made from stainless steel, can be made from multiple pieces that are attached together. The top of the reinforcing rod can include a magnetic member for magnetically engaging a motor. The shaft sleeve can be comprised of a polymeric material. The agitator on the shaft can also be made from a polymeric material, such as a hydrophilic polymer. For example, the shaft sleeve and the agitator can comprise a polyethylene polymer that has been modified by being subjected to irradiation, photo or plasma induction, or oxidation.

In some embodiments, the single-use bioreactor can be configured for growing mammalian, insect, plant, other eukaryotic cells; microbial cells, including bacteria, yeast, and protozoan cells, and viruses; tissues; proteins; cellular products, such as organelles, enzymes, lipids, carbohydrates, and cell fractionates; exozymes; and cocultured organisms.

According to some aspects of the disclosure, the cultivated cells are eukaryotic cells, such as animal cells, such as mammalian cells. The mammalian cells can be for example human cell lines, mouse myeloma (NS0)-cell lines, Chinese hamster ovary (CHO)-cell lines or hybridoma-cell lines. In one embodiment, the mammalian cells are CHO-cell lines.

In one embodiment, the cultivated cells are used to produce antibodies, including monoclonal or polyclonal antibodies, and/or recombinant proteins, such as recombinant proteins for therapeutic use. Of course the cells may also produce vesicles, exosomes, organelles, peptides, amino acids, fatty acids or other useful biochemical intermediates or metabolites. In addition, in some embodiments, the cultivated cells or tissues formed therefrom may be the desired end product. The target concentration of the products produced by the cultivated cells may vary. For example, in one particular embodiment, the target concentration of the proteins produced by the cultivated cells can be more than 0.01 g/l, such as more than 0.1 g/l, such as more than 0.5 g/l, such as more than 2.0 g/l, such as more than 10.0 g/l depending on culture volume. The method according to the disclosure can be used as a batch, fed-batch, perfusion, or draw and fill process. Although the cell-culture-medium used in the method according to the disclosure is preferably protein free medium, the design does not exclude the use of protein containing streams.

In one embodiment, a single use bioreactor system according to the instant disclosure comprises: a single use cell culture bioprocess container ("SUB"), a reusable shell in which the SUB is held during operation, and a controller that controls the operation of the SUB and associated sub-systems and processes. Associated sub-systems include an agitation system, a baffle system, a sparger system, a feeding system, a harvesting system, a monitoring system, control system(s), and a fill system.

In one embodiment, each of cell culture contacting and process fluid contacting surface of the SUB are preferably animal derived component free.

According to one aspect of the disclosure, a single-use bioreactor is provided. The single-use bioreactor may include a bioprocess container, a shell, at least one agitator, at least one sparger, at least one gas filter inlet port for the sparger(s) and headspace overlay, at least one fill port, at least one harvest port, at least one sample port, and at least one probe.

According to another aspect of the disclosure, a single-use bioreactor system is provided. The single-use bioreactor system may include a bioprocess container, a shell, at least one agitator, at least one sparger, at least one gas filter inlet ports for the sparger(s) and headspace overlay, at least one fill port, at least one harvest port, at least one sample port, and at least one probe According to yet another aspect of the disclosure, a single-use bioreactor system for the cultivation of mammalian cells is provided. The system may include a first single-use bioreactor, connected to at least one other bioreactor. The at least one other bioreactor may have a greater volume than said first single-use bioreactor and connected with any number of single-use bioreactors. Each additional single-use bioreactors may have an increased volumes as compared to the prior single-use bioreactor. The multiple bioreactors may maintain a homogeneous environment with respect to pH, dissolved oxygen tension (DOT) and temperature, thus allowing for a well-mixed cell suspension and a blending of nutrient feeds within the bioreactor.

According to a further aspect of the disclosure, a method to cultivate and propagate mammalian cells is provided. The method may include cultivating under suitable conditions and in a suitable culture medium in a first single-use bioreactor, transferring the medium containing the cells obtained by propagation from the at least one mammalian cell is into a second single-use bioreactor, transferring the medium containing the cells obtained by propagation from the at least one mammalian cell is into a third single-use bioreactor, and cultivating the cells in the third bioreactor.

According to an additional aspect of the disclosure, a single use bioreactor (SUB) system is provided. The system may include a flexible bioreactor bioprocess container that is for single use and disposable, a SUB shell configured to hold the flexible bioreactor bioprocess container, an agitator, a sparger, a plurality of ports, and at least one controller configured to control a plurality of parameters associated with the SUB system such that the SUB system produces biomaterial corresponding to biomaterial capable of being produced in a similarly sized stainless steel bioreactor.

In still another embodiment of the present disclosure, a bioreactor is disclosed that comprises a bioprocess container made from a liquid impermeable and flexible shape-conforming material, such as a flexible film. The bioprocess chamber defines a hollow enclosure for receiving a culture media. A mixing device comprising a rotatable shaft coupled to at least one agitator extends into the hollow enclosure of the bioprocess container. In accordance with the present disclosure, the rotatable shaft can be coupled to a top impeller and to a bottom impeller. Both the top impeller and the bottom impeller can be made from a polymer material. For instance, in one embodiment, the impellers may be 3-D printed. The top impeller and the bottom impeller can both define a hydrophilic surface. For instance, the polymer material used to form the impellers can comprise a hydrophilic polymer or can comprise a polymer that has been surface modified so as to render the surface hydrophilic.

In one embodiment, for instance, the top impeller and bottom impeller are made from a polyolefin polymer, such as polyethylene or polypropylene. In one embodiment, low density polyethylene can be used. The low density polyethylene can be modified by being subjected to irradiation, photo or plasma induction, or oxidation to form a hydrophilic surface.

The top impeller can comprise a hydrofoil impeller. The bottom impeller, on the other hand, can comprise a four pitched-bladed high solidity impeller. The impeller to tank diameter ratio can be from about 0.35 to about 0.55, such as from about 0.44 to about 0.46. The top impeller and the bottom impeller can have power numbers ($N_p$) of from about 0.1 to about 0.9 and can have flow numbers ($N_q$) of from about 0.4 to about 0.9.

Other features and advantages of the present disclosure will become apparent from the following more detailed description, taken in conjunction with the accompanying drawings, which illustrate, by way of example, the principles of the presently described disclosure.

BRIEF DESCRIPTION OF THE FIGURES

The patent or application file contains at least one drawing executed in color. Copies of this patent or patent application publication with color drawing(s) will be provided by the Office upon request and payment of the necessary fee.

In FIG. 1A, bioreactor vessel 1 includes a bioprocess container 100 fitted inside a shell 110. The bioprocess container 100 comprises a shape-conforming material 12. The shell 110 comprises a bottom 4 that, in one embodiment, can serve as a holder for the bioprocess container 100. The bottom of the bioprocess container 100 can be configured to conform to or fit the shape of the shell bottom 4. Vortex breaker 2 is placed at the bottom vessel for avoiding air entrapment during draining, a harvest/drain line 3, dual spargers 5, a lower impeller 6, an upper impeller 7, an impeller shaft 8 vertically imposed inside the bioprocess container, and baffles 9. 10 is the light protection for the top of the vessel. 11 is the foam sensor. 13 is a spectroscopic probe window. 14 represent subsurface dip tube, which disgorge in the impeller region to ensure rapid dispersion of concentrated or non-physiological feeds. 15 represent all tubes into the vessel which are systemically controlled to prevent connection of the wrong tubes together. 16 represents all feedlines. In one embodiment, 16 represents the disgorging ports of surface feedlines configured such that the feed does not run down the side of the bioprocess container. In an aspect of the disclosure, at least 3 feedlines discharging above the surface of the culture are required. 17 are the inline sterile filters. 19 represents the pressure sensor(s). 20 is the sterile solids addition port. 21 represent dual gas outlet ports. 30 is the robust agitator shaft. 170 is the motor.

In FIG. 1B, vessel 1 includes a bioprocess container 100 fitted inside a shell 110. The bioprocess container comprises a vessel conforming film 12. The shell also includes a dish bottom 4 that serves as a bioprocess container holder, vortex breaker 2 placed at the bottom vessel for avoiding air entrapment during draining, a harvest/drain line 3, dual spargers 5, a lower impeller 6, an impeller shaft 8 vertically imposed inside the bioprocess container, and baffles 9. 10 is the light protection for the top of the vessel. 11 is the foam sensor. 13 is a spectroscopic probe window. 14 represent subsurface dip tube. 15 represent all tubes into the vessel which are systemically controlled to prevent connection of the wrong tubes together. 16 represent all feedlines. In one embodiment, 16 represents the disgorging ports of surface feedlines configured such that the feed does not run down the side of the bioprocess container. In an aspect of the disclosure, at least 3 feedlines discharging above the surface of the culture are required. 17 are the inline sterile filters. 19 represent the pressure sensor(s). 20 is the sterile solids addition port. 21 represent dual gas outlet ports. 30 is the robust agitator shaft. 170 is the motor.

As illustrated in FIG. 2, in this embodiment, the disgorging point of the feedline 16 extends substantially beyond the bioprocess container such that the feed drops onto the surface of the liquid contained within the bioprocess container without running or trickling down the side of the bioprocess container. In one, non-limiting embodiment, the disgorging point may assume the shape of a nipple or funnel.

In FIG. 3, 11 represent the foam protection sensors. 19 represent the pressure sensor(s). 20 is the sterile solids addition port. 21 represent dual gas outlet ports. 242 represent the tachometer. The arrangement 18 of top of the vessel is such that key elements can be held in place by projections of the bioprocess container holder. For example, motor 170 and agitator shaft head 30 are held in alignment for vertical imposition. The robust agitator shaft 30 is also supported by the base of the bioprocess container by components attached to the shell. Gas out lines may be held in vertical arrangement to prevent air locks and facilitate drainage of condensate back into the vessel.

DETAILED DESCRIPTION OF THE DISCLOSURE

Figure 1A:
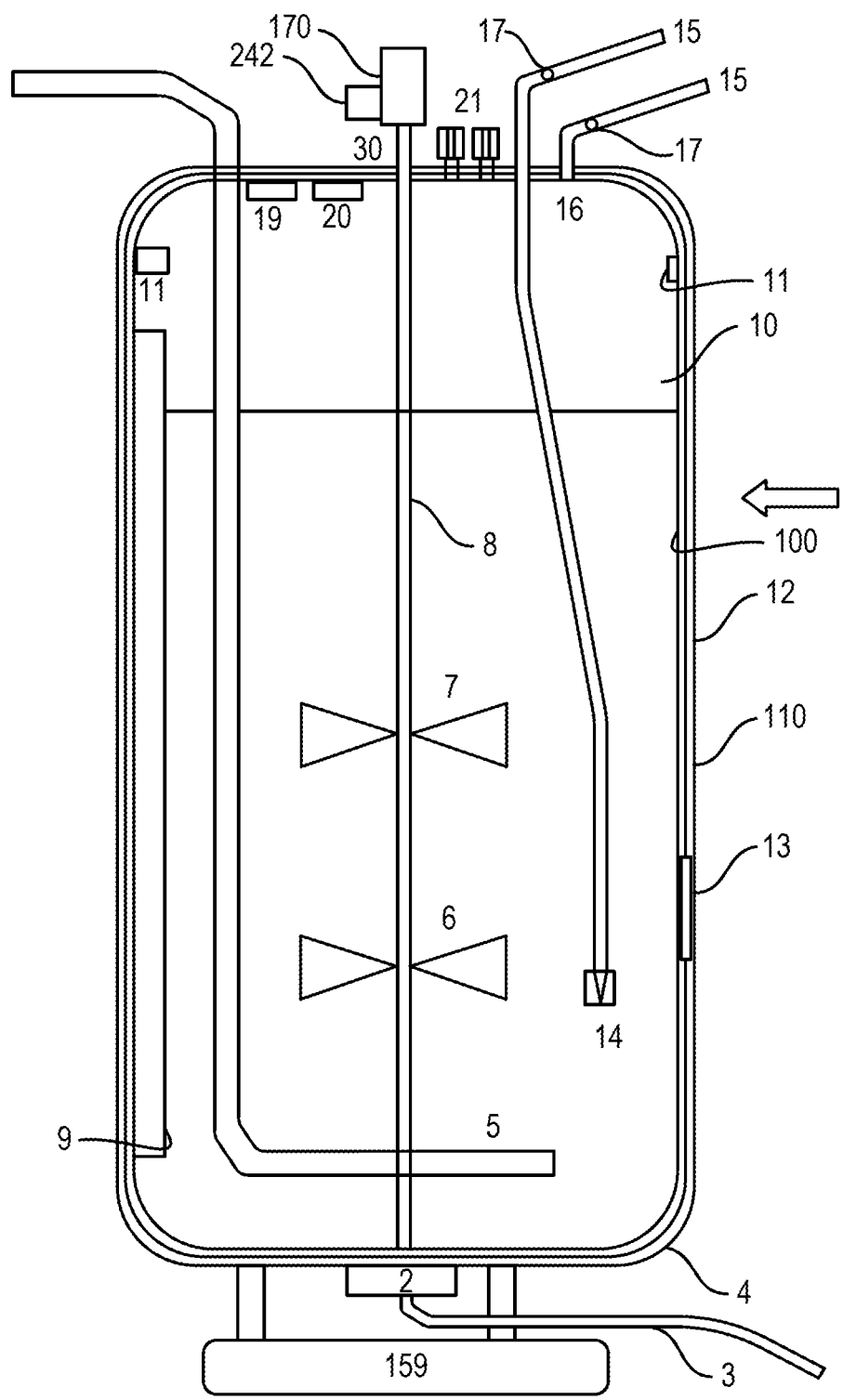
FIG. 1A shows a single use bioreactor (SUB) system according to an embodiment of the disclosure.

The present disclosure relates to systems, devices, and methods of culturing cellular biologic material in a bioreactor vessel, which are now described in detail with accompanying figures.

The single-use bioreactors contemplated by the present disclosure are capable of performing mammalian cell culture in fed-batch, continuous-batch, and/or perfusion mode or any combinations thereof.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the term "about" modifying the quantity of an ingredient, component, or reactant employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

According to the present disclosure, a single-use bioreactor is a biocompatible tank or vessel having additional equipment, for example impellers, baffles, spargers and/or ports, which specifically allows for the cultivation and propagation of mammalian cells. The single-use bioreactor of the present disclosure can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be single-use, disposable, or non-disposable and can be formed of any suitable material including, but not limited to, plastics.

Proportions of the SUB System

The design of the single-use bioreactor according to the present disclosure can, in one embodiment, ensure a homogenous environment with respect to process parameters such as pH, dissolved oxygen tension (DOT) and temperature, maintain a well-mixed cell suspension, and blend nutrient feeds within the single-use bioreactor. Thus, single-use bioreactors of the present disclosure can provide the necessary physicochemical environment for optimal cell growth, product accumulation, and product quality. The design of the single-use bioreactors according to the present disclose can also, in one embodiment, ensure the maintenance of geometric similarity.

In one embodiment, the scalable geometric similarity can be that described in U.S. Publication No. US 2011-0312087, which is incorporated by reference in its entirety.

Bioprocess Container (100)

The single use bioprocess container (100) is made from a flexible shape-conforming material 12. In one embodiment, the flexible bioprocess container and shape-conforming material may be configured such that the bioprocess container can be folded or otherwise compacted for storage. In one embodiment, the shape-conforming material may be a liquid impermeable and flexible shape-conforming material. The shape-conforming material may further be a film with low levels of leachables and low binding properties for hydrophobic compounds, such as substituted lipids, sterols, fatty acids, exosomes, silicon based emulsions, hydrophobic vitamins, and hydrophobic amino acids.

In one embodiment, the shape-conforming material may be compatible with a wide variety of cells and cell products. For example, in one particular embodiment, the shape-conforming material may be compatible with CHO cell line types following the methodology recommended for leachables studies in the DECHEMA report entitled "Standardized cell culture test for the early identification of critical films for CHO cell lines in chemically defined culture media" (Regine Eibl et al, January 2014).

The shape-conforming material of the bioprocess container of the present disclosure can, in one embodiment, be any acceptable flexible film. For example, in one embodiment, the shape-conforming material may be a monolayer film. Alternately, the shape-conforming material may comprise a multi-layer film. For example, in one embodiment, the film materials used herein can be compound films composed of 3 or more layers bonded with adhesives into a film. The multi-layer film includes an interior surface facing the hollow enclosure of the bioprocess container. The multi-layer film further comprises an opposite exterior surface. The layer(s) of the film may be selected to convey any suitable properties. For example, in an embodiment wherein the film material comprises at least 3 layers, the outer layer may be selected to confer mechanical strength, the middle layer may be selected to confer gas barrier properties, and the inner layer may be selected to be suitable for contacting the cell culture. The inner layer may be configured to contact the product within the bioprocess container while minimizing production effects due to the contact. For example, the inner layer may be generally formed of low density polyethylene. In one particular example, the interior surface of the multi-layer film may comprise a low density polyethylene that has been modified to form a hydrophilic surface. Other layers may be added to further modify the properties of the film. For example, in one embodiment, acrylamide may be grafted onto LDPE film. As another example, oxidized polyethylene can be used. Additional examples include polyethylene blends with poly(2-hydroxyethyl methacrylate), poly(2,3-dihydroxypropyl methacrylate), and the like. Other polymers, including other polyethylenes, may be suitable for use herein. In certain embodiments, any of the film layers described herein may be subjected to irradiation, photo or plasma induction, or oxidation.

The shape-conforming material is used in the construction of the single use bioreactor, including, in one embodiment, the addition of ports and other parts which may also come into contact with the cell culture. In one embodiment, the whole bioreactor and/or components thereof, once constructed, may then be gamma irradiated to ensure sterility.

In one embodiment, the materials used in the construction of the bioprocess container may be generally hydrophobic and may adsorb hydrophobic medium components from the culture medium. In one embodiment, this can lead to substantial differences in the growth and productivity of industrial cell lines. These differences, in one embodiment, may be generally overcome by addition of higher concentrations of these hydrophobic components in single use bioreactors than in traditional stainless steel bioreactors. In another embodiment, the polymer materials and adhesive materials used in the preparation of the films and components may contain additives, such as plasticizers, slip agents, release agents, antioxidants, or breakdown products thereof, designed to improve the properties of the plastics. In yet another embodiment, the surface properties of the vessel conforming film, which, in one embodiment, represents the largest hydrophobic culture contacting surface in the vessel, may be modified to make the contact surface more hydrophilic, thus increasing the film's wettability and reducing its propensity to bind hydrophobic components. For example, in one embodiment, the vessel conforming film may comprise a low density polyethylene culture contact layer. The polyethylene contact layer may be modified using gamma, beta or UV irradiation techniques, photo and plasma induction, or liquid based chemical oxidation. In a further embodiment, the materials used in the construction of the vessel conforming film and other components contacting the product stream can be controlled through the supply chain to ensure suitable quality of the materials. For example, stringent limits on impurities and on concentration ranges of components and on acceptable radiation doses can be applied, such as requiring that cell culture testing of raw material be performed before releasing the raw materials for use in construction of the vessel conforming film.

In at least one embodiment, the surface of the inner layer of the vessel conforming film can be modified such that it is more hydrophilic than unmodified low density polyethylene. Accordingly, in one embodiment, the surface of the inner layer has increased wettability and reduced propensity to bind hydrophobic components. The modified inner layer may include an inner surface that has been modified via one or more of: surface grating with hydrophilic components via gamma, beta or ultraviolet irradiation techniques; photo and plasma induction; and liquid based chemical oxidation.

In one embodiment, the bioprocess container may have or may assume a similar shape as the shell to avoid creases. In at least one embodiment, the bioprocess container may be configured to be held within the shell such that folding and/or creasing of the bioprocess container is minimized. The bioprocess container may be a molded container or bioprocess container that is molded to fit within the shell. Prior to or during operation, the bioprocess container may have a similar geometry to the shell, such as to the concavity of the shell.

In general, the bioprocess container has a top, a bottom, and at least one sidewall therebetween. Thus, the bioprocess container has generally a top, middle, and bottom portion. The bioprocess chamber defines a hollow enclosure, wherein the hollow enclosure may receive a content, such as culture media, of the bioprocess chamber. In one embodiment, the bioprocess container may have a dome shaped bottom and top to fit into the holder. In one embodiment, the bioprocess container may include a bottom portion shaped to fit a dished bottom of the shell without substantial folding and/or creasing. In one embodiment, the bioprocess container may include a top portion shaped to fit the cover without substantial folding and/or creasing.

In another embodiment, the bioprocess container may have color coded connections. The connections may be indirect or direct connections between at least two components of the bioprocess container.

In one embodiment, the bioprocess container may have at least one sparger. For example, the bioprocess container may have two spargers, which may have mechanically different connections. In one embodiment, the bioprocess container can have a dual sparger 5 with micro and macro holes. In one embodiment, the connections between the sparger may be color coded and/or mechanically different, such as to ensure operators cannot connect up the wrong line to the two different spargers.

In one embodiment, the bioprocess container may accommodate pressure, foam, pH and DO sensors and/or probes and/or subsurface dip tubes. The subsurface dip tubes may comprise a non-return valve. In one embodiment, the subsurface tube can be made from braided materials or more rigid materials. In one embodiment, the sensors, probes, and/or tubes may be disposable.

In one embodiment, the SUB may contain a pressure sensor that directly or indirectly measures the pressure in the bioprocess container. For example, in one embodiment, the pressure sensor may be located in or on the bioprocess container. In one particular embodiment, the pressure sensor may be built into the wall of the bioprocess container in order to ensure correct measurement. This sensor may be compatible for use with controller systems, such as those controller systems described herein.

In one embodiment, the bioprocess container may comprise a drain line. The bioprocess container may be in fluid communication with the drain line. The drain line has a cross-sectional area. In certain embodiments, the cross-section area of the drain line is chosen such that it is proportional to the volume of the hollow enclosure of the bioprocess container. For example, the drain line, in one embodiment, may have a cross-sectional area of from about 0.3 mm$^2$ to about 0.7 mm$^2$ per liter of working volume of the hollow enclosure. In one particular embodiment, the cross-sectional area of the drain line can have a cross-sectional area of at least 0.5 mm$^2$ per liter of working volume. In one embodiment, the drain line may be situated at the bottom-central region of the bioprocess container, such as at the center of the lowest point of the bioprocess container. In one embodiment, the drain line may be located at a location corresponding to the location of the fluid collecting device 3, which can be positioned inbetween the hollow enclosure of the bioprocess container and the drain line. In one embodiment, the fluid collecting device may have a shape configured to induce a vortex flow of fluids from the bioprocess container into the drain line, thus preventing entrapment of air. In alternate embodiments, a separate device may be provided to induce a vortex flow of fluids into the drain line.

The bioprocess container and holder may be able to function for either perfusion or fed batch mode. In one embodiment, the bioprocess container may include an outlet gas filter design, such as for a perfusion system. For example, in one embodiment, the single-use bioreactor could have a system that would enable recovery and/or re-circulation of the cells. In one embodiment, when operating in perfusion mode, the tubing on the bioprocess container could be modified, such as with manifolds, to allow for multiple entries without contamination as well as to cope with high flowrates.

The design of the bioprocess container, in one embodiment, may also have a bolt-on system. In one embodiment, this system could be a bolt that could be attached to the bioprocess container holder skid. Such a system could, in one embodiment, be switched off and/or disconnected when not in use. For example, the bolt may enable recovery and re-circulation of the cells for a perfusion format.

In one embodiment, the middle portion of the bioprocess container can have an aspect ratio of between about 0.3 to about 3, such as from about 0.8 to about 1.5, such as from about 1 to about 1.2. In one particular embodiment, the bioprocess container may have an aspect ratio of approximately 1.1 for the middle section.

Shell (110)

The single use bioreactor of the present disclosure can also incorporate features that make it easy to fit the bioprocess container in to the shell without compromising performance as compared to a stainless steel bioreactor.

In certain embodiments, the shell of the present disclosure can allow free draining without manipulating the bioprocess container towards the end of harvest, can protect the culture from light, can allow for the addition of baffles if required, can allow consistent contact with the bioprocess container and probes inside the bioprocess container, and can ensure fast heat transfer. In one embodiment, the bioprocess container itself can be molded to fit the shell or portions thereof to ensure that there are no folds.

The shell of the present disclosure can be of any suitable shape. In one embodiment, the shell may be generally cylindrical, while in other embodiments, the shell may be generally cubical or conical. In one embodiment, the shell has a scalable geometry before, after, and/or during operation in accordance with the scalable geometries described in U.S. Publication No. 2011-0312087 and U.S. Provisional Application No. 62/354,216, the entire contents of which are hereby incorporated by reference.

Figure 1B:
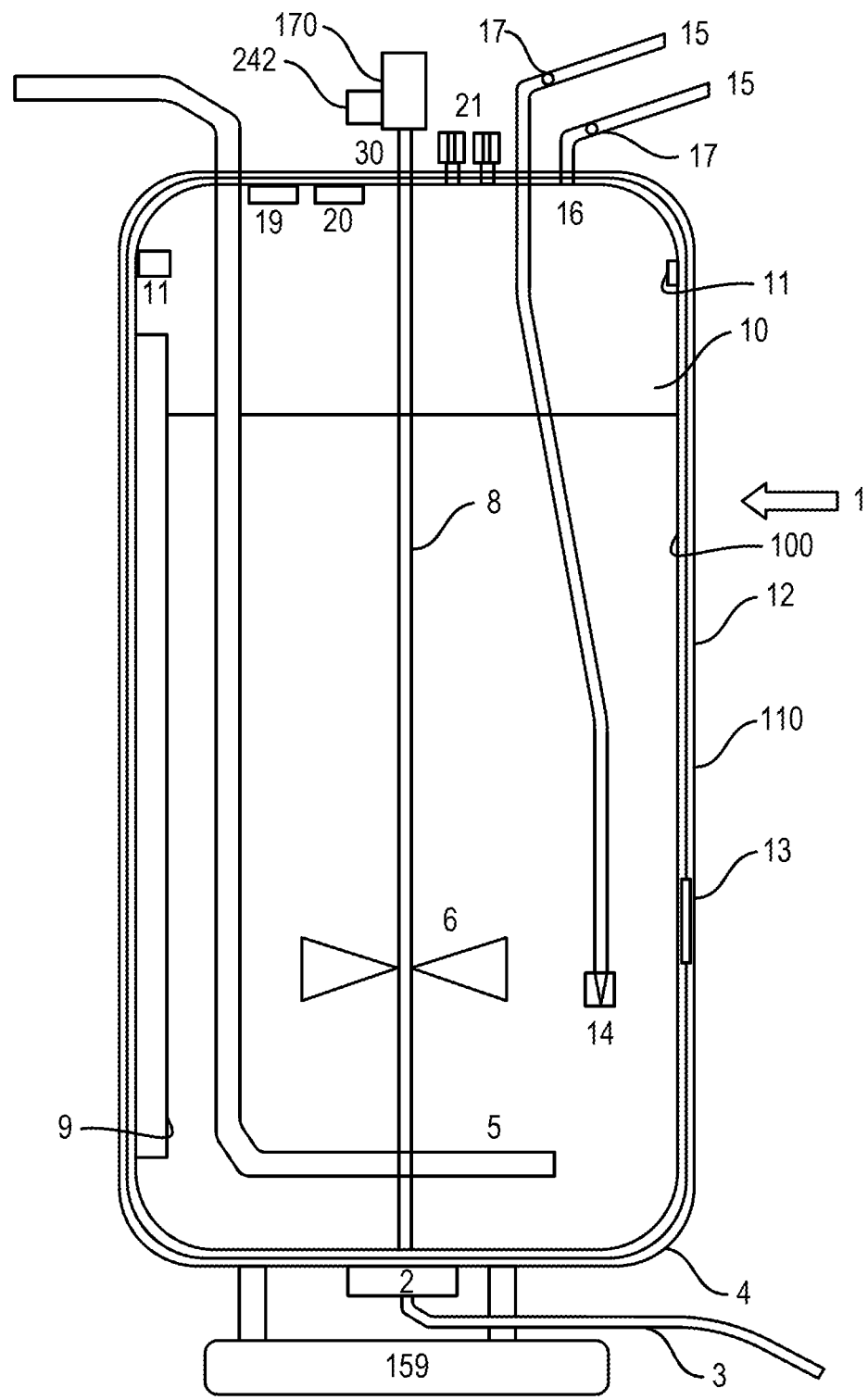
FIG. 1B shows a single use bioreactor (SUB) system according to an embodiment of the disclosure.

Referring to FIG. 1A and FIG. 1B, the shell 110 incorporates features that, in certain embodiments, make it easy to fit the bioprocess container 100 into the shell 110 without compromising performance. As shown in FIGS. 1A and 1B, bioprocess container 100 is fitted inside shell 110. The shell 110 comprises a bottom portion 4 that, in one embodiment, can serve as a holder for the bioprocess container 100. The bottom of the bioprocess container 100 can be configured to conform to or fit the shape of the shell bottom 4. The shell 110 further comprises a top portion 10 which can, in one embodiment, serve as a removable cover for the bioprocess container 100. The shell 110 comprises an upper portion, including top 10, and a lower portion, including bottom 4, together defining a concavity.

The bottom 4 and the top 10 of the shell may be of any suitable shape or curvature. For example, the bottom 4 and/or the top 10 may be flat or curved. The shape/curvature of the shell or components thereof may be concave, convex, or any variations therein.

In one embodiment, the shell bottom 4 may comprise a circular dished bottom. The dished bottom may be, in one embodiment, substantially circular. In one particular embodiment, the dish bottom of the shell may be American Society of Mechanical Engineers flanged and dished, or equivalent. The shell may further comprise at least one drain, such as a recovery drain, located at any suitable location in the shell. In one embodiment, the drain may be located in the shell bottom 4. In one embodiment, to ease draining, the drain may be located at the lowest point in the center of the dish, such as at a central nadir. In one embodiment, as shown in FIG. 1A and FIG. 1B, a vortex breaker 2 may be located in the region of the recovery drain 3 to aid in avoiding air entrapment during draining.

Figure 8:
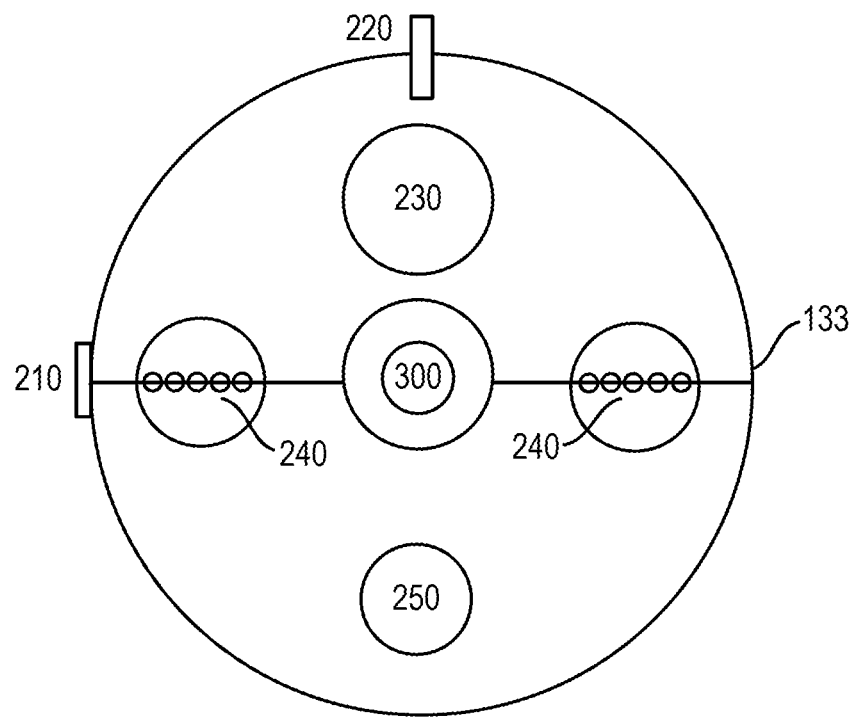
FIG. 8 illustrates a top of the bioprocess container holder cover according to an embodiment of the disclosure. The cover has gas inlet/gas outlet 230 and multiple feedlines 240. 300 is the motor coupling. 250 is the sight glass. 210 represent the clamps. 220 is the adjustable arm for filter holder. 133 is the hinge.
Figure 9A:
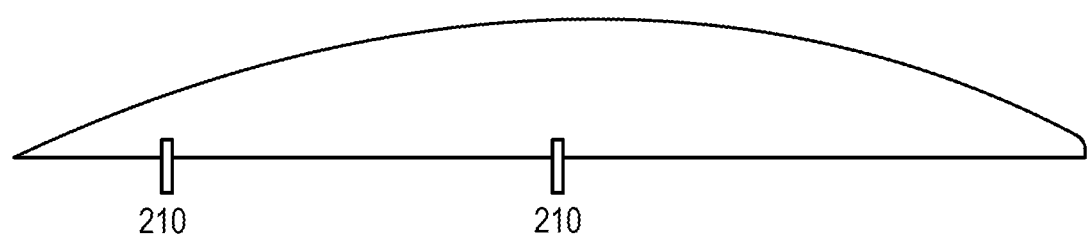
FIG. 9A illustrates a side view of the shell top cover according to an embodiment of the disclosure. 210 is the clamps.
Figure 9B:
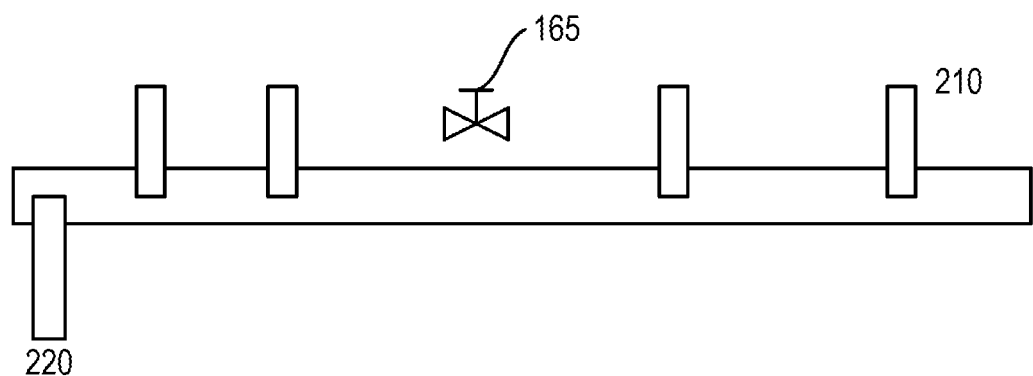
FIG. 9B illustrates a gas outlet filter holder according to an embodiment of the disclosure. 220 is the adjustable arm for the filter holder. 210 is the clamps. 165 is a pinch valve linked to a controller.

In one embodiment, the top of the bioprocess container can be configured such that it can protect the contents of the bioprocess container without a lid or cover. In an alternate embodiment, the top 10 of the shell 110 may comprise a top cover for the bioreactor that, in one embodiment, is designed to protect the bioreactor contents. Referring to FIGS. 8 and 9A, in at least one embodiment, the upper area of the shell 110 is at least partially capped by a cover configured to protect the bioprocess container contents from undesired exposure to light and/or the ambient environment. The cover may be coupled to the upper portion of the shell 110 such that it is readily removable and/or repositionable so as to permit access to the concavity of the shell 110 and thereby facilitate arrangement of the bioprocess container 100 within the shell 110.

In one embodiment, the shell may further comprise at least one fastener. In one embodiment, as shown in FIGS. 8 and 9A, one or more fasteners may fasten the cover of the shell 110 in a closed orientation such that the cover is not repositionable into an open orientation without disengaging the fastener. In at least some embodiments, the fastener comprises a clamp 210. In another embodiment, the clamp is made of stainless steel 316 L and has a wall thickness between ½" and 4". In yet another embodiment, the clamp is a stainless steel 304, 2 part high pressure clamp with nut and bolt. In one embodiment, the cover comprises two substantially semi-hemispheric dished areas configured to open and close via a hinge joint and lockable via one or more fasteners, such as clamp 210, as demonstrated in FIG. 8.

In one embodiment, the top of the shell may have ports, such as at least one port, at least two ports, at least three ports, at least four ports, for supply line or for feed line tubing to come in and/or out of. The top of the shell can also optionally have at least one sight glass, such as with light, and port(s) for the motor coupling. In one embodiment, the top of the shell is at least partially detachable. In one embodiment, the top of the shell can swing into place and be clamped shut. In one embodiment, the shell may also have a window to allow personnel to check the liquid and foam levels within the bioreactor. The shell may further comprise a lighting system to enable the operator to observe the liquid and foam levels.

Figure 10:
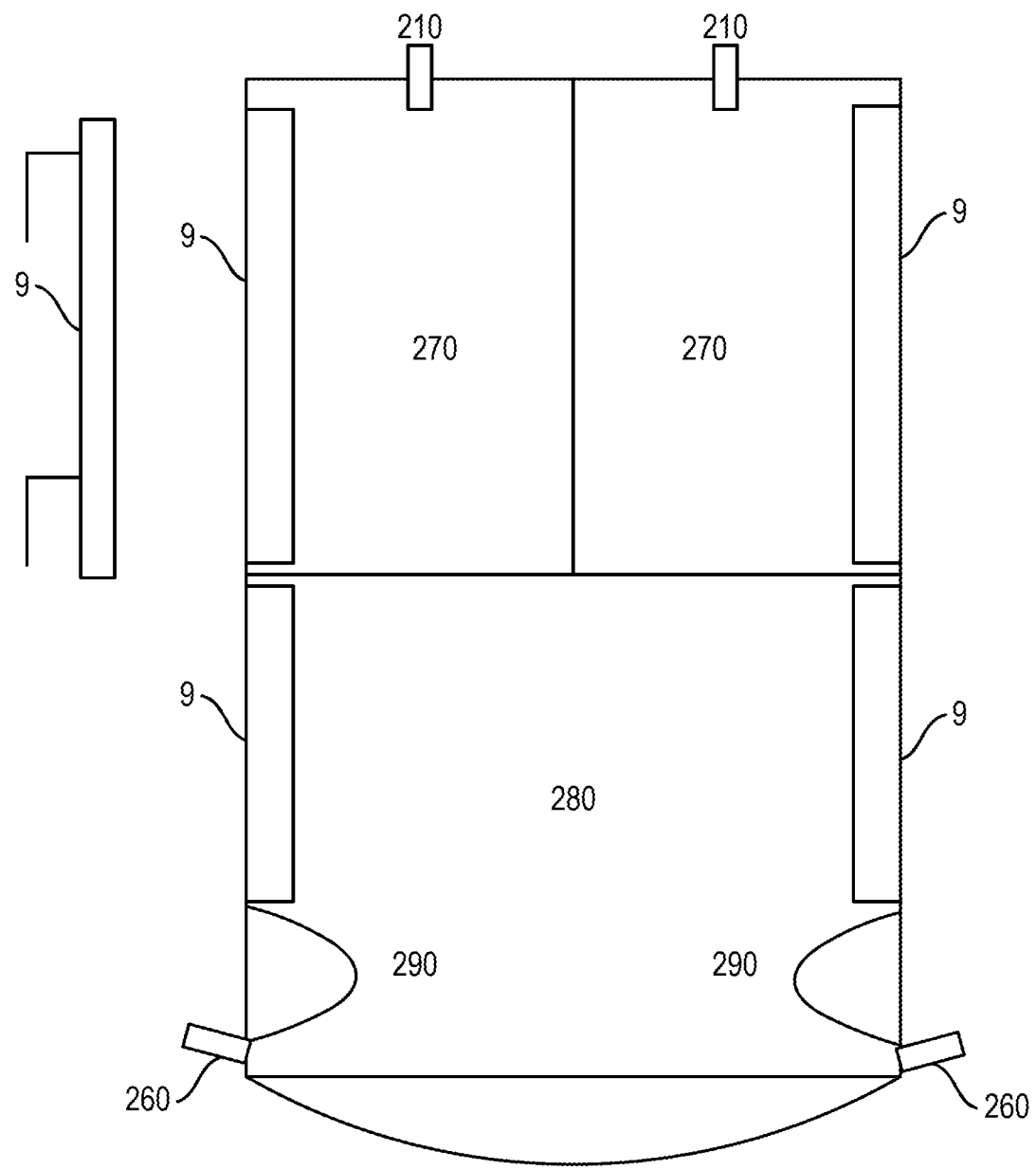
FIG. 10 illustrates a bioprocess container holder design according to an embodiment of the disclosure. 9 represents baffles. The baffles 9 are split into a top and a bottom portion. There are 4 sets of baffles each designed to hook into holes on the inside of the bioprocess container holder. 210 represent the clamps. 270 is the door. 280 is the jacket. 290 represent the probe belts. 260 represent probe shelving.

In at least one embodiment, the upper portion of the shell includes at least one door for access to the shell and/or the bioprocess container held therein. For example, in one embodiment, the upper portion of the shell comprises a hinged access door configured to permit access to the concavity of the shell and thereby facilitate arrangement of the bioprocess container within the shell. In one embodiment, one or more fasteners may fasten the at least one access door in the closed position. In one embodiment, as shown in FIG. 10, the upper portion of the shell may include opposing access doors 270 configured such that, when in a closed position, respective free edges abut each other and respective lower edges abut the lower portion of the shell. The one or more fasteners may be positioned at respective abutting inner edges and/or respective lower edges of the two doors.

In one embodiment, as shown in FIG. 1A and FIG. 1B, the single-use bioreactor 1 comprises a motor 170. The motor 170 may be provided for the agitator 8 and may be provided at any suitable location on or in the bioreactor. In one embodiment, the motor can be located and sitting in the center above the top 10 of the shell 110. In one non-limiting embodiment, the motor is held in place by an arm linked to the shell, such as to the top half of the shell. In another non-limiting embodiment, the bioprocess container may be clamped to the top of the shell, such as to the top cover, with the motor on an arm that can be lowered. In a further non-limiting embodiment, the bioprocess container and the motor may be magnetically attached to the top of the shell, such as to the top cover, thereby helping to hold up the bioprocess container.

In some embodiments of the bioreactor of the present disclosure, as shown in FIGS. 1A and 1B, the shell will include an integrated load cell 159, wherein the load cell may be in operative association with the bioprocess container. In one embodiment, the load cell may be capable of measuring the mass of the culture, such as to a precision of +/−0.005% or +/−0.05%. In one embodiment, the load cell will generate a signal compatible with the controller systems discussed below. As such, in some embodiments, the load cell may indicate a mass of a culture media contained within the hollow enclosure of the bioreactor container.

The shell of the present disclosure may be constructed out of any desired material(s). In one embodiment, the shell may be constructed of stainless steel 316 L. In certain embodiments, the shell is suitable for cleaning and/or treatment with cleaning agents, antimicrobial agents, disinfectants, and the like. Non-limiting examples of cleaning agents include Klericide Disinfectant, Biocide and/or Sporkenz, or the like. Agitators 6, 7

In one embodiment, the single use bioreactor further comprises a mixing device comprising a rotatable shaft couple to at least one agitator. In one embodiment, the shaft and agitator extend into the hollow enclosure of the bioprocess container; as such, in some embodiments, the contents of the bioprocess container shall be mechanically circulated using an internal mixing system. In most embodiments, the agitator is rotated, via a motor or the like, such that it forms a circumference. In one embodiment, the mixing system may comprise an impeller system, such that the agitators may comprise impellers.

Referring to FIG. 1A and FIG. 1B, in at least one embodiment, the single-use bioreactor includes an agitation system comprising at least one impeller internal to the bioprocess container and configured to effectuate a controlled mechanical mixing of the contents of the bioprocess container. The operation of the agitation system is controlled by the controller, shown in FIG. 36. In one embodiment of the disclosure, the impeller can be magnetically coupled to the motor.

In one embodiment, shown in FIG. 1A and FIG. 1B, the impeller(s) 6 and 7 can extend from an impeller shaft 8. The impeller shaft is operatively coupled 30 to an impeller motor 170, which may be exterior to the bioprocess container; the motor 170 can provide rotational force to the impeller(s) 6 and 7 via the impeller shaft 8. In at least one embodiment, the impeller shaft 8 extends exterior to the bioprocess container to couple with the impeller motor via an impeller port 30. In one embodiment, the impeller motor 170 may also be held in place by an arm coupled to the upper portion of the shell such that the motor is positioned centrally above the top of the shell 110. In some embodiments, the impeller comprises a multi-impeller, such as dual-impeller 6 and 7, centrally positioned internal to the single-use bioreactor. As shown in FIG. 1A, the multi-impeller can include a lower impeller and an upper impeller, along with optional middle impeller(s), each operatively coupled to and spaced along the rotatable impeller shaft 8. When scaling single-use bioreactors, the impeller(s) may be sized or spaced long the shaft such that an aspect ratio or distance between impellers or the like is maintained even as the scale varies.

The use of a dual impeller system as shown in FIG. 1B may provide numerous advantages and benefits depending upon the volume of the bioreactor container and the type of biological materials being processed or grown in the bioreactor. For example, the use of dual impellers can ensure a homogeneous environment with respect to process parameters such as pH, dissolved oxygen tension, dissolved carbon dioxide, and temperature. The dual impellers can work in conjunction to also blend nutrient feeds within the bioreactor. The use of two impellers can ultimately provide the necessary physiochemical environment for optimal cell growth, product accumulation and product quality.

In one embodiment, the top impeller and bottom impeller are both formed from a polymer material. The polymer material, for instance, can comprise a hydrophilic material or can be modified so as to be rendered hydrophilic. The use of hydrophilic polymeric materials, for instance, can provide various advantages and benefits in comparison to conventional materials, such as stainless steel. For example, the impellers can be made from a polymer material and have a lighter mass and better wettability properties than many conventional materials. In this manner, the top and bottom impellers can work in conjunction to provide rapid mixing, maintain homogeneity, maintain the biological material in suspension, and provide optimum gas dispersion. Of particular advantage, the impellers can accomplish all of the above goals while minimizing cell damage during rotation. For example, it is believed that the hydrophilic properties of the impeller and/or lower mass of the impeller can provide sufficient blending within the bioprocess container while doing so in a gentle manner that preserves the biological material thereby maximizing production. In fact, in some applications, the use of impellers made from a hydrophilic polymer material may increase processing times due to the conditions maintained in the bioprocess container in conjunction with the improved wettability of the impellers and the gentle nature of the impellers.

For example, the hydrophilic, polymer impellers can provide optimal hydrodynamic characteristics in terms of bulk mixing, gas dispersion and low shear. The biological material, such as mammalian cells, are kept in a homogeneous suspension through agitation by the impeller system that maximizes cell growth and minimizes cell damage.

In general, the one or more impellers can be made from any suitable polymer material that is biocompatible. The polymer material, for instance, may comprise a polyolefin, such as a polyethylene, a polypropylene, or copolymers thereof. The polymer can be rendered hydrophilic through various different types of treatment. For instance, in one embodiment, the polymer can be subjected to irradiation, photo or plasma induction, or oxidation. The polymer material can also be sterilized prior to use using any suitable technique or method. In one embodiment, for instance, the polymer material may be subjected to gamma irradiation. In still other embodiments, the polymer material may be subjected to corona discharge.

The impeller spacing on the shaft can vary depending upon the particular application. In one embodiment, for instance, the top impeller is spaced from the bottom impeller a distance that is equal to from 1× the diameter of the bottom impeller to about 2× the diameter of the bottom impeller. For instance, the space between the two impellers can be from about 1.2× the diameter of the bottom impeller to about 2× the diameter of the bottom impeller.

The liquid height above the upper impeller can be generally from about 0.3× the diameter of the top impeller to about 2.5× the diameter of the top impeller. In one embodiment, for instance, the liquid height above the upper impeller is from about 0.5× the diameter of the top impeller to about 1.8× the diameter of the top impeller.

The bottom clearance is the clearance between the bottom of the bioprocess container and the center line of the bottom impeller. In one embodiment, the bottom clearance is from about 0.3× the diameter of the bottom impeller to about 1.5× the diameter of the bottom impeller, such as from about 0.4× the diameter of the bottom impeller to about 0.75× the diameter of the bottom impeller.

In one embodiment, the impeller shaft 8 is integrated internal to the bioprocess container, such that the impeller shaft 8 is inside the bioprocess container. For example, in one embodiment, the shaft 8 may be initially provided internal to the bioprocess container and then, as the bioprocess container is established within the bioreactor shell, coupled with the impeller motor. The shaft 8 may be further gamma irradiated so as to accommodate the sterile environment for growing cell cultures within the bioprocess container. In an alternate embodiment, the impeller shaft 8 is initially provided external to the bioprocess container and then coupled to the bioprocess container as the container is established within the bioreactor shell.

Figure 37:
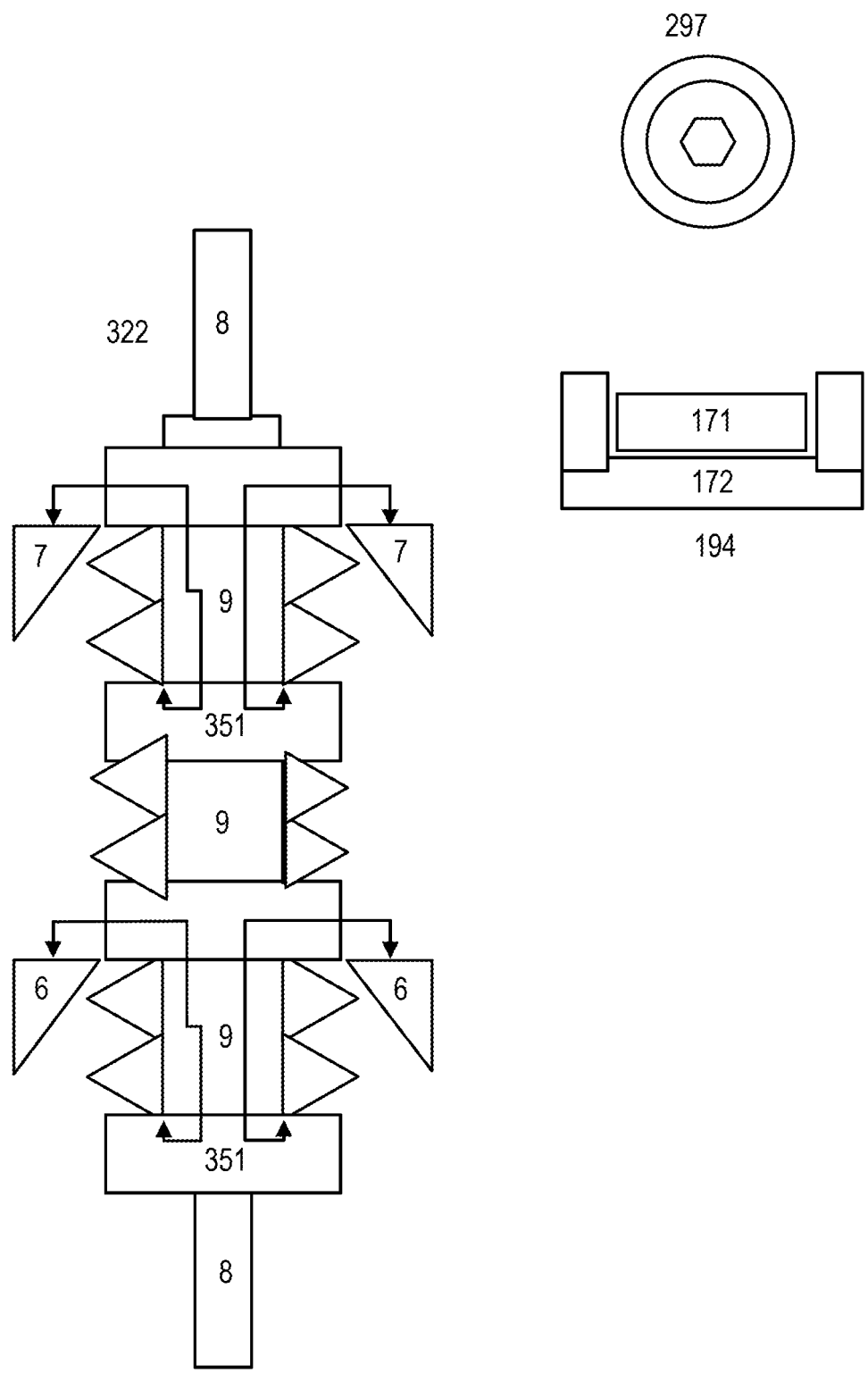
FIG. 37 shows a hollow impeller shaft configuration 322 for the single-use bioreactor. Impeller shaft sleeve 8 is hollow and has collapsible agitators 6 and 7 linked to rings 351 connected to collapsible baffles 9. A metal rod is inserted through the middle of the shaft sleeve 8. In one embodiment, the metal rod may be provided in sections that can be screwed together or otherwise assembled before insertion through the shaft sleeve. The last section 194 of the metal rod has a magnetic top 172 to connect to the motor, which may also have a magnet 171. In one embodiment, as the metal rod gets pushed farther into the shaft sleeve 8, the rings 351 connected to the agitators 6 and 7 get pulled down as the baffles 9 stretch out, thus lifting up parts of the agitators 6 and 7. The baffles may click into place with clips or the like. The first section 297 of the metal rod can be pushed into a hole or otherwise attached to the bottom of the bioprocess container or attached or pushed into a component of the bioprocess container. In one embodiment, the first section 297 of the metal rod has a shaped portion that can be pushed into a hole having a corresponding shape (e.g. a hexagonal portion may be pushed or otherwise attached to a hexagonal hole) in the bottom of the bioprocess container or a component thereof. In one embodiment, the metal rod rests on or in or is otherwise attached to a sparger ring. In a further embodiment, the metal rod may be pushed into a hole on a disc in the center of the sparger ring. In an even further embodiment, the disc may have a built-in magnet to ensure movement. In one embodiment, the entire hollow impeller shaft configuration 322 or portions thereof may be collapsible.

In some embodiments, the impeller shaft 8 is compressible (e.g., foldable or nestable) internal to the bioprocess container so as to reduce the size of the bioprocess container and facilitate storage and transport thereof. In one embodiment, the agitator, the impeller(s) and/or blade elements(s) may be collapsible onto or foldable towards the rotating shaft or onto another element of the mixing system. As shown in FIG. 37, baffle elements 9, which may be collapsible, may project from a hollow rotating shaft 8. In one embodiment, a rod, such as a metal or plastic rod, is inserted through the middle of the shaft sleeve 8, thus stretching the baffles and lifting up parts of the agitators 6 and 7. The baffles may click into place with clips or the like. The first section 297 of the metal rod can be pushed into a hole or otherwise attached to the bottom of the bioprocess container or attached or pushed into a component of the bioprocess container, such as a sparger ring. In one embodiment, the entire hollow impeller shaft configuration 322 or portions thereof may be collapsible. In one embodiment, the components of the hollow agitator may be made from a polymeric material, such as a hydrophilic polymer.

The agitation system may be constructed from any suitable material and in any suitable manner, including 3-D printing. In one embodiment, the materials of construction of the agitation system are chosen such that the system has enough mechanical strength to be able to support a power dissipation of at least 100 W/m$^3$ in normal operation. In one embodiment, the impeller has a scalable geometry in accordance with U.S. Provisional Application No. 62/354,216 and U.S. Publication No. 2011-0312087, the entire contents of which are hereby incorporated by reference. In at least one embodiment, the impeller shaft 8 and impeller motor 170 each includes a corresponding coupler such that the impeller shaft 8 may be coupled to the impeller motor to effectuate operation of the single-use bioreactor, and may be decoupled from the impeller motor so as to enable removal of the single-use bioreactor bioprocess container. The corresponding couplers are preferably magnetic couplers.

Non-limiting examples of impellers suitable for use in the agitation system of the present disclosure include hydrofoil impellers, high-solidity pitch-blade impellers, high-solidity hydrofoil impellers, Rushton impellers, pitched-blade impellers, gentle marine-blade impellers, CelliGen cell-lift impeller, A320 Impeller, HE3 Impeller, and the like. Spin filters can also be used, such as when the device is operating in perfusion mode. In multi-impeller embodiments of the single-use bioreactor of the present disclosure, the impellers may comprise the same or different materials, designs, and methods of manufacture. For example, in one embodiment, the top impeller could be a hydrofoil impeller or one of like design, such as that made using a 3D printer. As another example, the bottom impeller could also be a hydrofoil impeller. Alternatively, other types of impellers contemplated by a multi impeller design include high solidarity pitch blade impellers, high solidarity hydrofoil impellers, axial hydrofoil impellers, and the like. In one embodiment, impellers suitable for use herein include those manufactured by 3-D printing to look like any of the impellers known in the art, even if the scale of the impellers is different.

In one embodiment, the top impeller can comprise a hydrofoil impeller. In this embodiment, the bottom can also comprise a hydrofoil impeller. Alternatively, the bottom impeller can comprise a pitch-blade impeller or a high-solidity hydrofoil impeller. For example, the bottom impeller can be designed particularly to dissipate gases being emitted from one or more spargers.

The agitation system may be configured to suspend any desired components contained within the bioprocess container. For example, in at least one embodiment, the agitation system is configured to suspend non-clumping mammalian cell lines. The single-use bioreactors of the present disclosure can use any number of impellers to facilitate a homogenous or semi-homogeneous environment with respect to process parameters such as pH, dissolved oxygen tension (DOT) and temperature, thus maintaining a well-mixed cell suspension and blending nutrient feeds within the single-use bioreactor.

The agitation system may be further configured to reach desired stir speeds or mixing times. For example, in at least one embodiment, the agitation system is configured to support a mixing time of less than 70 seconds at a fill volume of approximately 1100 liters. In one embodiment, as shown in FIGS. 1A and 1B, the agitation system may include at least one tachometer 242. The tachometer may be configured for monitoring a rotational speed of the rotatable shaft coupled to the at least one agitator and/or may be configured to measure the stir speed of the agitator, such as an impeller, during operation of the SUB. The tachometer may be in communication with the controller and may be further configured to provide the measured stir speed to the controller so as to effectuate a control feedback loop. In one embodiment, the controller may be configured to control the motor in a manner that rotates the shaft at a predetermined speed. In one embodiment, agitation speed can be measured and controlled via inputs from a calibrated tachometer. In a further embodiment, the controller may display the current agitation rate and control the motor speed to achieve the process set point. In one embodiment, the impeller may effectuate a stir rate of greater than 0 rounds per mind (rpm), such as greater than 50 rpm, such as greater than 100 rpm, such as greater than 200 rpm, such as greater than 500 rpm, such as greater than 1,000 rpm. In one particular embodiment, the impeller may be controlled to effectuate a constant stir speed of +/−1 rpm in a 50 to 200 rpm range. In one particular embodiment, the agitation rate of 0 to 80±1 rpm can be used as an operational range. In another particular multi-impeller embodiment, the agitation rate of the at least two impellers may be 200 rpm or may be at most 165 rpm. However, the agitation rate of the at least two impellers is dependent on the scale; as such, the impeller may be controlled to effectuate much higher or much lower stir speeds. Stir speed set points may be provided as a stir speed band such that corrective action is taken when the measured stir speed is outside the stir speed band. Stir speed set points may also be controlled by a cascade control system based on dissolved oxygen concentration, $CO_2$ concentration, pH, or any combination thereof. For example, in one particular embodiment, when $dO_2$ or the like is being controlled at a set point and the gas flow reaches a set rate, the stir speed may be increased instead of gas flow to reach a set point.

In some embodiments, power dissipation into the bioreactor and Reynolds number may need to be sufficiently high to maintain a turbulent (loaded) regime. Therefore the selection of impeller diameter can be a compromise between choosing a large enough diameter to ensure adequate homogeneous mixing without exceeding the hydrodynamic characteristics of the bioreactor. These hydrodynamic characteristics include throttling axial flow, insufficient power dissipation, exceeding upper limits of impeller tip speed and creation of poorly mixed laminar zone. In one non-limiting embodiment, the diameter for the axial flow impellers may be less than 0.5×T so as to avoid disruption in axial flow and poor agitation and aeration.

In one embodiment, the agitation set point can be controlled based on readings from the primary dissolved oxygen tension (DOT) probe and the spectroscopic probe. In some embodiments, maintaining DOT may take priority. Once a diameter is selected, then maintaining constant D/T ratio is critical between scale down pilot vessels in order to maintain the central assumption of scale studies—that of maintaining geometric similarity. For one exemplary embodiment, the $k_L a$ scale up correlation at 12.2 liter has been determined for the four impellers at the D/T ratios shown in Example 4. From a geometric similarity standpoint, in certain embodiments A310 diameter of 1.229 m (D/T of 0.44) and A315 diameter of 1.285 m (D/T of 0.46) may be recommended. However, in certain embodiments, a manway diameter can restrict the largest impeller diameter that can be installed and removed to 1.219 m. Therefore, in some particular embodiments, A310 and A315 to be 1.219 m diameter can be used, thereby keeping with ease of impeller installation and removal and maintaining close to the geometric similarity proposed in scale down study.

Baffles 9

The single-use bioreactor of the present disclosure may further comprise at least one baffle. A baffle is a vertical plate used to prevent the formation of a funnel or vortex. Referring to FIG. 1A and FIG. 1B, in at least one embodiment, the single-use bioreactor includes a baffle system (9) comprising at least one baffle configured to break up or otherwise substantially prevent the formation of vortices within the single-use bioreactor during operation, and to reduce laminar flow. The single-use bioreactor of the present disclosure may comprise at least one baffle, such as at least two baffles, such as at least three baffles, such as at least four baffles, such as at least five baffles, such as at least six baffles.

The baffles may be located on or in or be formed from the shell or the bioprocess container at any suitable location and in any suitable arrangement. In one embodiment, the baffle may be configured to extend adjacent to the side wall of the bioprocess container in a longitudinal directional. As such, in some embodiments, the baffles, in one embodiment, are longitudinally positioned in even or uneven spaced apart orientation along an interior surface of the shell or the bioprocess container and may project radially therefrom towards the center of the shell or the bioprocess container, thereby essentially forming a substantially ribbed interior surface. As unanticipated by previous designs, the use of baffles longitudinally position along the entire or partial length of the bioprocess container or shell helps ensure that deflected axial flows are generated and re-enforced along the entire length of the baffle; consequently, axial deflected flows uniform in strength and energy can be obtained from baffled single use bioreactors at low agitation rates.

Figure 5:
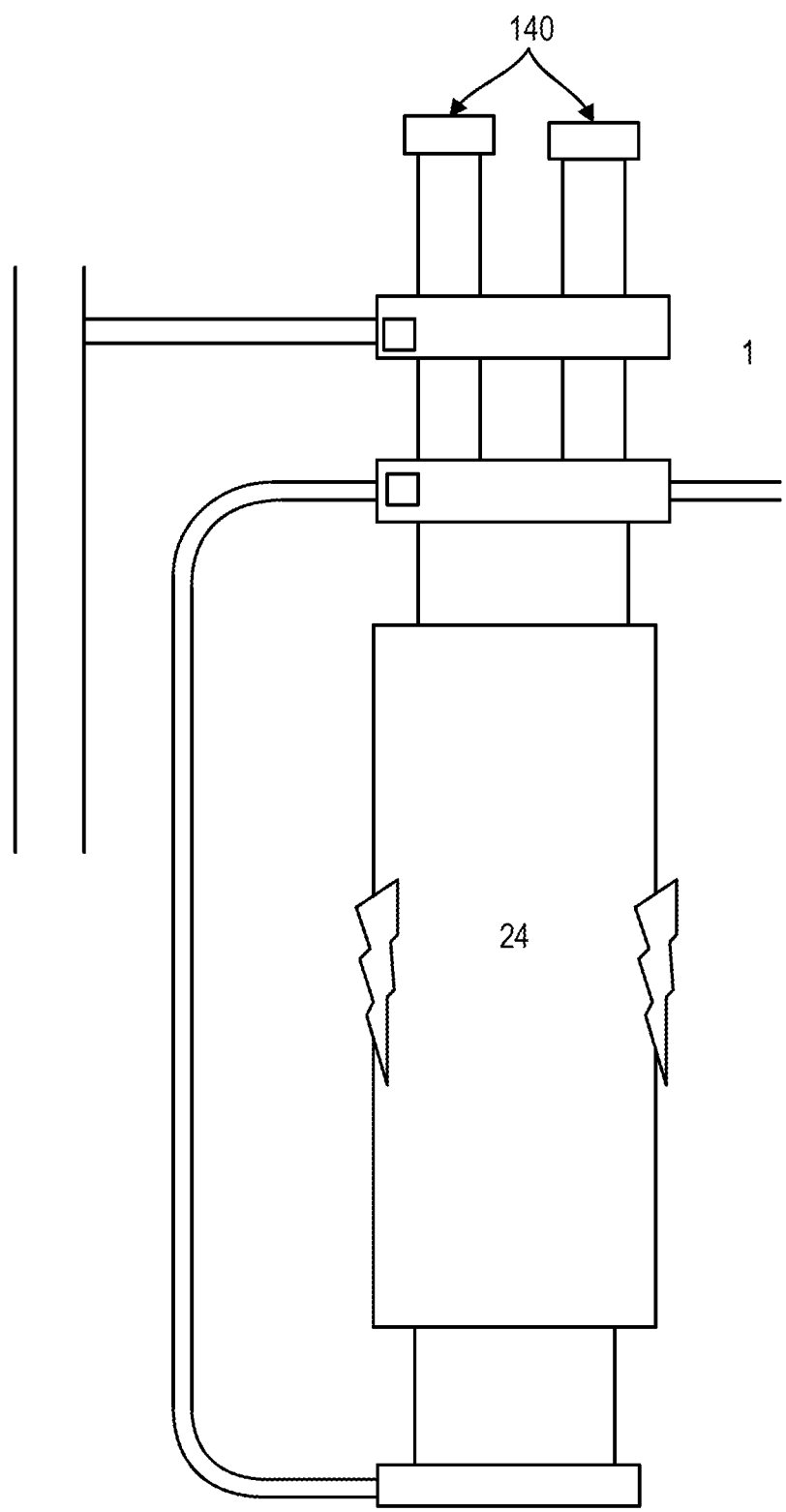
FIG. 5 shows a flexible baffle 24 according to an embodiment of the disclosure. The baffle is connected top and bottom to the bioreactor vessel 1 and tightened by tightening a pair of mechanical screws 140 at the top of the vessel 1.

In one embodiment, the baffle is configured to be placed outside the hollow enclosure of the bioprocess container. For example, in one embodiment, the baffle may be attached to or be integrally formed from the interior surface of the shell. Before, during, and/or after operation of the single use bioreactor, the side of the bioprocess container may conform around and/or be fitted to the shape of the baffle. As such, in at least some embodiments, the flexible bioprocess container bends or otherwise conforms itself around the substantially ribbed interior surface of the bioreactor shell. In an alternative embodiment, the baffle may be configured to be placed inside or be integrally formed from the hollow enclosure of the bioprocess container. In some embodiments, the baffles may be configured such that they can hook into holes or openings, such as via a hook-and-slot fastener, on the bioprocess container or shell interior. In this manner, the baffles may be removable and exchangeable for baffles having different characteristics. As shown in FIG. 5, a flexible baffle 24 can be connected top and bottom to the vessel 1 and tightened by tightening a pair of mechanical screws 140 at the top of the vessel 1.

In some embodiments, the baffles are capable of being inflated and/or deflated. Thus, in one embodiment, the baffle defines an inflatable fluid bladder. Said baffle can be incorporated into the flexible bioprocess container, or, in some embodiments, may be incorporated onto the shell. The baffle may become frigid via tension or air pressure, allowing for incorporation of a frigid baffle into a flexible bioprocess container that needs to be folded for storage. In some embodiments, the baffle may be inflated before incorporation with the bioprocess container or shell. In other embodiments, the baffle will be incorporated with the bioprocess container or shell prior to inflation. In certain embodiments, the baffles may be configured such that upon connection to the shell and/or the bioprocess container via mechanical screws, the tension created by the screw may in effect "inflate" the baffle.

The at least one baffle of the present disclosure may be formed from any suitable material. For example, in one embodiment, the baffle is made from a flexible polymer film.

The baffles of the present disclosure may assume any suitable shape. In one embodiment, the at least one baffle has a shape that extends radially inward from the side wall of the bioprocess container an amount sufficient to affect fluid flow in the hollow enclosure during mixing of a culture media by the mixing device. In operation, the baffle system has a scalable geometry in accordance with the scalable geometries described in U.S. Publication No. 2011-0312087, the entire contents of which are hereby incorporated by reference. In one embodiment, the baffles may comprise straight or curved plates with rounded edges.

In at least one embodiment, one or more of the baffles comprises a split-baffle comprising a top-baffle and a bottom-baffle corresponding to the upper portion and the lower portion of the shell. In one embodiment, the split-baffle may be divided into more than two portions, such as into thirds or quarters. As shown in FIG. 10, on the inside of the shell there can be four baffles 9, to avoid a vortex being created when motor is operation. Each of these can be spilt into two halves, top and bottom. These baffles can then be hung onto hooks and slotted into place.

The thickness of the baffle(s) is not limited, but, in some embodiments, the thickness may be selected in order to ensure rigidity to the radial component of the fluid flow. In further embodiments, the rigidity of the radial component of the fluid may be ensured using tension or air pressure. Additionally, in some embodiments, thickness is chosen to ensure the baffle plates are not damaged during gamma irradiation, thereby affecting the baffle to tank wall clearance. In one particular embodiment, the bioreactor of the present disclosure may comprise four equally spaced baffles that are $0.1 \times T$ or 279 mm wide $1.1 \times H-H_h$ or 3882 mm tall and have a baffle to shell wall clearance, $W_c$ of $0.01 \times T$ or 28 mm. The baffles may have a diameter less than 20%, such as less than 15%, such as less than 10%, such as less than 5%, such as less than 3% of the shell and/or bioprocess container diameter to reduce laminar flow in the culture. As such, in one embodiment, the at least one baffle may extend radially inward towards the shell and/or bioprocess container a distance of from about 1% to about 25%, such as from about 3% to about 20%, such as from about 5% to about 15%, of the diameter of the bioprocess container and/or the bioreactor shell.

Ports 20, 21, 180

The single-use bioreactor according to the present disclosure may also have at least one inlet and/or outlet port for feeding or removing materials from the hollow enclosure of the bioprocess container. The single-use bioreactor may have ports via which tubing or other accessories may extend into and out of the single use bioreactor environment. In particular, the bioprocess container may include at least one port, having a first end and a second end, for connecting to at least one supply/feed line. In a further embodiment, the bioprocess container may include a plurality of ports for connecting a plurality of supply lines for feeding materials such as fluid to the bioprocess container. The ports may comprise connectors for forming attachments to supply lines. In some embodiments, some of the connectors and lines may be incompatible; as such, in certain embodiments, the limited compatibility of the connectors and lines may ensure proper connection of the desired lines and ports. In additional embodiments, smart tubing connections may be used, which may involve electronic verification of the correctness of the tubing connections. At least one of the supply lines, in certain embodiments, may include a fluid filter positioned either upstream or downstream from its corresponding port. In at least one embodiment, the single use bioreactor includes at least one sample port.

The single-use bioreactor may comprise any number of supply/feed lines for feeding fluids to the bioprocess container. In some embodiments, at least one of the supply lines may include a fluid filter, such as an inline filter. The single-use bioreactor may also comprise any number of ports, such as at least one port, such as at least two ports, such as at least three ports, such as at least four ports, such as at least five ports, such as at least six ports, such as at least seven ports. In one embodiment, the ports used in the current disclosure may have scalable geometries. The ports may permit materials to move in or out of the ports in one or two directions. For example, in one embodiment, an outlet port may only permit fluid to flow out of the outlet. In certain embodiments, the ports may be associated with control devices that may regulate material movement. In one embodiment, the control device may be a one-way or non-return valve. In some embodiments, each port may have only one corresponding supply line. In other embodiments, each port may have multiple corresponding supply lines.

In certain embodiments, each port and each corresponding supply line include matching indicators, including but not limited to tags and/or shape and/or color coding. These matching indicators may be used for assisting a use in connecting the at least one supply line to its respective port. In one particular embodiment, the matching indicators comprise color such that each port and corresponding supply line are color coded. The ports, in certain embodiments, may comprise universal connectors. In one embodiment, the first end of the port forms a reconnectable attachment to a respective supply line.

Figure 3:
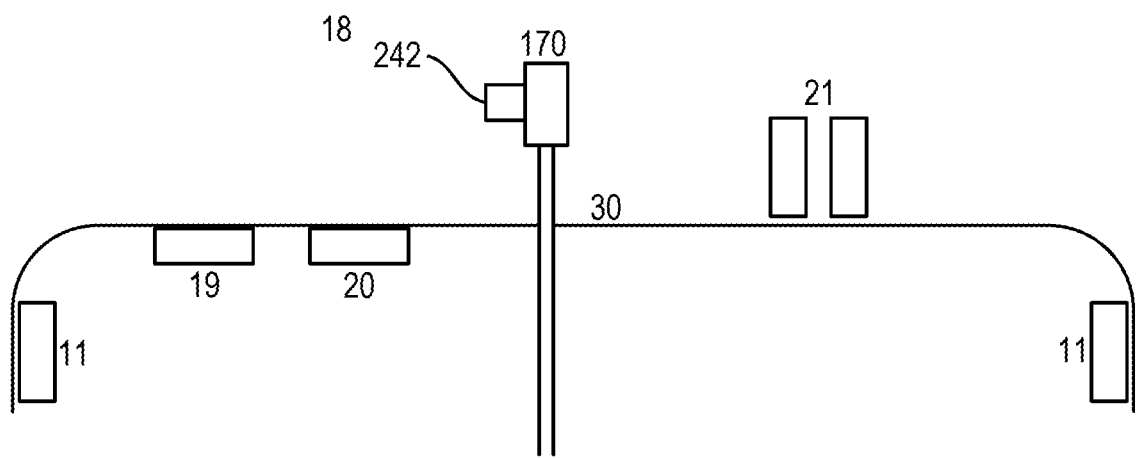
FIG. 3 shows a view of the top of a single use bioreactor (SUB) vessel according to an embodiment of the disclosure.
Figure 7:
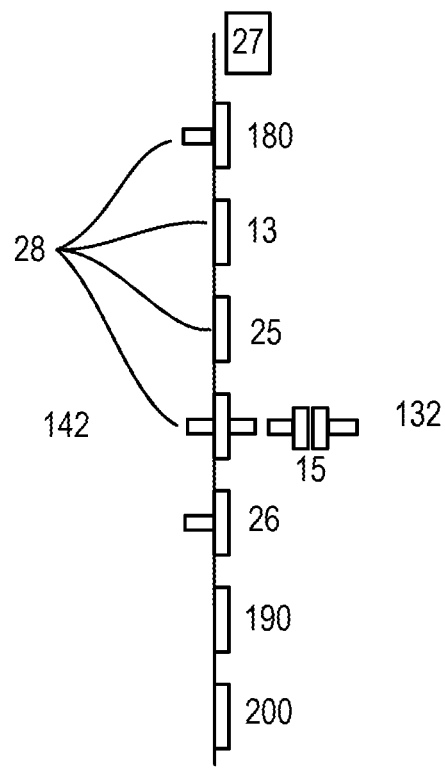
FIG. 7 shows the side view of a single use bioprocess container 100 according to an embodiment of the disclosure. 142 represents an inside of the bioprocess container, while 132 represents an outside of the bioprocess container. The bioprocess container 100 comes with single use probes 27 or ports for probes sterilized in situ with the bioprocess container or for sterilized probes to be inserted. The probes 27 are connected to a small wireless transmitter which communicates with the data logging system without wires reducing the potential for electrical interference and simplifying the arrangement of the system. The bioprocess container 100 includes sufficient probe ports 28 to allow use of triplicate probes for all measurements giving redundancy and ability to detect probe errors. For example, the bioprocess container 100 may include a temperature probe port 180, a single use dielectric spectroscopic probe 26, a single use noninvasive pH probe, a single use $pCO_2$ noninvasive probe 190 and a single use noninvasive DOT probe 200. The bioprocess container 100 also may include an optically clear spectroscopic window 13 (for noninvasive spectroscopic measurement of the cell culture) and tubes 15 into the vessel.

Referring to FIG. 3 and FIG. 7, in at least one embodiment, the bioprocess container includes several bioprocess container ports, via which supply lines, tubing or other accessories may extend into and out of the bioprocess container, and the shell includes one or more corresponding shell ports, via which the tubing or other accessories may extend into and out of the single use bioreactor environment through the shell. In one embodiment, the one or more shell ports may align with corresponding bioprocess container ports such that when the single use bioreactor is in operation, folding and/or creasing of the bioprocess container is minimized.

FIG. 3 shows a view of the top of a single use bioreactor (SUB) vessel according to an embodiment of the present disclosure, wherein 11 represents foam sensors, 19 represents a pressure sensor, 20 represents a sterile solids addition port, and 21 represents dual gas outlet ports. The bioprocess and shell ports of the present disclosure may be configured such that, in one embodiment, the tubing and other accessories of the bioreactor can be held in place by projections of the bioprocess container and the shell.

FIG. 7 shows a side view of a single use disposable bioprocess container 100 according to an embodiment of the disclosure. The bioprocess container 100 comes with single use probes 27 or windows for probes sterilized in situ with the bioprocess container. The disposable bioprocess container 100 includes sufficient probe ports 28 to allow use of triplicate probes for all measurements giving redundancy and ability to detect probe errors. For example, the disposable bioprocess container 100 may include a temperature probe port 180, a single use dielectric spectroscopic probe 26, a single use pCO$_2$ noninvasive probe 190 and a single use noninvasive DOT probe 200. The disposable bioprocess container 100 also may include an optically clear spectroscopic window 13, to allow noninvasive spectroscopic measurement of the cell culture, and tubes 15 into the vessel.

In at least one embodiment, the single use bioreactor includes at least one subsurface port for discharging fluid at or below the fill level of the bioprocess container contents. For example, the single use bioreactor may comprise, in one embodiment, at least one feed line for feeding/supplying fluids into the bioprocess container, wherein the feed line extends into the hollow enclosure of the bioprocess container. The feed line may include a subsurface fluid outlet which may be positioned at any suitable location within the hollow enclosure, such as adjacent the agitator. In embodiments wherein the agitator forms a circumference when rotated, the supersurface fluid discharge of the feed line may be positioned above the circumference of the agitator such that fluids flowing through the fluid discharge contact the culture media with the circumference of the agitator. In some embodiments, the fluid outlet may be associated with a fluid control device that regulates fluid flow. For example, the fluid control device may only permit fluid to flow out of the fluid outlet and may prevent fluid flow in an opposite direction. In one embodiment, the fluid control device may comprise a one-way valve.

In at least one embodiment, the single use bioreactor includes one or more super-surface ports that discharge at or above the fill level of the bioprocess container contents. Furthermore, in at least one embodiment, the single use bioreactor includes at least one super-surface port that discharges substantially at or adjacent to a longitudinal axis region of the single use bioreactor. In one example, the single use bioreactor comprises at least one feed line, positioned at the top of the bioprocess container, wherein the feed line includes a supersurface fluid discharge positioned above a volume of culture media residing in the bioprocess container. The supersurface fluid discharge may be located and/or configured such that a fluid flowing through the fluid discharge makes direct contact with a culture media contained within the bioprocess container. In one embodiment, the super-surface port may further comprise a discharge nipple or funnel, wherein the nipple or funnel releases material such that it does not run down the sides of the bioprocess container.

Referring to FIGS. 1A, 1B, and 7, in at least one embodiment, the single use bioreactor includes a harvest control system. The harvest control system can comprise at least one harvest port and corresponding harvest pump coupled via harvest tubing. Each corresponding port, pump and tubing combination may form a harvest line. In one embodiment, the operation of the temperature control system is controlled by the controller. In one embodiment, the harvest port may have a shape configured to induce a vortex flow of fluids from the bioprocess container. In an alternate embodiment, an additional device may be attached to the harvest port in order to induce a vortex flow of fluids. The harvest port, tubing, and pump may be of any suitable configuration. In one embodiment, the harvest port may have a diameter or cross-sectional area proportional to the volume of culture media held in the hollow enclosure of the bioprocess container. In another embodiment, the internal diameter of the harvest line and/or port may be modified to match the flow rate at which the medium is to be harvested. In one embodiment, the design of these harvest line ports may use re-enforced or braided tubing to prevent tube collapsing under the suction head of the pump during high flow rate applications.

In at least one embodiment, the optional top cover of the shell includes one or more cover ports, via which the tubing or other accessories may extend into and out of the single use bioreactor environment through the cover. In one embodiment, the one or more cover ports may align with corresponding bioprocess reactor ports such that when the single use bioreactor is in operation, folding and/or creasing of the single use bioreactor is minimized. In at least one embodiment, the cover ports are bisected such that they separate to permit access to and manipulation of the tubing and/or accessories held therein. In at least one embodiment, the cover ports are bisected in-line with the hinge joint of the cover. In some embodiments, the cover includes at least one ports, such as at least two ports, such as at least three ports, such as at least four ports, such as at least five ports.

In one embodiment, the single use bioreactor has at least one, such as at least two ports for alkali addition 20, as shown in FIG. 1A and FIG. 1B. In one particular embodiment, the bioreactor may have two ports for alkali addition, wherein the first port is located at the central line of the bottom impeller and the second port is located at the central line of the top impeller. The pH probes, in one embodiment, may be located diametrically opposite the alkali addition points into the bioreactor.

In at least one embodiment, the single use bioreactor includes one or more subsurface ports that discharge below the fill level of the bioprocess container contents. Moreover, in at least one embodiment, the single use bioreactor includes two subsurface ports that discharge in an impeller region. By designing feeding ports with an internal feed line which is routed within the bioreactor to allow discharge directly into the strongly flowing zone around the impellers, formation of environmental micro-zones can be surprisingly prevented. The prevention and minimization of these micro-zone leads to a rapid return to homogeneity following feed additions and has greatest benefits, especially at larger scales of operation. The formation of micro-zones of non-physiological environment can also be further reduced by selecting appropriate feed line internal diameters to match the expected feed bolus volume applied or to match the flow rate at which the feeds are applied. In one embodiment, the design of these feed line ports may use re-enforced or braided tubing to prevent tube collapsing under the suction head of the pump during high flow rate applications.

The ports may have any suitable diameter. In one embodiment, the diameter may be based on the bioreactor scale. For example, in one particular embodiment, the harvest port has a 1-inch inner diameter.

Sparger 5

Figure 2:
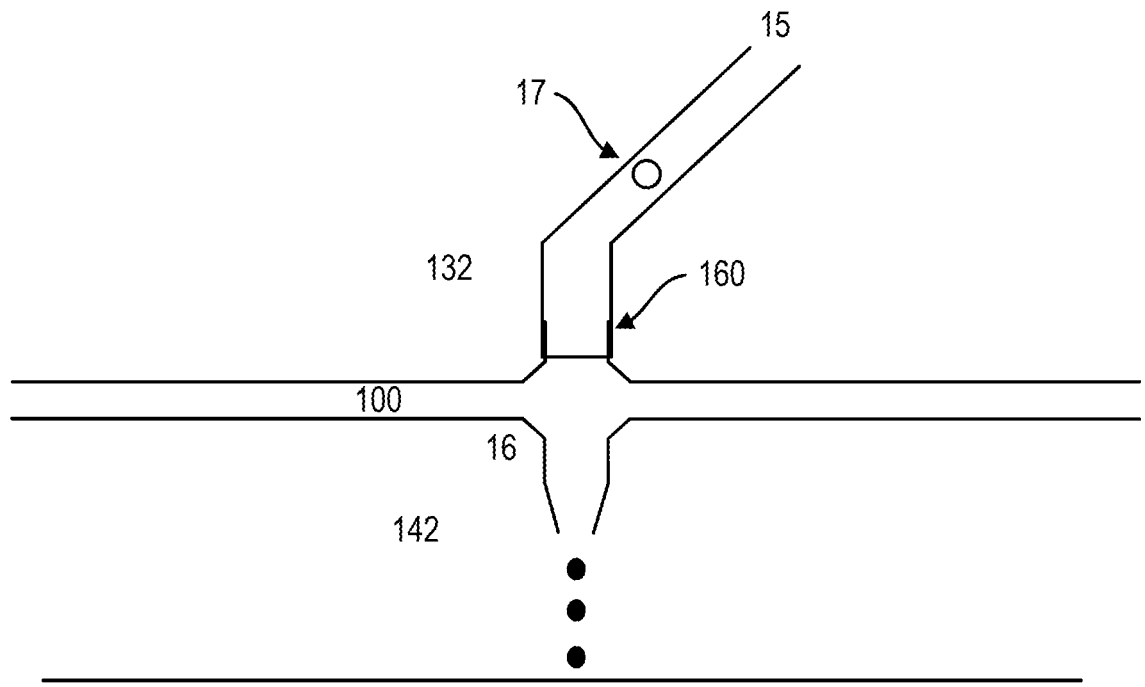
FIG. 2 shows a close-up view of the tubing connector 160, which in one embodiment may be a smart connector 160, connecting the feedline 16 and tube 15 according to an embodiment of the disclosure. Inline sterile filter(s) 17 may also be present. 100 is the bioprocess container, with 132 representing the environment outside of the bioprocess container and 142 representing the environment inside the bioprocess container.

As shown in FIG. 1A and FIG. 2B, the single-use bioreactor according to the present disclosure may comprise at least one sparger 5. In some embodiments, the single-use bioreactor comprises two or more spargers 5. In one embodiment, one of the spargers may be a ballast sparger. The sparger may comprise a gas tube having a longitudinal and a lateral portion. The longitudinal portion may extend vertically into the hollow enclosure of the bioprocess container. The lateral portion may be located at an end of the longitudinal portion below the agitator. The lateral portion may define a plurality of holes for releasing a gas into a culture media contained within the bioprocess container. In some embodiments, the single use bioreactor comprises at least one ballast sparger and at least one second sparger. The ballast sparger defines a first plurality of holes for releasing a gas into a culture media, while the second sparger defines a second plurality of holes for releasing a gas into the culture media. The second plurality of holes may have the same or a different diameter and/or number of holes than the first plurality of holes. For example, in one embodiment, the second plurality of holes may have a smaller diameter than the first plurality of holes.

In another embodiment of the present disclosure, there may be a separate sparger port for the installation of the ballast sparger. Advantages to adding ballast from a separate sparger can be for one or more of at least three reasons: (i) it prevents dilution of oxygen or oxygen enriched DOT demand gas with the ballast gas, which can, in some embodiments, ensure the best OTR, as the oxygen concentration gradient of the bubbles emerging from the sparger is greatest; (ii) it can allow ballast sparger to be located at a different position from DOT control sparger to avoid impacting DOT control on delivering desired ballast for $pCO_2$ control; and (iii) the ballast sparger can be independently designed from the DOT control sparger. However, in certain embodiments, it may be desirable to use the same sparger port for the ballast sparger and the at least one other sparger.

In one embodiment, sparger geometry may be selected in order to distribute the desired number of holes in the desired manner and/or for the desired sanitary design.

In one embodiment, the calculation of hole size and number of holes can be iterated until the target Reynold's number, Re of gas emerging from holes, such as <2000, is reached and the target Sauter mean diameter for a bubble, such as 10-20 mm during chain bubble regime, is reached. In certain embodiments, the location of probe ports, sample valve and addition points can be considered together to avoid transitory spikes. Furthermore, in certain embodiments, the position of the sample valve with respect to controlling probes can be configured to permit accurate estimation of off-line verification of the measured process parameter.

The spargers may be located in any suitable location in the bioreactor vessel. In one embodiment, the distal end of the sparger may be preferably positioned below the impeller (or the bottom most impeller in the multiple impeller case) so as to vent the pumped gas into the area swept by the impeller.

In at least one embodiment, the single use bioreactor includes an aeration system comprising at least one of a sparger system and a gas overlay system. The aeration system is configured to supply oxygen and other gasses to cell culture during operation of the single use bioreactor. In one embodiment, the operation of the aeration system is controlled by the controller.

In one embodiment, the gasses can be introduced to the single use bioreactor at the same or different times via the sparger system and gas overlay. In one non-limiting embodiment, the gasses may include oxygen, nitrogen, carbon dioxide, and compressed air. In one embodiment, the aeration system may include mass flow controllers sized based on the mass transfer capabilities of the sub system in order to enable process control. In one embodiment, the number of mass flow controllers is sufficient to enable independent control of from at least one to all of the gasses to a main sparger, air to the headspace gas overlay and at least one of any of the four gasses to a second sparger. In one embodiment, each of the above gas supplies can be implemented as independent flows and may be capable of total shut-off when not required for the process. In one embodiment, in operation, gas flow rate set points are provided as a gas flow rate band such that corrective action can be taken when the measured gas flow rate is outside the gas flow rate band. In one embodiment, the sparger system and gas overlay system are each configured so as to support a desired total gas flow rates of any VVM, such as, in one particular embodiment, 150 L/min.

In one embodiment, the sparger system can include at least one sparger internal to the single use bioreactor and coupled to a gas inlet of the single use bioreactor so as to receive gas from an mass flow controller exterior to the single use bioreactor. The sparger may comprise an elongated sparge tube having a plurality of sparger holes of any desired diameter at its distal end. In one embodiment, the sparger system may include two spargers and associated accessories. In one particular embodiment, the sparger system can generate gas bubbles with a Sauters mean bubble diameter of 11 mm in 1 g/L pluronic and a Reynolds number of the gas emerging from the sparge holes of less than 2000 at maximum anticipated gas flow rate. The sparger system can also be configured such that at a desired NLPM a desired mean bubble diameter and Reynolds number is achieved. In some embodiments, the sparge tube and/or the sparge system can have thirty 2 mm sparge holes.

Figure 6:
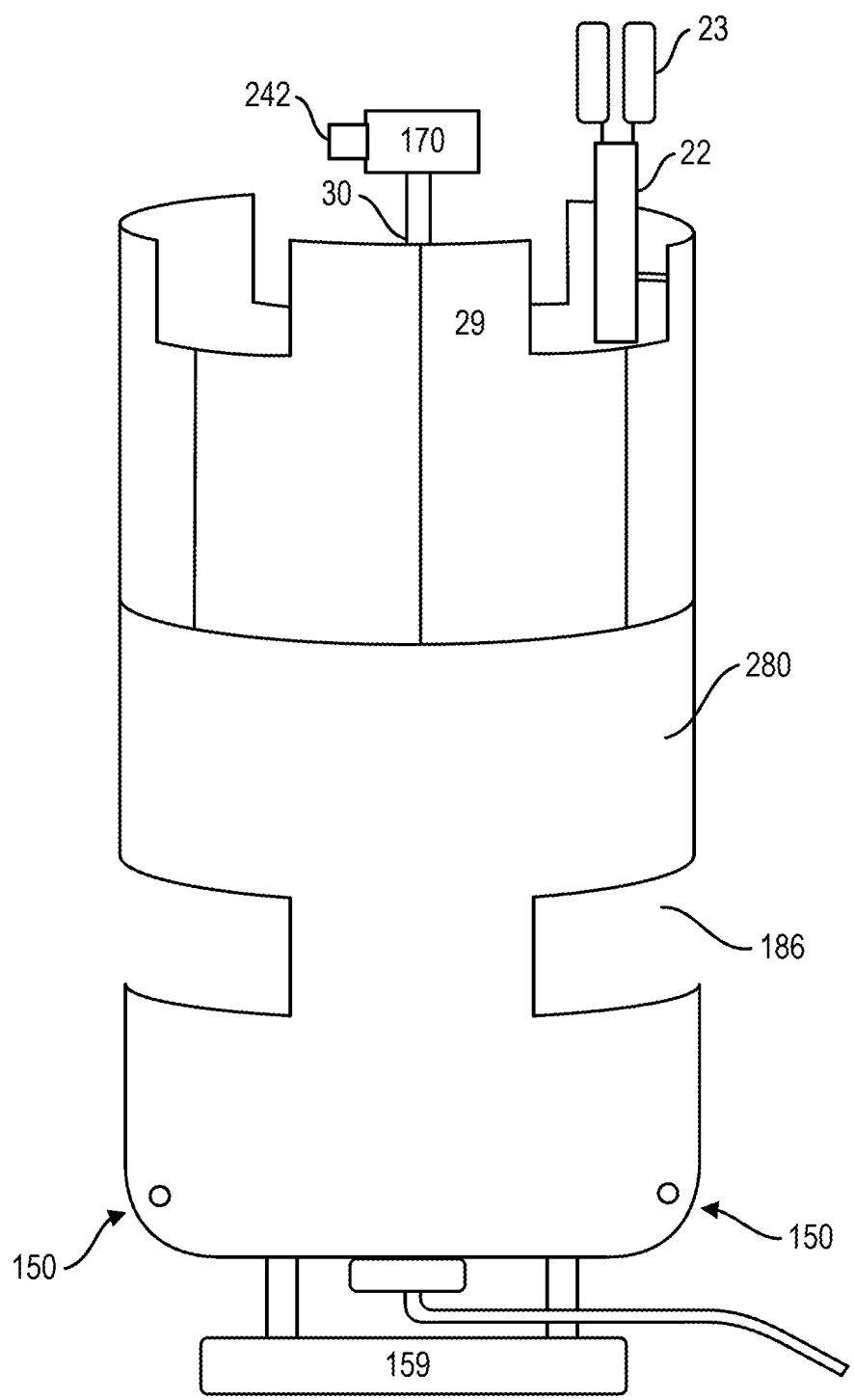
FIG. 6 shows a crenulated bioprocess container shell 29 according to an embodiment of the disclosure, which provides robust support to the items held above the bioprocess container including the motor 170, the condenser 22, and off gas filters 23. The shell 29 includes anchorage points 150 for baffles and open space 186 for probe belt. The shell 29 may further comprise a thermal jacket 280. 30 is the agitator shaft head.

In one embodiment, the gas overlay system may include a gas inlet extending from the headspace of the single use bioreactor, such as from the headspace of the shell or the bioprocess container, so as to receive gas from an mass flow controller exterior to the single use bioreactor, shell, and/or bioprocess container. In one embodiment, the gas inlet/outlet 230 may be a super-surface port. In one embodiment, as shown in FIG. 6 and FIG. 8, the gas inlets/outlets 230 of the sparger system and the gas overlay system may further include gas filters 23. In one embodiment, the valves on the gas outlets 230 could be automatic pinch valves, which may optionally be controlled by the control system described herein. In a further embodiment, the automatic pinch valves may be configured to enable switching to a backup gas outline line in situations in which the pressure inside the bioprocess container raises beyond an acceptable level. In certain embodiments, the gas outlets may be replaceable and/or interchangeable.

The aeration system may further comprise an exhaust gas outlet configured to release gas from the bioprocess container interior during operation via a gas exit line. In one embodiment, the gas outlet may be a super-surface port. The gas outlet may comprise a gas filter. The exhaust gas outlet may further include a bifurcating line going to mail and backup 10 inch filters. The gas outlet filters may also be fitted onto the top of the bioprocess container using reusable connections, so that these can replaced if required.

Figure 4:
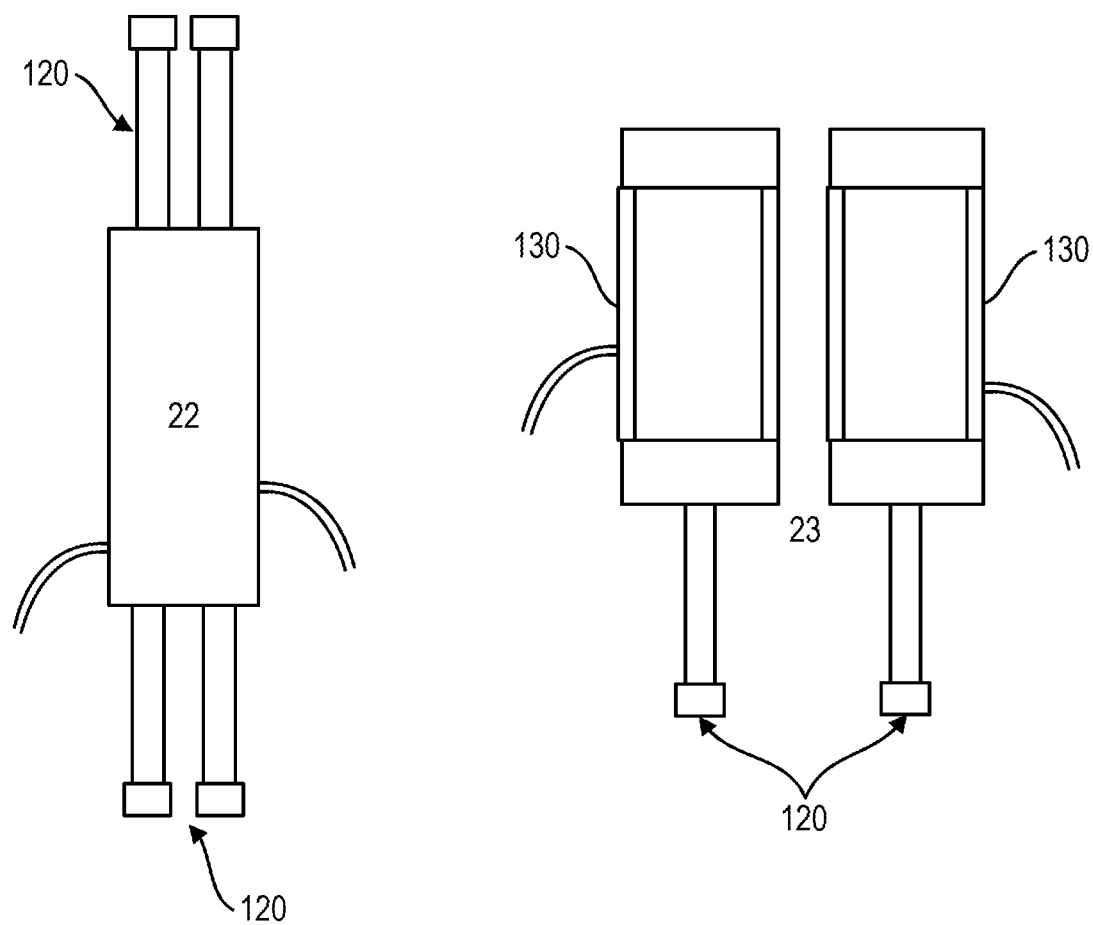
FIG. 4 shows the replaceable condenser 22 and dual replaceable pre-sterilized off gas filters 23 according to an embodiment of the disclosure. The off gas filters are capable of operation at 80° C. heated by external heater jacket 130. The filters can be replaced in case of blockage. 120 represent the re-connectable sterile connectors.

In addition, the aeration system may comprise a condenser 22. The condenser 22 may be located on the gas exit line and configured to reduce the loss of water by evaporation, as shown in FIGS. 4 and 6. These condensers may, in one embodiment, be fitted to the top of the bioprocess container. In one embodiment, the gas outlets and the condenser may be fitted into a holder at the upper portion of the shell, preferably at the cover. The holder may be adjustable to different angles from vertical to horizontal. The holder may also include at least one, such as at least two automatic pinch valves coupled to the controller such that the gas outlet may be switched automatically to a backup gas outlet if the internal bioprocess container pressure is too high. In one embodiment, the gas outlet filters and the condenser may be fitted onto the top of the bioprocess container using reusable connections. In one embodiment, the condenser unit may be replaceable and/or interchangeable.

In one embodiment, the aeration control system can be further configured to maintain a smooth $CO_2$ flow proportional to the cell culture demand and/or to prevent spiking or pulsed $CO_2$ flows. Accordingly, in one embodiment, the aeration control system may be configured to monitor dissolved $CO_2$ levels in the SUB environment, and/or to control an independent sparge rate, an independent acid addition pump, and/or a setting of a minimum output of $CO_2$ flow to the sparge. In one embodiment, dissolved $CO_2$ levels may be monitored via a $pCO_2$ sensor.

In one embodiment, the aeration system may comprise at least one dissolved oxygen tension (DOT) sensors. These sensors, in one embodiment, may be electrochemical sensors. In one embodiment, the controller may be configured to provide 2 types of DOT control: a capped air method and a gas mix method. In general, the capped air method provides a user-definable continuous flow of nitrogen introduced through a single mass flow controller (MFC). The DOT control can be achieved by increasing air flow-rate via a mass flow controller to match oxygen demand from cells, with the ability to start oxygen supply (via a mass flow controller) when the air flow rate reaches a user defined limit. Under these circumstances the air can be capped at a fixed flow-rate and oxygen added (under PID control) to supplement the demand. When the oxygen is no longer required, control will return to air flow. In the gas mix method, DOT and pH are controlled by a full 3+1 gas mix system. DOT is controlled by varying the mix of air/nitrogen and oxygen at a pre-determined, user selectable total gas flow rate. pH is controlled by the addition of $CO_2$ and alkali, without increasing the total gas flow rate.

Bioreactor Temperature Control

Referring to FIG. 6, in at least one embodiment, the single use bioreactor includes a temperature control system. The temperature control system may comprise a thermal jacket 280, a thermocirculator, and at least one temperature sensor 180. In one embodiment, the operation of the temperature control system is controlled by the controller. In some embodiments, the temperature sensor is in communication with the controller. In one embodiment, the thermal jacket and thermocirculator together heat and cool the cell culture within the bioprocess container so as to avoid the formation and/or perpetuation of hot and cold spots during single use bioreactor operation. The bioreactor jacket may partially or completely surround the shell and/or bioprocess container. In at least one embodiment, the thermal jacket at least partially, preferably fully, covers the lower portion of the bioreactor vessel above the probe shelving. In some embodiments, the thermal jacket may be in fluid communication with at least one of a heated or a chilled fluid. The bioreactor jacket may, in one embodiment, comprise a water jacket.

Exemplary embodiments of the bioreactor jacket 280 are shown in FIG. 6 and FIG. 10. As shown in FIG. 6 and FIG. 10, in some embodiments, the bioreactor jacket 280 covers the bottom half of the shell 110. The bioreactor jacket 280 may be configured such that at least one open space or hole is provided, such as for placement of a probe belt. As shown in FIG. 10, in one embodiment, the bioreactor jacket 280 may cover the bottom half of the shell that is above the probe belt(s) 290. This configuration may promote efficient heat transfer. The probe shelving 260 may be located on the bioreactor jacket 280.

In one embodiment, the at least one door 270 of the shell 110 may have a thermal jacket that may be separate from or connected to the thermal jacket of the bottom half of the shell. In a further embodiment, the top jacket may be connected to the bottom jacket via flexible tubing or the like in order to ensure that the at least one door can be opened.

In one embodiment, the temperature sensor senses the temperature of the cell culture medium during operation of the single use bioreactor. In embodiments wherein the temperature sensor is in communication with the controller, the controller may be configured to receive information from the temperature sensor and, based on that information, control the flow of a fluid into the bioreactor thermal jacket for increasing or decreasing the temperature of a culture media that is contained within the bioprocess container. As such, in some embodiments, the culture media is maintained within preset temperature limits.

The temperature sensor, in one embodiment, comprises a resistance temperature detector. In operation, in some embodiments, temperature set points can be provided as a temperature band such that temperature corrective action is taken when the measured temperature is outside the temperature band. In at least one embodiment, the temperature control system is configured to maintain temperature at +/−0.2° C. over a range of 10 to 40° C. In at least one embodiment, the temperature control system is configured to maintain temperature at +/−1.0° C. over the range of 5 to 20° C. In at least one embodiment, the temperature control system is configured such that temperature overshoot and undershoot does not exceed +0.8° C. for transitions between any set points in the range 10 to 40° C. In at least one embodiment, the temperature control system is configured to control temperature constantly at +/−0.1° C. during fermentation over a range of 10 to 40° C. In at least one embodiment, the temperature control system is configured such that the temperature control system is unable to heat above a certain temperature, such as 40° C., to avoid damage to any disposable component parts.

In one embodiment, the medium is brought to operating temperature by process control. In one embodiment, this is achieved by "gentle" heating or cooling of the jacket. For example, in one embodiment, very high or very low temperatures are avoided at the vessel wall. In at least one embodiment, the temperature control system is configured such that the thermal jacket warms 1000 L of cell culture medium from ambient to 34 to 40° C. in less than 6 hours. In at least one embodiment, the temperature control system is configured such that the thermal jacket chills 1000 L of cell culture medium from 34 to 40° C. to 10° C. in less than 6 hours. In one embodiment, the temperature control range during operation is 36 to 38° C. with an accuracy of ±0.2° C. at set point.

In one particular embodiment, the bioreactor jacket area may be specified with the following considerations in mind: (i) warming up of medium from 10° C. to 40° C.; (ii) all points within the bioreactor must reach ±0.2° C. of set point, typically e.g. 37° C., as measured by thermocouples, and (iii) chilling of medium from 40° C. to 10° C.

Probes 28/Probe Belt 290:

Referring to FIG. 7, in at least one embodiment, one or more of the various probes and/or sensors described herein are disposed in at least one probe belt 290 configured to position the various probes and/or sensors appropriately with respect to the bioprocess container. The at least one probe and at least one probe belt may be configured in any suitable location in or on the shell. For example, in one particular embodiment, the sample line is to be situated next to the pH probes to ensure close proximately when taking offline pH samples. In at least one embodiment, two or more probe belts are provided. Each probe belts may be capable of operationally housing at least one, such as at least two, such as at least three, such as at least four, such as at least five, such as at least six probes and/or sensors each. In one embodiment, the probe belts include two pH sensors and two DO sensors. In some embodiments, at least seven, such as at least eight, such as at least nine, such as at least ten additional probes may be accommodated. The probes may be opposite each other. In one particular embodiment, the probe shelving is configured to operationally support two probe belts, each capable of housing six probes opposite each other. In one embodiment, a probe belt, such as a probe belt containing spectroscopic probes, may be configured in order to protect the belt and/or the probes from light or other environmental conditions.

In one embodiment, the probes can rest on shelving. Referring to FIG. 10, in at least one embodiment, the lower portion of the shell 110 and/or the bioreactor jacket 280 includes probe shelving 260 configured to operationally support at least one probe belt 290 having various probes thereon. The shelving may be permanently or removably fixed to the bioreactor shell. The shelving may be oriented at a certain angle, such as greater than 1°, such as greater than 5°, such as greater than 10°, such as greater than 15°, such as greater than 30°, such as greater than 45°, such as greater than 60° degrees, with respect to the shell. In one embodiment, the probe shelving is oriented at an acute angle with respect to the shell exterior surface. In one particular embodiment, the probe shelving is oriented at a 30° angle with respect to the shell exterior surface.

In one embodiment, the various probes are in wired and/or wireless communication with the controller and/or their respective systems, and are configured to transmit respective data thereto. In one non-limiting embodiment, spectroscopic probes are either the RAMAN or NIR type. In some embodiments, the spectroscopic probes can receive and monitor characteristics including but not-limited to viable cell concentration, culture viability, glucose concentration, amino acid concentrations, lactic acid concentration, and ammonium concentration. In some embodiments, further measurement and analysis using additional tools may be necessary for product characterization. In one embodiment, the controller is preferably configured to control the various system set points (e.g., pH, Temperature, DOT, agitation, nitrogen flow rate, air cap) and pump flow rates (all integral pumps and external pumps) based on the output of the spectroscopic probe.

Methods

In a preferred embodiment of the present disclosure, the method according to the disclosure takes place in at least one single-use bioreactor of the present disclosure. In one embodiment, the present disclosure includes a method for comparing the performance of a bioreactor vessel across scale and vessel size. In another embodiment, the present disclosure includes a method for validation bioprocess container performance beyond the intended operating ranges, such as for scaling up or down. In a further embodiment, the present disclosure includes a method for theoretically or experimentally determining the number and size of holes in at least one sparger during scaling of the bioprocess container.

The disclosure also includes a method for cultivating and propagating cells and/or cell products, wherein at least one cell is cultivated under suitable conditions and in a suitable culture medium in a first bioreactor with a first volume, the medium containing the cells obtained by propagation from the at least one mammalian cells is transferred into a second bioreactor having a second volume, wherein the second volume is greater than the first volume, the transferred cells are cultivated in the second bioreactor, the medium containing the cells from the second bioreactor is transferred into a third bioreactor having a third volume, wherein the third volume is greater than the second volume, and the transferred cells are cultivated in the third bioreactor.

In one particular embodiment, the disclosure also includes a method for cultivating and propagating cells and/or cell products, characterized in that a) at least one mammalian cell is cultivated under suitable conditions and in a suitable culture medium in a first single use bioreactor with a volume of at least 10 L, such as at least 500 L, such as at least 1000 L, b) the medium containing the cells obtained by propagation from the at least one mammalian cell is transferred into a second single use bioreactor with a volume of at least 1000 L, such as at least 2000 L, such as at least 4000 L, c) the transferred cells are cultivated in the second single use bioreactor, d) the medium containing the cells obtained in step c) is transferred into a third single use bioreactor with a volume of at least 10,000 L, such as at least 20,000 L, and e) the transferred cells are cultivated in the third single use bioreactor. In one embodiment, the system may include a plurality of single use bioreactors in fluid communication with each other. The bioreactors can be controlled by a single controller or by multiple controllers. Each single use bioreactor in the system can, in one embodiment, have the same size. The volume of each single use bioreactor, for instance, can be e.g. 1000 L, 2000 L, 4000 L, 10,000 L, 20,000 L, etc.

In one embodiment of the disclosure, the method is characterized in that at least one of the bioreactors used is a bioreactor according to the disclosure. In a further embodiment, all bioreactors used are bioreactors according to the disclosure.

Bioreactors according to the disclosure are in this context all bioreactors described in this description, in the examples and in the claims.

In one embodiment, the bioreactor of step e) is operated in batch or fed batch mode. In one embodiment, the cells are cultivated in step e) preferably for 6 to 20 days.

Step a) is also called stage N-3 and/or N-2. Step c) is also called stage N-1. Step e) is also called stage N.

In one embodiment, the cultivation conditions in the bioreactors of steps a), c) and e) are the same. In one embodiment, the cultivation conditions in the bioreactors of steps a), c) and e) have a homogenous environment with respect to process parameters such as pH, dissolved oxygen tension and temperature. In one embodiment, pH, dissolved oxygen tension, and temperature in the bioreactors of steps a), c) and e) are the same.

In one embodiment of the disclosure, the seeding ratio after the transfer steps b) and/or d) is at least 10% v/v, such as at least 11% v/v (1 in 9 dilution) and at most 30% v/v, such as at most 20% v/v (1 in 5 dilution).

Train

The single-use bioreactor system according to the disclosure can also be used in a bioreactor train or device.

The bioreactor train, in one embodiment, can comprise different bioreactors, which are also called stages. For example, a bioreactor with a volume of at least 500 L, such as at least 1000 L may correspond to stage N-3 and/or N-2. The bioreactor with a volume of at least 2000 L, such as at least 4000 L may correspond to stage N-1. The bioreactor with a volume of at least 10,000 L, such as at least 20,000 L may correspond to stage N. In one embodiment of the disclosure there is a further bioreactor, such as a 50 L bioreactor, corresponding to stage N-4. In one embodiment of the disclosure, the N-4 bioreactor is a S-200 seed rocking bioreactor or a 100 L stirred tank reactor. In a one embodiment of the disclosure, the aspect ratio HL/T is at least 0.17 and at most 1.96.

In one embodiment, the bioreactor train may include a plurality of single use bioreactors in fluid communication with each other. The plurality of single use bioreactors can be controlled by a single controller or by multiple controllers. In one particular embodiment, the single use bioreactors can have the same volume, such as any of the volumes described above.

In one embodiment, the design of the bioreactor train is based on the need to ensure a homogenous environment with respect to process parameters such as pH, dissolved oxygen tension (DOT) and temperature, maintaining a well-mixed cell suspension and blending nutrient feeds within the bioreactor. In some embodiments, the bioreactors of the bioreactor train show geometric similarity. This can allow a scale-down model to develop, for example at 5 L laboratory scales or 500 l pilot scales. In some embodiments, the bioreactors of the stages N-3, N-2 and N-1 are used as seed-bioreactors, while the bioreactor of stage N is used as a production-bioreactor. The design of the seed- and production-bioreactors can be based on the same principles. However, in certain embodiments, some departures can be required to allow for flexibility in processing.

In another embodiment, the single-use bioreactors of the present disclosure can be used in series for fed batch or perfusion with a single controller, as described below. In one embodiment, a single controller as described below could control perfusion in series as much as fed batch in series. Yet another aspect of the present disclosure allows inoculation perfusion to be automated once the cells entered an inoculum/production vessel. In certain embodiments, this would enable support of development scales as well as smaller scale facility to increase output of production.

Figure 38:
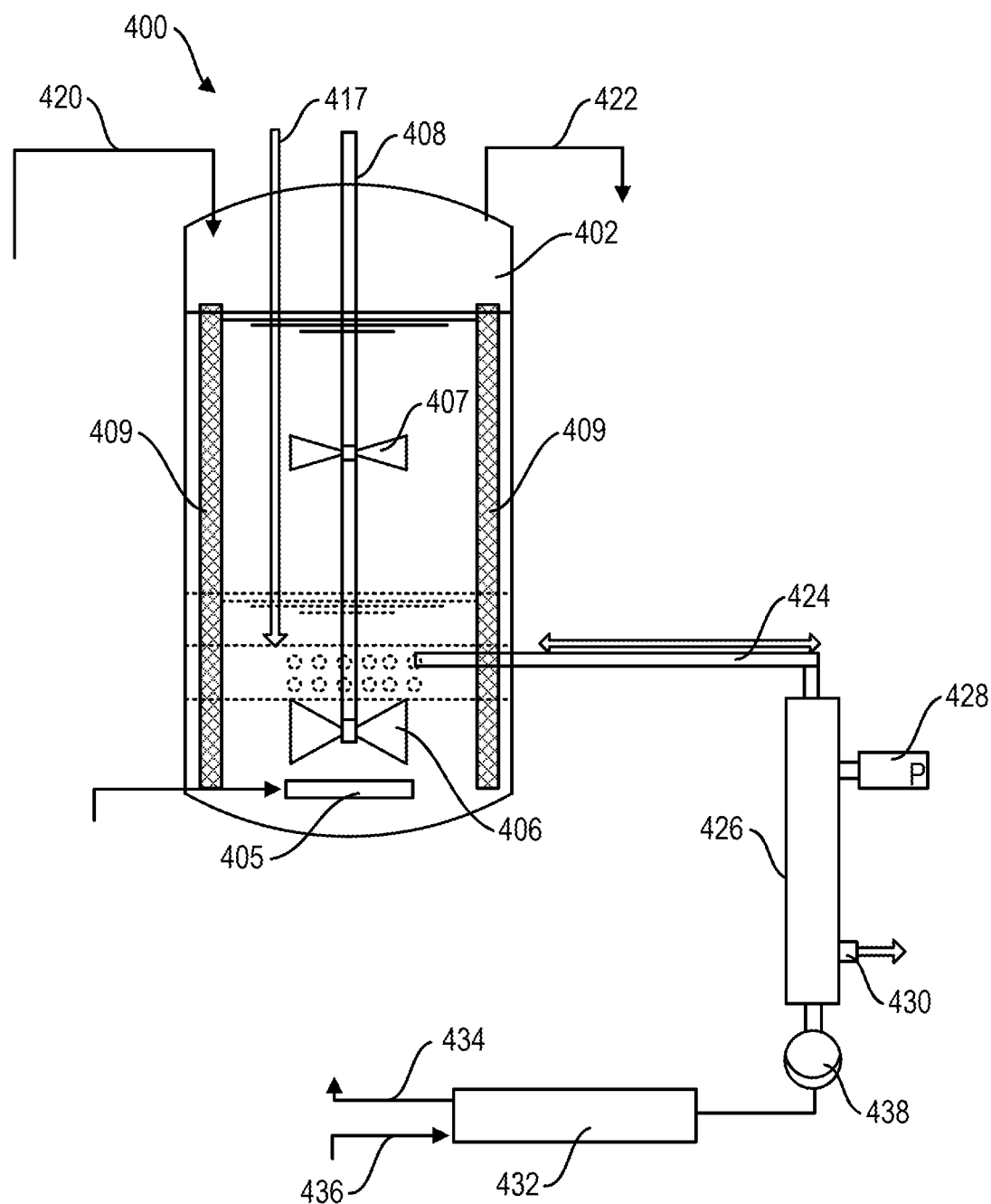
FIG. 38 illustrates one embodiment of a bioreactor system in accordance with the present disclosure that includes an external cell retention device for continuous perfusion of a cell culture.

In one embodiment, the single-use bioreactor of the present disclosure may be used in perfusion applications. For instance, referring to FIG. 38, one embodiment of a bioreactor system 400 for carrying out a perfusion process is shown. The bioreactor system 400 includes a bioprocess container 402 made in accordance with the present disclosure. The bioprocess container 402, for instance, can be made from a flexible film and can be inserted into a rigid metallic shell. The bioprocess system 400 can include a mixing device which includes a rotatable shaft 408 coupled to a first impeller 407 and a second impeller 406. As shown, the first impeller 407 is spaced from the second impeller 406. The first impeller 407 is located in a middle section of the bioprocess container 402, while the second impeller 406 is located in a bottom section of the bioprocess container 402.

A feed tube 417 is included for feeding fresh feed medium applied at a desired flow rate. The feed tube 417 can terminate with a one-way valve to prevent fluids from flowing into the feed tube 417.

The bioreactor system 400 can also include at least one sparger. For instance, in the embodiment illustrated in FIG. 38, the bioreactor system includes a first sparger 405. The first sparger 405 is a subsurface sparger located below the impeller 406. The sparger 405 can be used to feed air, oxygen, nitrogen, carbon dioxide and other gases into a culture media contained within the bioprocess container 402.

The bioreactor system 400 includes a second sparger 420. The second sparger 420 can be a supersurface sparger that feeds gases into the head space of the bioreactor container 402. The sparger 420, for instance, can feed overlay gases such as air, oxygen, nitrogen and carbon dioxide into the bioprocess container.

The bioreactor system 400 can further include a vent 422 in order to release gases from the system.

As shown, the bioprocess container 402 is in fluid communication with a recirculation line 424. The recirculation line 424 is in fluid communication with a cell retention chamber 426. A pressure gauge 428 can be used to monitor the pressure within the cell retention chamber 426.

The cell retention chamber 426 can be in fluid communication with a filtrate outlet 430. The filtrate outlet 430 is placed in association with a biofilter. The filtrate outlet 430 is configured to remove liquids from the cell retention chamber 426, such as spent liquids. The biofilter, however, is permeable to liquids but impermeable to biological materials, such as cells. Thus, filtrate can be removed from the cell retention chamber 426 without loss of biomaterial. The position of the recirculation line 424 can vary. The recirculation line 424 can be positioned at the top section, at the middle section or at the bottom section of the bioprocess container 402.

The bioreactor system 400 can further include a flow regulator 432. The flow regulator 432, for instance, may comprise an alternating tangential flow regulator. In the embodiment illustrated, the flow regulator 432 is in communication with a vacuum source 434 and a pressurized gas source 436 which may be an air pressure source. Upstream from the vacuum source and the gas pressure source, the flow regulator 432 is in fluid communication with a reciprocating diaphragm 438. The flow regulator 432 is configured to alternatively apply a vacuum or a gas pressure to a fluid contained in the cell retention chamber 426 by using, for instance, the reciprocating diaphragm 438. The reciprocating diaphragm 438, for instance, can alternate between applying pressure and applying a suction force to fluid contained in the cell retention chamber 426. In this manner, fluids such as a culture media can be recycled back and forth between the bioprocess container and the cell retention chamber for carrying out a perfusion process.

System

The present disclosure also relates to the use of single-use bioreactors in systems. The required system settings are covered in the single-use bioreactor control system described herein.

Forming single-use bioreactors of the present disclosure can, in one embodiment, be accomplished by fitting and/or inflation of a single use product contact bioprocess container to be inserted into a stainless steel shell and inflated. In another aspect of the present disclosure, filters may be fitted to the shell after inflation. In yet another aspect of the present disclosure, probes and sampling system may be fitted to the SUB after inflation.

In one embodiment, production may be commenced when the growth medium is filtered into the single-use bioreactor via gamma-irradiated sterilizing grade filters. In some embodiments, these filters can be welded onto the additional lines prior to or after gamma irradiation, but do not need to be. In some embodiments, the culture medium and gas inlet filters may be provided in the bioprocess container prior to gamma irradiation. Next, in some embodiments, the medium would be allowed to equilibrate in the single-use bioreactor (temperature, pH and dissolved oxygen) under agitation prior to inoculation. During the production process additional substrates, pH controlling solutions and antifoam may be added. The single-use bioreactor can be continuously monitored throughout this process.

In one embodiment, the cell culture can be harvested via disposable depth filter system to remove the cells and cell debris, prior to filtration and subsequent purification.

SUB Control System

In accordance with one or more aspects of the disclosure, a control system for controlling the single use bioreactor and its functionalities are provided and will now be described below. By way of example, the control system may include one or more controllers, one or more thermocirculators, one or more scales (e.g., industrial scale), one or more control pumps (e.g., automatic control peristaltic pump), and other suitable types of system components that may be controlled by the controller(s).

In one embodiment, the controller may control and/or monitor, such as via a sensor, at least the following parameters of the SUB: (1) pH, (2) dissolved oxygen tension (DOT), (3) dissolved $CO_2$ ($pCO_2$), (4) air, $O_2$, $CO_2$, $N_2$, (5) temperature, (6) agitation, (7) alkali, (8) nutrient continuous feed, (9) nutrient shot feed, (10) pressure, (11) foam, (12) level and other suitable types of parameters, all of which will be further described in detail below. The controller may be in communication with at least one sensor, and, based on the information provided by the sensor, may be able to control a material or fluid supply, such as by varying a flow rate of a fluid from the fluid supply into the hollow enclosure of the bioprocess container. As such, in some embodiments, the controller may assist in maintaining within present limits at least one parameter of a culture media contained within the hollow enclosure of the bioprocess container. In another embodiment, the thermocirculator may enable temperature control for fermentation heating (e.g., bioreactor set point of from 34° C. to 40° C.) and for cooling (e.g., bioreactor set point of 10° C.). In yet another embodiment, the scales may be required (per bioreactor unit) for feed addition control and monitoring; for instance, one scale may be dedicated to alkali addition linked to pH control or to process shot feed additions. In a further embodiment, the automatic control pumps may be required (per bioreactor unit) for further feed additional control and monitoring.

In one embodiment, the controllers provide increased flexibility, reliability and ease of use in their operation for both research and custom process manufacturing and development projects. Therefore, in some embodiments, the system must be able to be operated in a GMP environment as well as in a development laboratory. In certain embodiments, the SUB system can be operated as either inoculum reactor or as a production unit. As such, some of the control functions, for example DO control, required may be different from the ones described in paragraph above. In one embodiment, when operating in inoculum mode, pH or DO will not be controlled. In one embodiment, the control system should be flexible to accommodate either mode of operation. In some embodiments, it is likely that more than one disposable bioreactor unit will be operating in manufacturing, with either different or same volumes. All vessels may require the same control functions and each unit may require its own control system. Moreover, in some embodiments, the control package shall comply with current standards for equipment in accordance with cGMP practices, together with European and American regulatory requirements for pharmaceutical industries.

In embodiments with more than one controller, the controllers can be components of a smart communication system, wherein the controllers may communicate with each other and with a central control system during the culturing process or portions thereof to enable process integration. In various embodiments, the smart communication system may utilize central decision making with a central controller or distributed decision making between unit operators in continuous integrated processes.

Controller

The controller may be any type of processing hardware, such as a processor or a computing device, configured to control and execute various instructions for one or more components and/or related equipment associated with the single-use bioreactor described herein. In one embodiment, the controller may comprise one or more microprocessors. It may be understood that more than one controller may be used to perform control and the various components of the control system may be connected via a system network.

Figure 36:
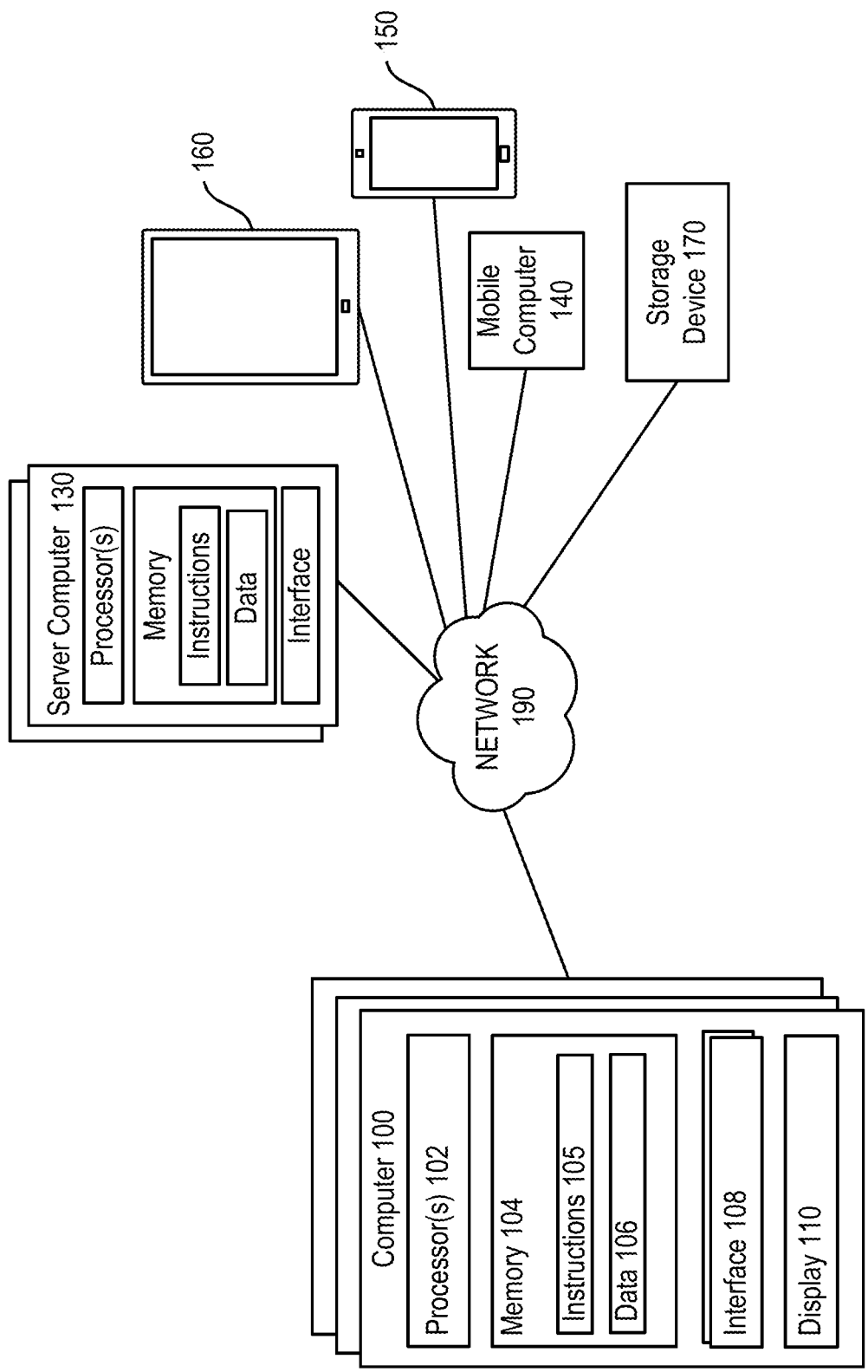
FIG. 36 is an example SUB control system.

FIG. 36 illustrates an example system in accordance with one or more aspects of the disclosure. The system may include one or more computing devices, e.g., computer 100, server computer 130, mobile computer 140, smartphone device 150, tablet computer 160, and storage device 170 connected to a network 190. For example, the computer 100 may be a desktop computer, which is intended for use by one or more users. The computer 100 includes various components associated with a desktop computer, such as one or more processors 102, memory 104, e.g., permanent or flash memory (which includes instructions 105 and data 106), one or more interfaces 108, and a display 110. In a further example, similar to the computer 100, the server computer 130 may include at least one processor, memory which also includes instructions and data, one or more interfaces, and/or a display (not shown). Moreover, the mobile computing device 140 may be a laptop (or any type of computer that is portable or mobile, such as an Ultrabook) and also include components similar to the computer 100 and/or server computer 130. The computer 100 may be configured to communicate with the server computer 130, the mobile computer 140, the smartphone device 150, the tablet computer 160 and/or the storage device 170 via the network 190.

The computer 100 can include a processor 102 (e.g., the controller), which instructs the various components of computer 100 to perform tasks based on the processing of certain information, such as instructions 105 and/or data 106 stored in the memory 104. For example, the processor 102 may be hardware that can be configured to perform one or more operations, e.g., adding, subtracting, multiplying, comparing, jumping from one program to another program, operating input and output, etc., and may be any standard processor, such as a central processing unit (CPU), or may be a dedicated processor, such as an application-specific integrated circuit (ASIC) or a field programmable gate array (FPGA) or an industrial process controller.

Memory 104, whether permanent or flash, may be any type of hardware configured to store information accessible by the processor 102, such as instructions 105 and data 106, which can be executed, retrieved, manipulated, and/or stored by the processor 102. It may be physically contained in the computer 100 or coupled to the computer 100. For example, memory 104 may be ROM, RAM, CD-ROM, hard drive, write-capable, read-only, etc. Moreover, the instructions 105 stored in memory 104 may include any set of instructions that can be executed directly or indirectly by the processor 102. For example, the instructions 105 may be one or more "steps" associated with software that can be executed by the processor 102 to control various aspects of the SUB control system. According to one aspect of the disclosure, the instructions 105 may include at least a set of executable instructions to read various values and/or parameters associated with the SUB. According to another aspect of the disclosure, the data 106 may include data that may be used by the control module, such as sensor readings, data collected by sensors, predetermined parameters, readings associated with valves, pumps, agitators, scales, switches, temperature measurements, pressure measurements, level measurements, dissolved oxygen measurements, etc.

Interface 108 may be a particular device (such as a field-mounted instrument, processor-to-processor communication, keyboard, mouse, touch sensitive screen, camera, microphone, etc.), a connection or port that allows the reception of information and data, such as interactions from a user or information/data from various components via network 190. Alternatively, the interface 108 may be a graphical user interface (GUI) that is displayed to the user/operator on the display 110. By way of example only, the GUI may be an operator interface (OI) that displays processing units and data to a user or operator. Moreover, the display 110 may be any suitable type of device capable of communicating data to a user. For example, the display 110 may be a liquid-crystal display (LCD) screen, a light emitting diode (LED) screen, a plasma screen, etc.

The network 190 may be any suitable type of network, wired or wireless, configured to facilitate the transmission of data, instructions, etc. between one or more components of the network. For example, the network 190 may be a local area network (LAN) (e.g., Ethernet or other IEEE 802.03 LAN technologies), Wi-Fi (e.g., IEEE 802.11 standards), wide area network (WAN), virtual private network (VPN), global area network (GAN), or any combinations thereof. In this regard, the computer 100, server computer 130, mobile computer 140, smartphone device 150, and/or tablet computer 160 may connect to and communicate with one another via the network 190.

While the computer 100 may be a desktop computer in the above-described examples, computer 100 is not limited to just desktop computers, and any of the computers illustrated in FIG. 36 may be any device capable of processing data and/or instructions and transmitting and/or receiving data. Moreover, it should be understood that those components may actually include multiple processors, memories, instructions, data or displays that may or may not be stored within the same physical housing.

pH Control

In accordance with one embodiment of the disclosure, one or more controllers of the SUB control system, such as the one or more processors of computer 100 in FIG. 36, may be used to measure and receive pH values of the biomaterial in the bioprocess container via at least one sensor, and in some embodiments at least two sensors, such as electrochemical sensors. During control procedures, for example, only one pH sensor may be used or two or more pH sensors may be used. Each pH sensor used may be in communication with the controller. When two sensors are used, the controller may select between the two sensors, either manually or automatically, depending on whether there are detected errors in the measured pH values. Based on the pH readings, the controller may regulate pH levels by adding requisite amounts of acid or alkali.

In another example, the controller may use a $CO_2$ gas supply to decrease pH and a pumped liquid alkali to increase pH in order to control to a set point. The $CO_2$ gas supply and/or the liquid alkali supply may be in fluid communication with the bioprocess container. In one embodiment, the ability to operate a "dual" pH set point may be implemented. For instance, a high and low pH set point can be user configurable. Between the high and low set points, no control action ($CO_2$ or alkali) may be required and pH may drift within this band. When pH is less than the low pH set point, alkali may be required, and when the pH is above the high set point, $CO_2$ may be required. In certain embodiments, the controller should not have to "fight" between the addition of $CO_2$ and alkali such that they counteract each other resulting in overdoses of each.

As such, for example, the controller may set and control pH set points between two different and/or opposing outputs, the first of which may be the $CO_2$ mass flow controlled gas addition and the second of which may be proportional control pumped addition of an alkali solution. Moreover, the controller may be configured to perform temperature compensation based on measure pH values, where temperature values may be selected from the one or more pH sensors.

In yet another embodiment, the controller may allow a user or operator to enter a separate value and define an upper and lower zone between which there may be no particular control or control action, e.g., no $CO_2$ addition or alkali additions based on the pH measurements and subsequent control. This may be referred to as "deadband" functionality. When using the deadband function, which may be between +/−0.01 to +/−0.30 pH units relative to the process setpoint, the process control of pH and the corresponding $CO_2$ additions, if/when applicable, may have minimal oscillation. In other examples, the controller may be configured to receive two pH set points (e.g., one at either end of the deadband). It may be understood that when operating with a pH deadband (for example, +/−0.01 pH relative to the minimum set point), there must be no control discrepancies and/or inconsistencies between $CO_2$ and alkali additions In at least that regard, one of the numerous advantages of the controller controlling pH is that the system can exhibit responsiveness and adherence to the set point(s) with stable additions of $CO_2$ and/or alkali (e.g., minimal oscillations).

In a further example, the controller may alert the user or operator by way of an alarm system any deviations, such as a drift between controlling and any non-controlling pH sensors. The range of deviation may be configured by the user/operator using an interface, such as interface 108 of computer 100 in FIG. 1. In yet further aspects of the disclosure, single-point calibration may be used to adjust to an off-line pH measured value.

DOT Control

In accordance with another embodiment of the disclosure, the one or more controllers of the SUB control system, for example the processor(s) of the computer 100, may be used to measure and control dissolved oxygen levels, such as DOT, using at least one sensor, and in some instances at least two sensors, such as electrochemical sensors. Similar to pH control as described herein, during DOT control procedures, only one sensor may be used or two or more sensors may be used. If two sensors are used, the controller may select between the two sensors (manually or automatically) depending on whether there may be detected errors in the DOT measurements.

In one embodiment, a DOT set point may be controlled based on respective output(s) corresponding to additions of compressed air and compressed oxygen mass flow controlled gas, which may be operated in a cascaded format. Thus, in one embodiment, when using air and oxygen control, DOT levels can be maintained with only air until a configurable airflow point is reached. Moreover, oxygen may meet DOT demand while also maintaining a constant air flow. But, for instance, when there is insufficient demand for oxygen (e.g., at a configurable setpoint), control via the controller may be returned to air in an automatic manner.

In another example, similar to the pH sensors described herein, the controller may be configured to perform automatic temperature compensation based on measured DOT value and the temperature value may be selected from the one or more DOT sensors.

As such, an advantage of the controller performing control of the DOT is that the system will exhibit responsiveness and adherence to the set point(s) with stable additions of air and/or $O_2$ (e.g., minimal oscillation). The controller, in examples, may alert the operator via an alarm system when the controller detects a deviation or drift between controlling and any non-controlling DOT and/or pH sensor. In some embodiments, the range of the deviation is configurable by the user. In a further aspect, single-point calibration may be used to adjust to an off-line DOT measured value.

In a further example, there may be at least two types of DOT control that may be supplied: the capped air method and the gas mixed method. In the capped air method, a user-definable continuous flow of nitrogen introduced through a single mass flow controller (MFC) may be implemented. The DOT control is achieved by increasing air flow-rate via a mass flow controller to match oxygen demand from cells, with the ability to start oxygen supply (via a mass flow controller) when the air flow rate reaches a user defined limit. Under these circumstances the air will be capped at a fixed flow-rate and oxygen added (under PID control) to supplement the demand. When the oxygen is no longer required, control will return to air flow. In the gas mix method, for instance, DOT and pH can be controlled by full 3 plus 1 gas mix system. DOT may be controlled by varying the mix of air/nitrogen and oxygen at a pre-determined, user selectable total gas flow rate. pH control can be performed by the addition of $CO_2$, without increasing the total gas flow rate.

$pCO_2$ Control

In accordance with yet another embodiment of the disclosure, the one or more controllers of the SUB control system may monitor and control dissolved $CO_2$ ($pCO_2$). For example, $pCO_2$ may be measured using a sensor and the measurement transmitted by a transmitter. The transmitter, in some examples, may physically be mounted within the housing of the controller, but control may be performed externally, e.g., on an interface of the controller, for the user to execute single point and/or two-point calibration via the interface. In further examples, the $pCO_2$ may be linked to an independent air flow via, for example, mass flow control (MFC) to a sparge and also set a minimum $CO_2$ flow output via MFC.

In one embodiment, the $pCO_2$ measurement values enable control on the airflow to a sparger (which, in some examples, may join with another sparge prior to bioreactor entry and/or sterile filtration) and also the $CO_2$ MFC valve. By way of example, control may be performed to prevent conditions of excessively high or low $pCO_2$ while maintaining suitable set point control of pH and DOT values. The control process for doing so may include the steps of automatically adding a fixed rate of airflow to one sparge, which may be triggered by activation of a first $pCO_2$ alarm value (e.g., "hihi" value). In some instances, the airflow via an open pipe may act to strip out $CO_2$ and thus reduce $pCO_2$. Thereafter, a fixed rate of $CO_2$ to another sparge may automatically be added and the fixed rate of $CO_2$ may be triggered by activation of a second $pCO_2$ alarm value (e.g., "lolo" value). For example, the lolo alarm may trigger the $CO_2$ mass flow control valve to remain open at, for instance, 2 percent of full span (which may be a value set by the operator), regardless of its current state for active pH control.

Redox

In accordance with a further embodiment of the disclosure, the one or more controllers of the SUB control system may monitor reduction-oxidation (redox) measurements, which may be taken using one or more sensors. In examples, a transmitter for transmitting the redox measurements may be implemented.

Gases

In accordance with another embodiment of the disclosure, the one or more controllers may be used to control the flow of gas, such as air, oxygen, $CO_2$, $N_2$, which may be related to the control of pH and DOT described herein. Gasses may be introduced into the bioreactor using a single sparger, e.g., located at the base of the bioreactor. Alternatively, two sparger outlets and one outlet to headspace may also be used. In examples, gasses may be introduced to the bioreactor at the same time via the spargers and headspace under maximum level operating conditions in the following full span bioreactor ranges.

By way of example, the controller may be configured to activate the flow control of gasses via manual activation (e.g., performed by operator) and/or automatic activation (e.g., linked to an in-line $pCO_2$ measurement).

In another example, the gas overlay (e.g., air) may be controlled through a mass flow control valve. The controller may allow for manual variable set point change during cell culture run. The ranges required are as follows: SUB 50 L: 0 to 0.5 L; SUB 250 L: 0 to 1 L; SUB 1000 L: 0-2 L. It may be understood that these values may be refined as further operational data is obtained.

Moreover, the gas overlay flow value may be displayed on an interface, such as a touch screen (or other human machine interface (HMI)). Display screen can show actual value and set point. An alarm may sound if gas overlay set point value falls outside the alarm limits. A message may appear on the alarm screen and be electronically logged. And the ability to switch off gas overlay automatically may be required if it reaches hihi alarm. This is to avoid any pressure build up inside the bioprocess container, as it is not rated as a pressure vessel. A message should appear on the screen flashing to warn that gas overlay has been switched off. This message may also be logged. The restart of the gas flow overlay may then be done manually on the touch screen once operator has acknowledged the alarm and checked that system can cope with the gas flow.

Temperature Control

In accordance with an embodiment of the disclosure, the one or more controllers may control the temperature of the SUB using a thermal jacket system that is preferably a water jacketed system, as described herein. Moreover, at least one thermocirculator, and in some examples at least two, are used for heating and chilling.

According to an example, the temperature of the SUB may be controlled based on temperature measurement(s) of the bioreactor vessel contents using a temperature sensor. For instance, an in-line bioreactor temperature sensor may be used for each bioreactor. Alternatively and/or in addition, a depth sensor may be used.

According to another example, the controller(s) may also be configured to alert the user of any type of deviation via an alarm system, which is capable of detecting a drift between controlling and any non-controlling temperature sensor. The range of this deviation may be configurable by the user via an interface of the controller, e.g., interface 108 of computer 100.

As discussed above, circulation and temperature control of vessel contents can be designed to avoid hot and cold spots during bioreactor operation. In one aspect, temperature control can be maintained at ±0.2 degrees Celsius over the range of 10 to 40 degrees Celsius. In another aspect, temperature control can be maintained at ±1.0 degrees Celsius over the range of 10.0 to 20 degrees Celsius and 36 to 40 degrees Celsius. In yet another aspect, the overshooting and under-shooting of the temperature should not exceed +0.8 degrees Celsius for transitions between any set points in the range 10 to 40 degrees Celsius. In other embodiments, temperature may be controlled constantly at +/−0.1 degrees Celsius during fermentation over a range of 10 to 40 degrees Celsius. In certain embodiments, heaters are not to be used above 40 degrees Celsius to avoid damage to any of the disposable component parts.

Moreover, signals can be provided for temperature measurement and control, data logging and alarms, and temperature compensation for the pH sensor unit. A continuous digital display of the temperature value to one decimal place may be provided. Display of the temperature reading must be on the mimic touch screen (or other HMI) should be for both actual reading and desired set point.

For the heating mechanism, for example, the controller may supply an output for an electrical jacket attached to the SUB reactor. Plugs and sockets may have a positive lock to prevent accidental removal of lead.

Algorithms may be used for temperature control to the heater actuators. The temperature values used by the controller must be available for logging. There may be user definable set-points with "high high, high" and "low low low" alarm limits. There must be the ability to auto-tune various terms.

Agitation

In accordance with another embodiment of the disclosure, the one or more controllers may control the mechanical circulation of the liquids in the bioreactor vessel (e.g. 400 L vessel) via an impeller, e.g., a dual impeller system.

For example, the controller may measure and control the agitation speed based at least in part on inputs from a calibrated tachometer that may be mounted next to the top of the motor.

Feeds Addition During Fermentation

In accordance with yet another embodiment of the disclosure, the one or more controllers of the SUB control system may allow peristaltic addition pumps to be run in automatic or manual modes. For example, the addition pumps may be used for alkali addition, which may be monitored via a dedicated scale and/or a dedicated pump totalizer. Moreover, there may be multiple continuous feed additions at variable rates as well as multiple shot feed additions (which may be monitored via a dedicated scale and/or a dedicated pump totalizer). As will be further described below, automation software may be executed by the controller for running, for instance, shot addition sequence.

Additions feeds can be operated via the control system and can allow for gradual feed addition or single shot based on quantity over a period of time.

In one example, three industrial scales per bioreactor unit may be used for feed addition control and monitoring. Each of the industrial scales may be dedicated as follows: a first scale ("scale one") to either Alkali addition linked to pH control or to process shot feed additions, a second scale ("scale two") to "Continuous Feed 1," and a third scale ("scale three") to "Continuous Feed 2."

In another example, seven automatic control peristaltic pumps per bioreactor may be used (e.g., two independent pump rack sets of seven and/or split as required per system) for further feed addition control and monitoring. The pumps may be dedicated to Alkali addition for pH, Continuous Feed 1, Continuous Feed 2, "Shot Feed 1," "Shot Feed 2," "Shot Feed 3," and "Shot antifoam" addition. The peristaltic pumps, for instance, may be configured for variable speed. The pump speed may be determined automatically by the control system to achieve a required addition feed rate entered by the operator. In manual mode, the pump speeds may be determined and set by the operator.

Moreover, in one embodiment, delivery rates may include configurable alarm limits to delimit the maximum and minimum delivery rate around the configured setpoint(s). Additionally, feed rates may be automatically confirmed based on loss-in-weight measurements or via calibrated flow controllers.

By way of example, the antifoam addition, and Shot Feeds 1, 2 and 3 may be controlled by the controller as follows. An operator may turn on the pump at a variable speed selected by the operator. After priming the line to the point of entry to the bioreactor, the actual addition will be quantified by the pump totalizer. An external scale, for instance, may be used for the pump calibration. Once primed, the controller facility for dosing a single addition (repeated on multiple days during the fermentation) may be performed. Subsequently, the user inputs the quantity to dose.

As described herein, the SUBs may already have suitable ports to connect the following: medium fill and inoculation;

alkali for pH control; variable rate Continuous Feed 1 (e.g., approximately 25% of batch volume); variable rate Continuous Feed 2 (e.g., approximately 13% of batch volume); shot 1 acidic (e.g., approximately 2% of batch volume); shot 2 alkali (e.g., approximately 1% of batch volume); shot 3 pH neutral (e.g., approximately 2% of batch volume); antifoam (e.g., approximately 0.1% of batch volume). A suitable dosing cart, scale, and/or pump tower unit may be used to enable the best use of floor space and also operator access to set up at start of batch.

In addition, medium and inoculation addition may be controlled manually by the operator, with use of the bioreactor load cells. Alkali (e.g., medium pillow bioprocess container in rigid tray) may be located on an existing shelf and monitored either using a scale or pump for monitoring and/or totalizing of additions.

Continuous Feed 1 (e.g., large upright bioprocess container in cylindrical rigid drum) may be located on a low level (or floor space) dedicated scale. For example, feedback process control to a feed rate set point may be implemented. The scale will be zeroed with an empty container. At a user settable lolo level alarm, an interlock to stop feedback control (e.g., will not attempt to add from an empty bioprocess container) may be used.

Continuous Feed 2 (e.g., medium pillow bioprocess container in rigid tray) may be located on a low level (or floor space) with dedicated scale. For instance, feedback process control to a feed rate set point may be implemented. Similar to the above, the scale may be zeroed with an empty container. At a user settable lolo level alarm, an interlock may stop feedback control (e.g., will not attempt to add from an empty bioprocess container).

Shots 1, 2 and 3 (e.g., medium pillow bioprocess container in rigid tray) may share a dedicated existing shelf and may be monitored either using a scale (if not used for alkali) or pump for monitoring and/or totalizing of additions. The antifoam (e.g., small bioprocess container or glass aspirator) may be located on an existing shelf and connected to a dedicated pump for monitoring and/or totalizing of additions. The seven peristaltic pumps may be fitted with tubing, such as, in one embodiment, 3.2×8.0 mm silicone tubing or ¼"×7/16" c-flex or 6 mm×12 mm silicone.

By way of example, a process may include the addition of three shots at defined quantities and times during a batch. The three shots are acid, alkali, and neutral and may be added in that sequence. The shot volume per addition may be relatively small (e.g. between 0.15 and 0.5% of target bioreactor starting volume). The same set of three shots are added on multiple days during a batch. When adding these shots, it may be necessary to first inhibit just the alkali output for pH control, which prevents alkali being added unnecessarily (and irreversibly) during the acid shot. This, however, may be counteracted by the alkali shot that may immediately follow.

Moreover, the $CO_2$ addition for pH can remain active throughout. To ensure the process is controlled within known boundaries, these shots may be added at a suitable rate so as not to breach the acceptable pH range, such as triggering the lolo and/or hihi alarms. Automation of the shot sequence may thus include: (1) user definable volume for each shot to be added, (2) inhibiting alkali addition for pH control immediately prior to first shot, (3) tubing prime step to ensure shot liquid position is at the point of entry to the bioreactor (e.g., stopped by operator based on visual check), (4) each shot being added in series ("option 1"); and all 3 shots being added simultaneously ("option 2"). If, during shot addition, the pH approaches the lolo or hihi alarm limits, then the addition sequence is paused to wait until pH lo or hi alarms are re-established. The controller may also re-activate alkali addition for pH control at completion of the shot sequence and when pH within lo and hi alarms.

In one aspect, use of a scale for shot addition monitoring may be used. Three shots, for instance, may be stored in one or more separate bioprocess containers, which may be able to be stacked in individual trays. This stack of trays may be placed on a single scale, in which case, shots being added in series (e.g., option 1) can be performed using the change in mass from the scale.

In another aspect, use of pump totalizers for shot addition monitoring may be implemented. The pumps may have dedicated tubing lines which can be calibrated for this tubing type. After priming and resetting the totalizer, the pumps may determine the correct quantities to add and may also data log this quantity. Either option 1 (added in series) or option 2 (added in parallel) is appropriate since each pump will be operating independently, as opposed to what would be done on a single scale. In at least that regard, with the option 2 approach, the low and high pH perturbation will be reduced and cancelled out by both the acidic and alkali shots entering the bioreactor together. The lolo and hihi pH monitoring sequence may still be required in this scenario, but rather than wait for pH to return within alarm range, response can be performed by stopping the acid shot (if pH approaching lolo alarm) or alkali shot (if pH approaching hihi alarm).

Bioreactor Pressure

In accordance with a further embodiment of the disclosure, the one or more controllers of the SUB control system may monitor and control the bioreactor pressure via a device mounted on the bioreactor headspace. At a user defined pressure alarm value, this will enable a control action to stop all gas additions as a safety interlock. Moreover, the controller may be configured so as to scale for negative and positive pressure.

In examples, for system consistency and improved pressure test capability, a digital display pressure sensor may be provided. Moreover, it is possible to add a bioreactor pressure control valve on a gas outlet, which will enable feedback pressure control of the bioreactor based on the digital display pressure sensor.

Since the SUB may not be a rated pressure vessel, custom designed SUB bioprocess containers can be installed with a disposable pressure transducer. In some embodiments, the pressure inside of the SUB bioprocess container should not exceed a certain pressure. Provision to alarm and data log the pressure may be required. The controller may be configured to shut gases off if a high pressure alarm sounds. In some embodiments, the controller may be configured to open a second gas outlet filter, such as by opening pinch valves, prior to shutting the gases off. A message should appear on the screen saying bioprocess container is over pressurized, which may be logged. To initiate gases again a second prompt (e.g., "are you sure?") may be displayed for safety reasons.

Antifoam

In yet another embodiment of the disclosure, the one or more controllers of the SUB control system may implement at least one foam sensor and transmitter, which may be directly integrated in the SUB and determine the amount of antifoam to be added in mass, which may also be displayed to an operator on an interface. For example, the level or measurement of foam in the SUB may be measured and transmitted to the controller for further processing in order to maintain requisite levels of antifoam. Moreover, these readings may be displayed on an interface for an operator. Provision may be made for the user to set the required flowrate if using manual control. If using the controller, then a timed on/off method may be used. In an example, the period of on and off may be definable by the operator via a touch screen.

Level

In an additional embodiment of the disclosure, the one or more controllers of the SUB control system may integrate a level sensor and transmitter for detecting level values. These values, like many other measured values described herein, may also be displayed for the operator.

Auxiliary Input and Control Loops

In accordance with an embodiment of the disclosure, at least two auxiliary inputs for signal generation may be needed for each controller used for controlling the SUB control system. A channel, for example, can be used for connection of a biomass sensor and transmitter output (e.g., Aber Instruments BM 200, redox sensors, etc.).

Additionally, for example, at least two auxiliary inputs for signal generation and feedback control may be implemented for each controller. A channel, here for example, could be used for connection of an optical DOT sensor (e.g., Mettler Toledo InPro6960i, etc.).

Software

In accordance with another embodiment of the disclosure, software and/or the set(s) of computer executable instructions for controlling the SUB control system can be provided. For example, the application code for the one or more control procedures described herein may be developed from an established library of "routines" or modules (e.g., for scaling, motor control, calculation blocks, etc.). The routines may be tested, documented, developed, and verified beforehand. Moreover, input signals associated with an unstable medium may include a damping facility, either in-circuit or applied as a software function, in order to eliminate, for instance, spurious operation (e.g., process variable (PV) filters). Further, all setpoints/operational parameters (e.g., alarm limits, alarm deadband parameters, etc.) may be accessible and adjustable via the control system, and software for allowing control and adjustment of those parameters may be implemented. In examples, the process setpoints/operational parameters may be entered into the control system in the engineering units to which they are defined and may be configurable during the batch production operation cycle.

In further examples, processing interlock capability for the system may be provided based on signal processing. Interlock may be provided between agitation and temperature control, temperature control and bioreactor level, bioreactor bioprocess container pressure and gas additions via mass flow control valves (MFCVs), feed addition balance and corresponding feed addition pump (e.g., low alarm for feed weight stopping pump), and shot feed addition pumps and pH lolo or hihi alarms.

Data and Alarms

Data, alarms, and/or various events may be captured on a network, such as network 190 of FIG. 1. In the event of a failure of the IT Network, the data can continue to be saved to the application station. Moreover, the operator interface system may provide read-only access to historical data stored on the drive or in the event of failure from the local drive and the reporting system may be able to detect altered and/or corrupted electronic records.

For example, an automatic, electronic audit trail may be implemented to capture all changed data, date and time and author of the change. The audit trail must not be editable and must be inextricably linked to the electronic records whose data has been changed. The audit trail can be classed as an electronic record and may be treated with the same level of security as the data.

Additionally, electronic records associated with this application may, with the appropriate security access, be capable of being copied without adversely impacting the record. Dynamic process data directly derived from the bioreactor batch may be made available to a specified location on the above-described network for offline analysis. The transferred data may be linked into discrete files (or alternative applications) created by the user and generated for each batch to view the in-line process control parameters.

In further examples, alarms may be captured and annunciated (e.g., audible and visual) locally or generally. For example, "Product Critical Alarms" can be identified at the impact assessment phase that indicates a possible impact on product quality, "Process Alarms," whose limits are defined "Alarm Limits," when detected can indicate a transgression from normal operating parameters but not impacting product quality. "System Alarm," when detected can indicate a failure of a plant item or control system component to operate to expectation. In one embodiment, only certain users may acknowledge alarms based on user security rights.

Alarms may be individually inhibited via the operator interface and such instances may be logged as events. The SUB control system may also maintain an alarm log, identifying each and every alarm event and their associated time and date. Each alarm may display a meaningful identification (e.g., tag and description).

One of the numerous advantages of the SUB control system is that the overall mechanism can be provided to so as to customize various processes that are not only run on each SUB unit but also other types of bioreactors. With respect to feeds, for example, another advantage is that there may be continuous feed set point control of flow rate, alarms and ability to automatically stop addition when the feed bioprocess container is empty and there may be the ability to dose multiple shots in series, or in parallel (simultaneously), designed to be added in way that hi/lo pH feeds have a net neutral effect on the cell culture. With respect to automation, for instance, another advantage is that there may be automation that enables 2-click operation of multiple shot feeds to be added in a controlled way that is able to prevent exceeding hi/lo pH conditions in the bioreactor and automation that enables manipulation of $pCO_2$ levels using in-line $pCO_2$ measurement linked to $CO_2$ gas flow and a $CO_2$ stripping gas (such as air or nitrogen flow). With respect to sensors, for example, a further advantage is that in-line redox measurements could be used to determine optimum cell culture conditions that minimize risk of antibody dis-association or damage (e.g., by better understanding or preventing highly reducing or oxidizing conditions during fermentation and harvest); in-line biomass (capacitance) has been used previously at pilot scale, which is a reading that could potentially be used to automatically start or adjust nutrient feed addition rates; and other in-line measurements of interest include glucose, lactate, glutamine, glutamate, ammonia and to perform in-line measurements of these, and other parameters.

The systems, devices, facilities, and/or methods described herein are suitable for use in and with culturing any desired cell line including prokaryotic and/or eukaryotic cell lines. Further, in embodiments, the systems, devices, facilities, and/or methods are suitable for culturing suspension cells or anchorage-dependent (adherent) cells and/or tissues and are suitable for production operations configured for production of pharmaceutical and biopharmaceutical products—such as polypeptide products, nucleic acid products (for example DNA or RNA), or cells and/or viruses such as those used in cellular and/or viral therapies.

In some embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the systems, devices, facilities, and/or methods can be used for producing biosimilars.

As mentioned, in embodiments, systems, devices, facilities, and/or methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the systems, devices, facilities, and/or methods can include any desired volume or production capacity including but not limited to bench-scale, pilot-scale, and full production scale capacities.

Moreover and unless stated otherwise herein, the systems, devices, facilities, and/or methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the systems, devices, facilities, and/or methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57BI/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica,* or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus Amphora, Bacillariophyceae, *Dunaliella, Chlorella, Chlamydomonas,* Cyanophyta (cyanobacteria), *Nannochloropsis, Spirulina,* or *Ochromonas*), or a plant cell (e.g., cells from monocotyledonous plants (e.g., maize, rice, wheat, or Setaria), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus*. *Bacillus* that can be used is, e.g. the *B. subtilis, B. amyloliquefaciens, B. licheniformis, B. natto,* or *B. megaterium*. In embodiments, the cell is *B. subtilis,* such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus Ohio 43210-1214.

In one embodiment, the prokaryotic cell is a Gram-negative cell, such as *Salmonella* spp. or *Escherichia coli,* such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant Cl esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AID-SVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH (1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH (7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-IS1, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™) bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE 1

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |

TABLE 1-continued

| Protein Product | Reference Listed Drug |
|---|---|
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molelcule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/ Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/ Growth factor | Type I alpha-interferon | Infergen |
| | Interferon-αn3 (IFNαn3) | Alferon N |
| | Interferon-β1a (rIFN- β) | Avonex, Rebif |
| | Interferon-β1b (rIFN- β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/ Protein vaccines/ Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tubingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

The enablements described in detail above are considered novel over the prior art of record and are considered critical to the operation of at least one aspect of the disclosure and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described herein, what is conceptually equivalent, what can be obviously substituted, and also what incorporates the essential ideas.

Furthermore, the functionalities described herein may be implemented via hardware, software, firmware or any combination thereof, unless expressly indicated otherwise. If implemented in software, the functionalities may be stored as one or more instructions on a computer readable medium, including any available media accessible by a computer that can be used to store desired program code in the form of instructions, data structures or the like. Thus, certain aspects may comprise a computer program product for performing the operations presented herein, such computer program product comprising a computer readable medium having instructions stored thereon, the instructions being executable by one or more processors to perform the operations described herein. It will be appreciated that software or instructions may also be transmitted over a transmission medium as is known in the art. Further, modules and/or other appropriate means for performing the operations described herein may be utilized in implementing the functionalities described herein.

The scope of this description is to be interpreted only in conjunction with the appended claims and it is made clear, here, that the named inventor believes that the claimed subject matter is what is intended to be patented.

Example 1

1,000 L Single-Use Bioreactor

In this example, a single-use bioreactor of 1,000 L according to the present disclosure is used. A SUB is gamma irradiated (i.e. supplied sterile and ready to use) and is placed into a shell (30). The shell (30) has a jacketed temperature control capable of heating and cooling the culture in combination with an appropriate controller system and thermo circulator. The SUB shell (30) has an integrated motor (motor) for agitating the culture. This is compatible with the controller systems of FIG. 36. The single-use bioreactor has an agitator, a sparger, a gas filter inlet ports for sparger, and an exhaust gas outlet filter port with bifurcating line. It also has seven feed addition ports. Ideally, two are subsurface discharging in the impeller region and one discharging above the impeller region. It also has two medium fill ports, one harvest port designed to enable harvest the complete contents of the single-use bioreactor, one sample port, one condenser or equivalent on the gas exit line, and at least six measurement probe ports. These sample and harvest ports have animal derived component free (ADCF) C-flex tubing to enable aseptic connection for addition and removal of liquids. In addition, it has gas filters.

It is also preferable to have a fill line or lines directed such that the liquid flows down the side of the SUB to avoid splashing and foaming during the fill operation.

Example 2

Reactor Geometry

This example relates to the effect of changing reactor geometry on scale up of mammalian cell culture processes using multivariate data analysis to compare different geometries and different fill volumes. This approach uncovered a surprising result when working at half volume, which may not have been spotted using conventional data analysis methods.

Mass transfer studies were performed with two manufacturing scale SUB systems and a miniature SUB system using the gassing-out approach. A scale independent $k_La O_2$ model developed according to the geometry described in U.S. Publication No. US 2011/0312087 (referred to herein as "Lonza Geometry") was used to predict $k_La O_2$ in both SUBs. The results have been compared to results generated using the STR geometry described in U.S. Publication No. US 2011/0312087 from 10 to 20,000 L. The vessel geometry has a substantial impact on mass transfer.

Multivariate analysis of the data showed that there were substantial differences in cell culture performance between different STR-scaled vessels. The results of this testing are presented in FIGS. 11-35.

Figure 11:
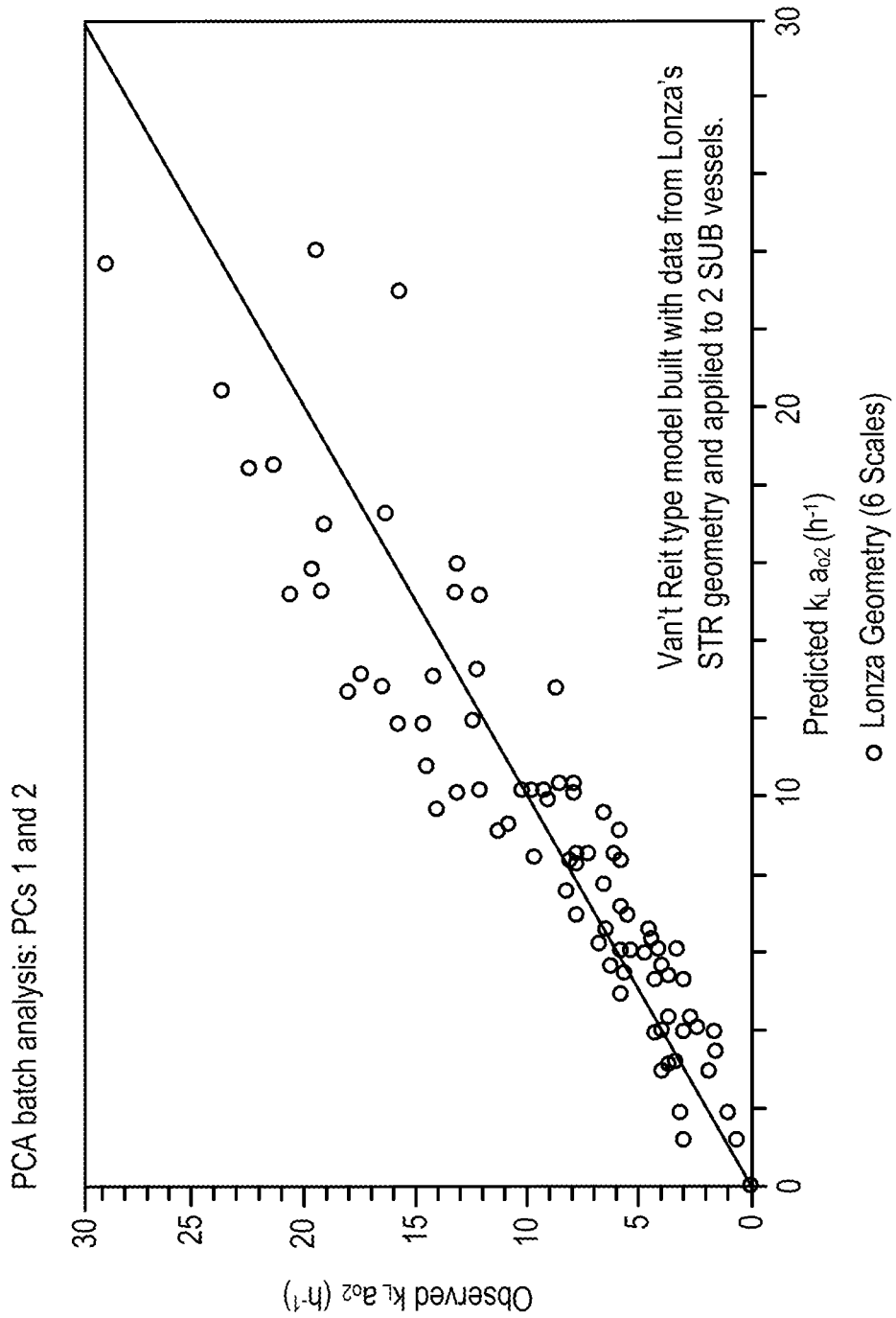
FIG. 11 is the Principle Component Analysis (PCA) in batch mode of PCs 1 and 2 with data from STR geometry.

As described herein, FIG. 11 shows the results of a comparison of the Van't Reit model built with data from single-use bioreactors that were designed at least partially according to the geometry described in U.S. Publication No. US 2011/0312087 at six different scales.

Figure 12:
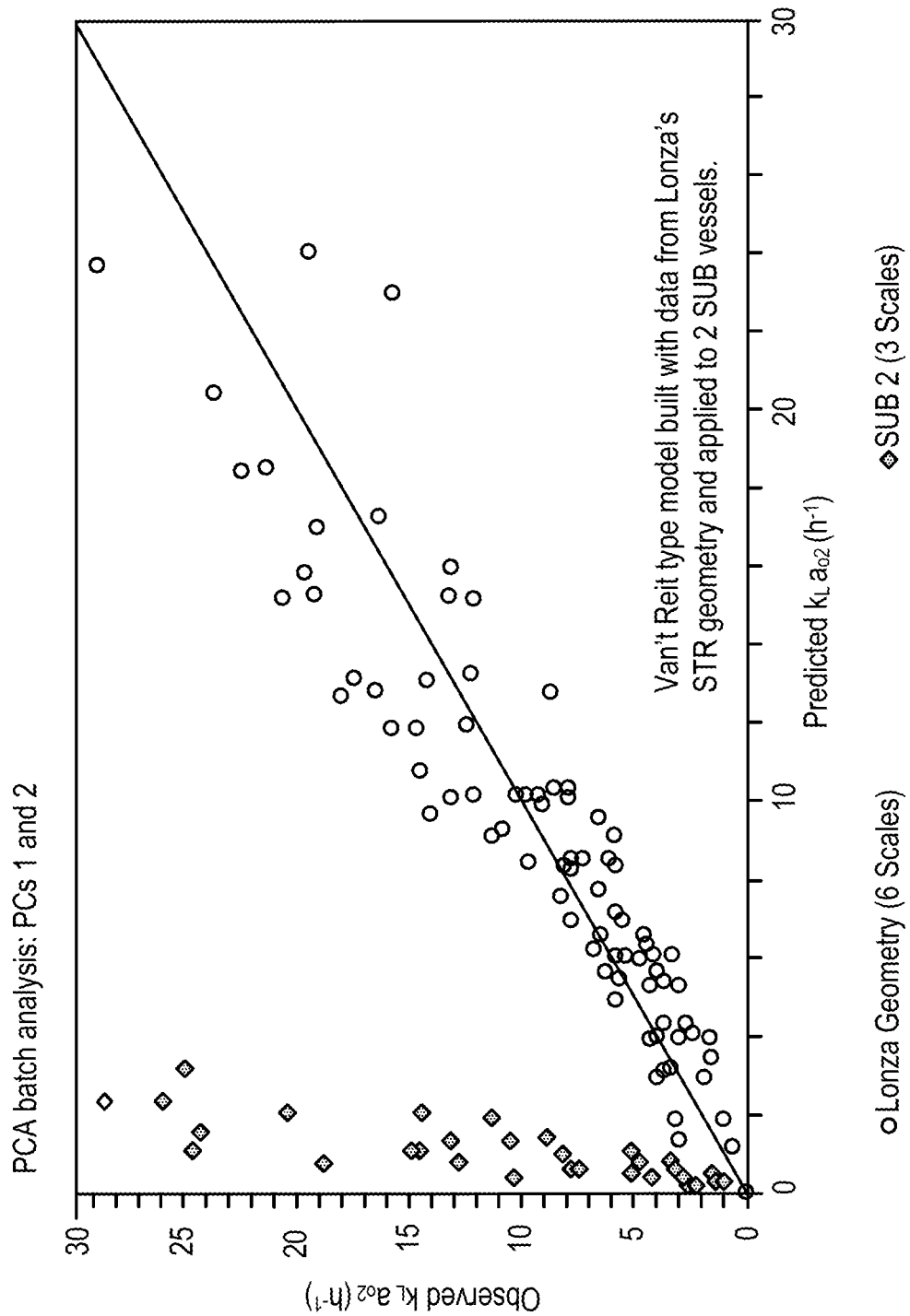
FIG. 12 is the Principle Component Analysis (PCA) in batch mode of PCs 1 and 2 with data from STR geometry and SUB 2.

As described herein, FIG. 12 shows the results of a comparison of the Van't Reit model built with data from single-use bioreactors that were designed at least partially according to the Lonza Geometry at six different scales as compared to a single-use bioreactor that did not incorporate the Lonza Geometry (red diamonds).

Figure 13:
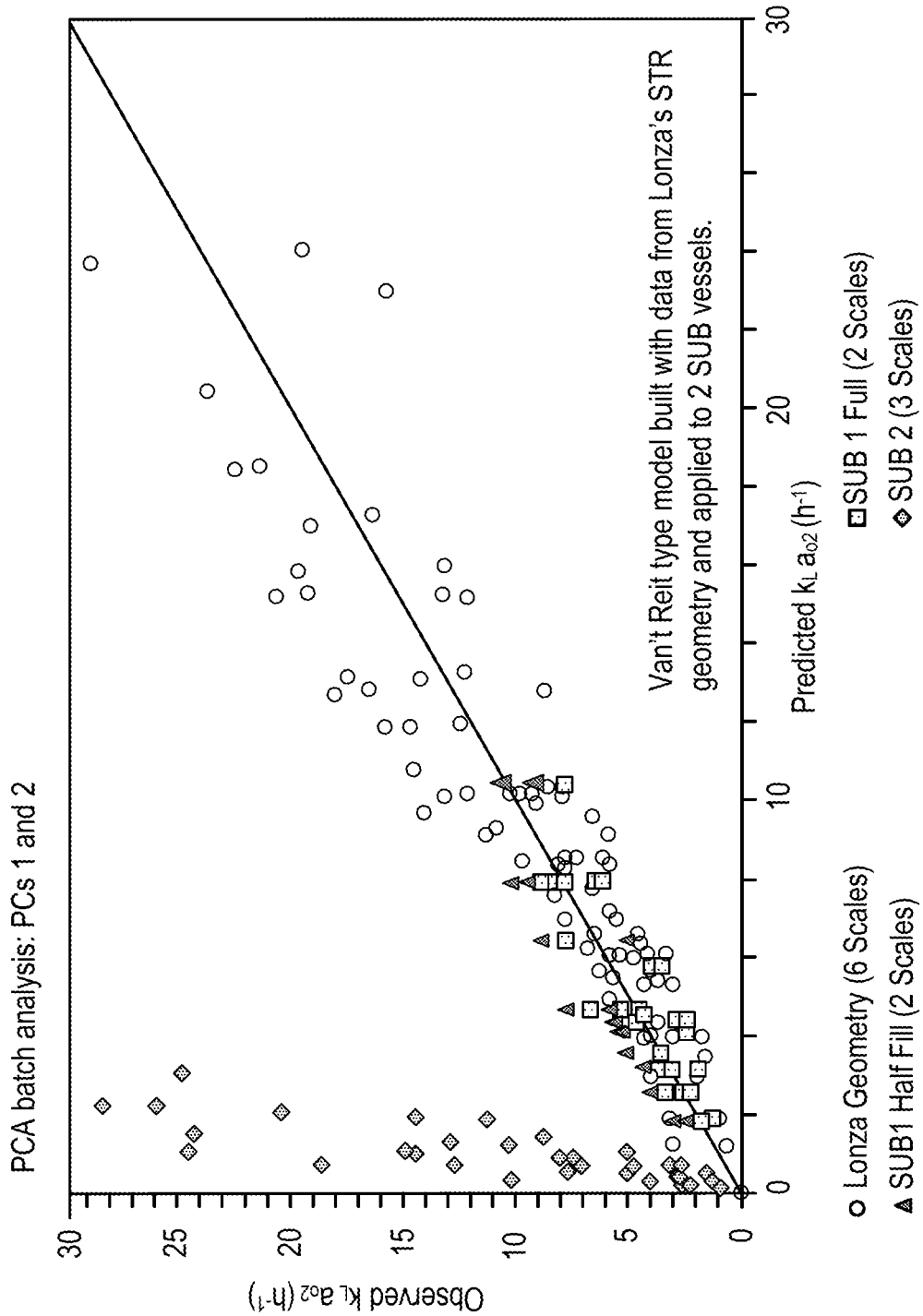
FIG. 13 is the Principle Component Analysis (PCA) in batch mode of PCs 1 and 2 with data from STR geometry, SUB 1 (full and half fill) and SUB 2.
Figure 14:
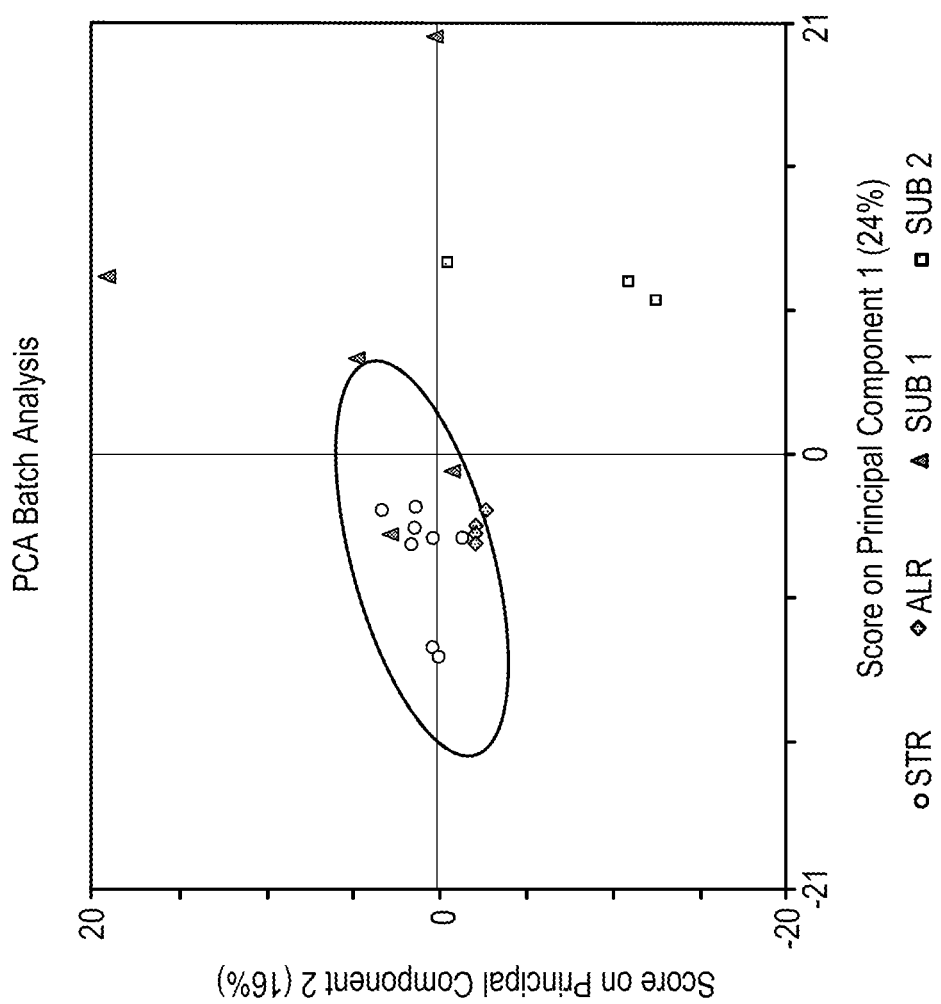
FIG. 14 shows the score on Principle Component 1 and 2.

As described herein, FIG. 13 shows the results of a comparison of the Van't Reit model built with data from single-use bioreactors that were designed at least partially according to the Lonza Geometry at six different scales as compared to a single-use bioreactor that did not incorporate the Lonza Geometry (red diamonds), two single-use bioreactors at two different scales built at least partially according to the Lonza Geometry when half full (blue triangles), and two single-use bioreactors at two different scales built at least partially according to the Lonza Geometry when full.

Figure 15:
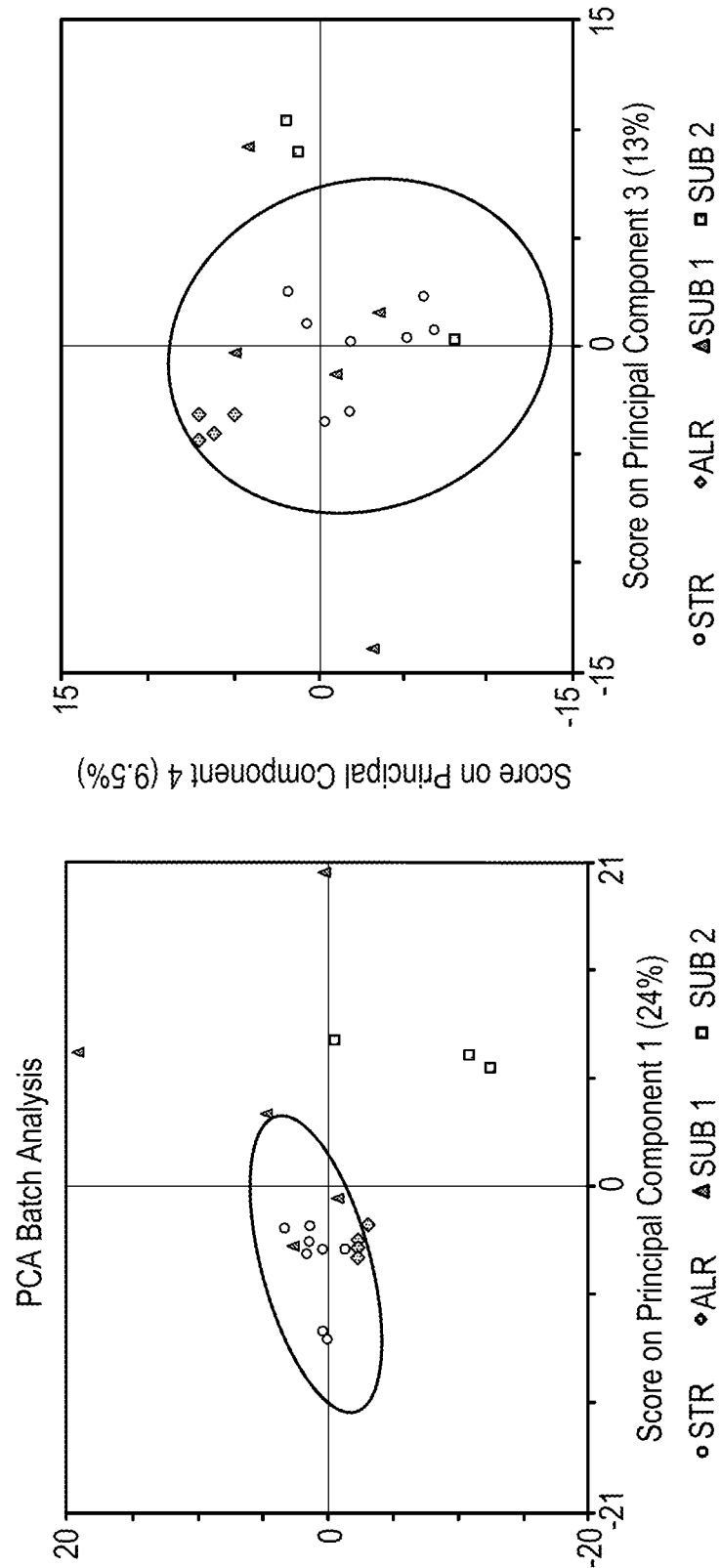
FIG. 15 shows the first 4 principal components (PC)s of the BS matrix captured 63% of the variance in the data set.
Figure 16:
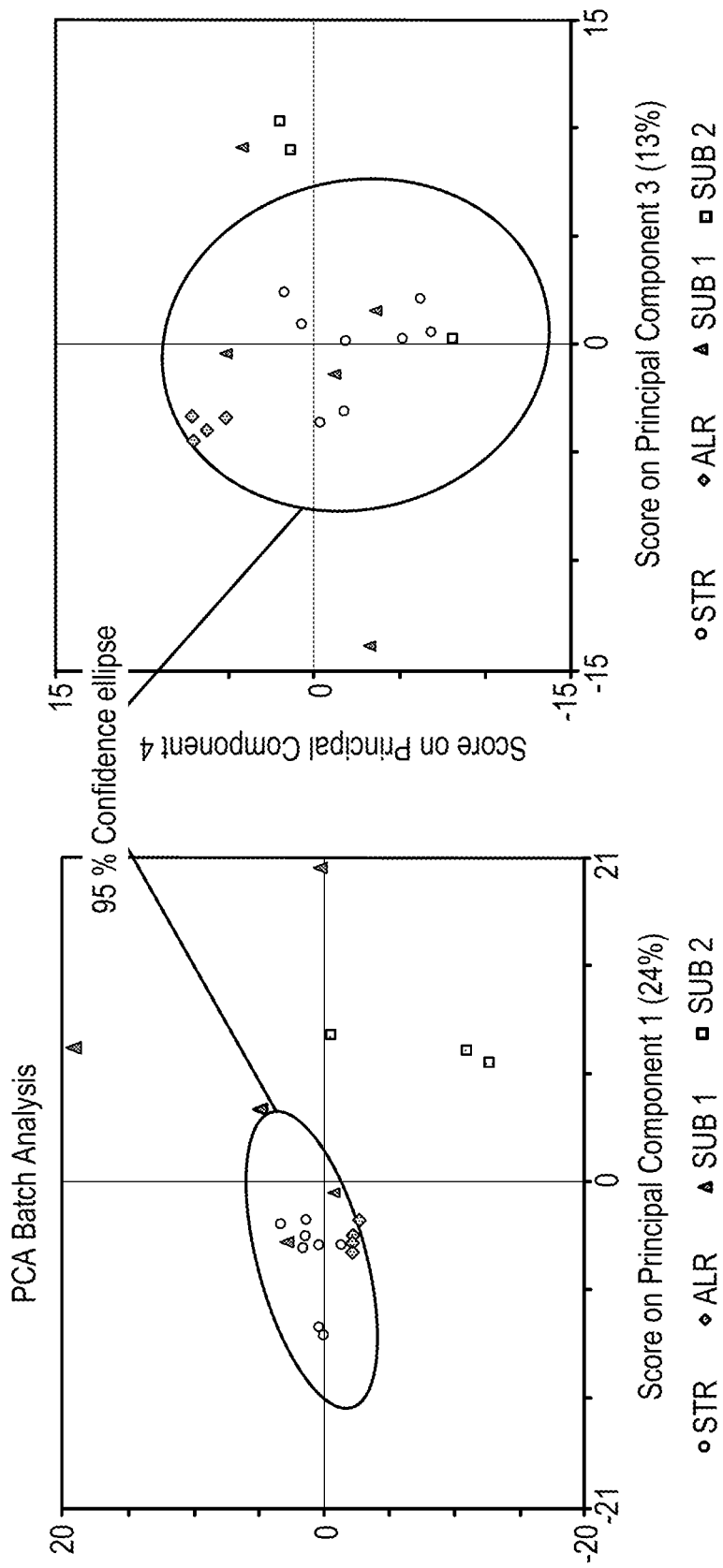
FIG. 16 shows the Principle Components Scores with 95% Confidence Intervals.
Figure 17:
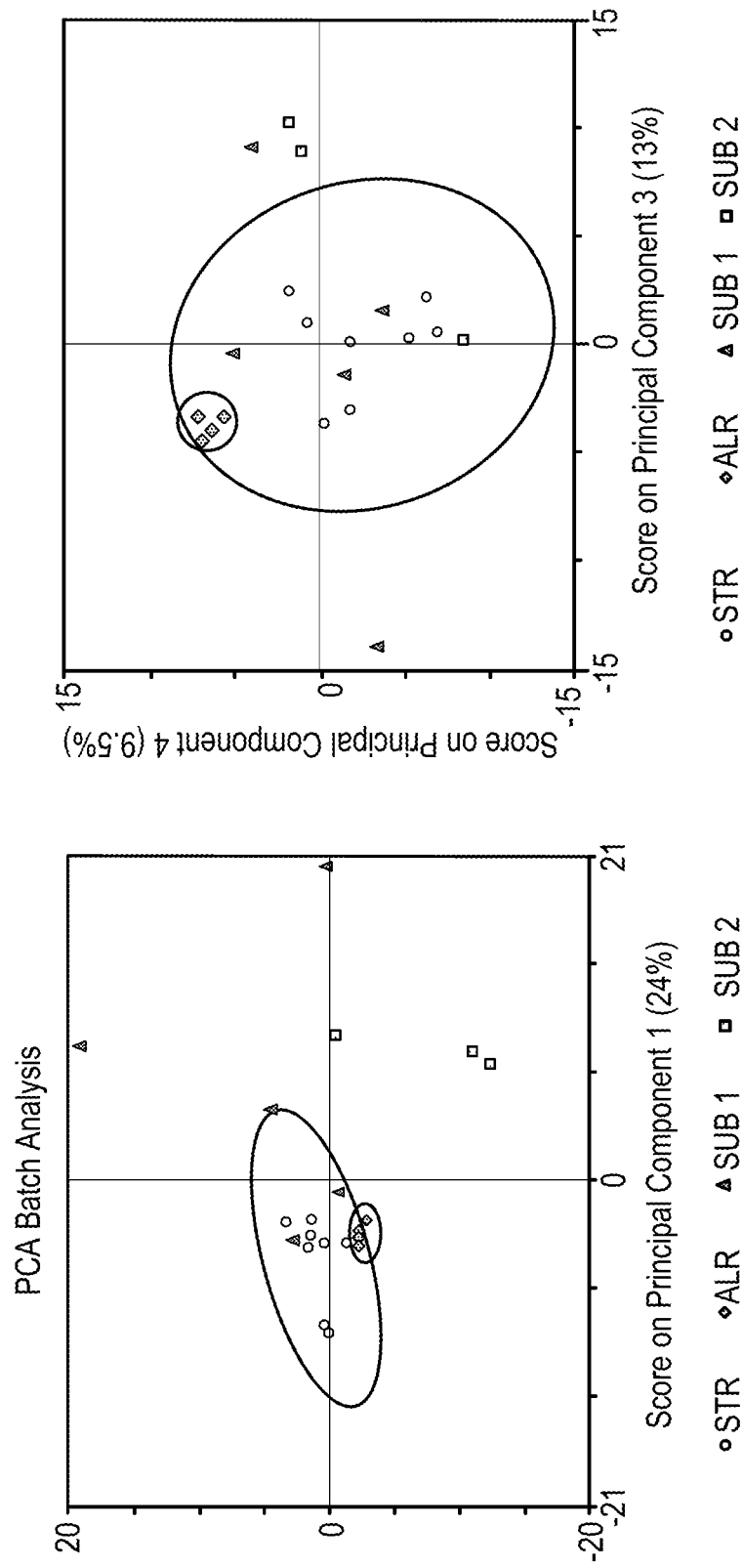
FIG. 17 shows the Principle Components Scores of ALR and STR Cultures performed at Three Scales.

Cell culture evaluations were also performed with a model cell line in the two single-use bioreactor systems discussed above and one stainless steel/glass. The results were compared to historical data obtained in 10 L STR and 10 L airlift vessels ("ALR"). A total of fifteen measurements were taken for sixteen days in all four of the vessel geometries. The data were analyzed using the principal component analysis which projects high dimensional data sets onto lower dimension space to aid in data interpretation. Principal component analysis (PCA) and the calculation of associated statistics was performed in MATLAB Version 7.11.0.584 (The MathWorks Inc) using the PLS Tool Box Version 6.2 (Eigenvector Research, Inc.). The results are summarized in FIGS. 14, 15, and 16. These data show that the first four principal components captured 63% of the variance of the dataset, as shown in FIG. 15. The cell cultures performed similarly in the ALRs, the STRs, and SUB1 at full volume. However, SUB2, which does not possess Lonza's geometry, performed outside the 95% confidence interval, as shown in FIG. 16. Furthermore, ALRs and STRs performed similarly in principal components one, two, and three, as shown in FIG. 17.

Figure 18:
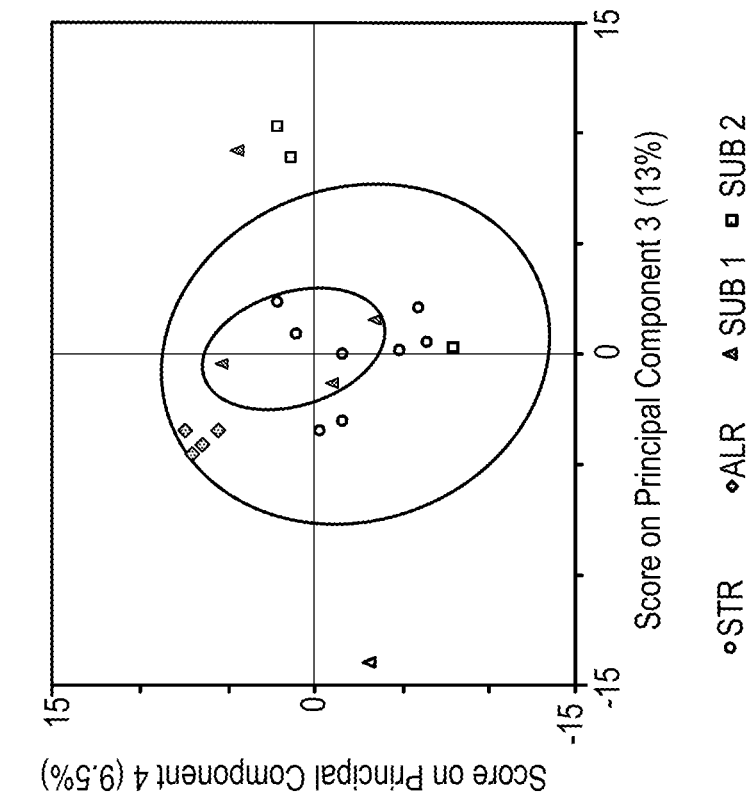
FIG. 18 shows the Principle Components Scores of SUB 1 Cultures performed at Three Scales with Two Fill Volumes.
Figure 18:
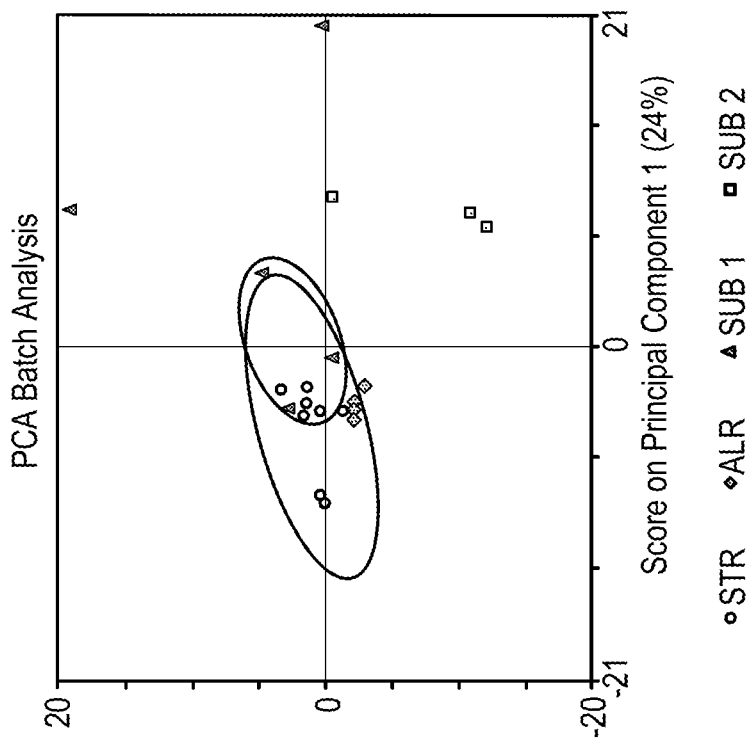
Figure 19:
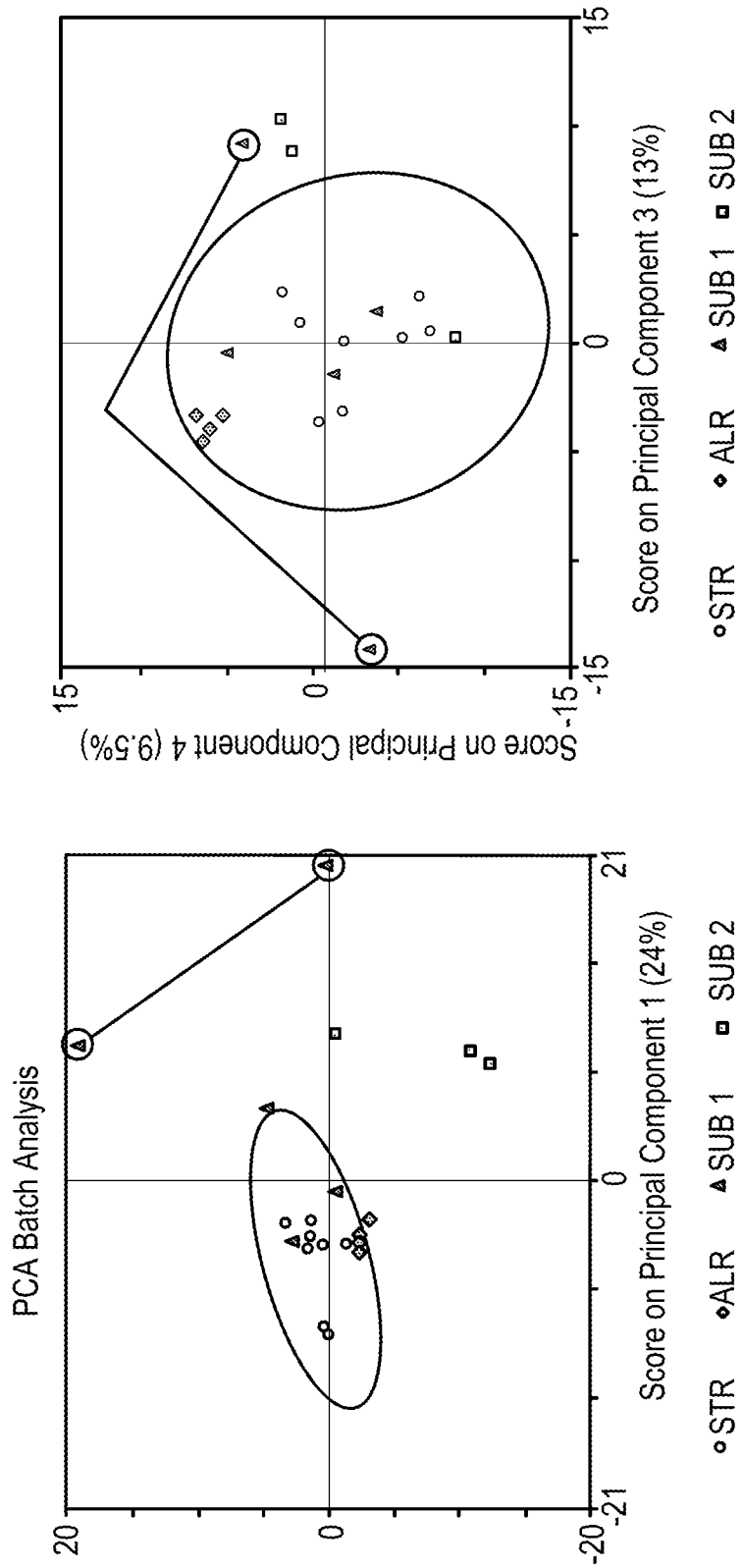
FIG. 19 shows the Principle Components Scores of SUB 1 Cultures performed at Three Scales with Two Fill Volumes Depicting Outliers.
Figure 20:
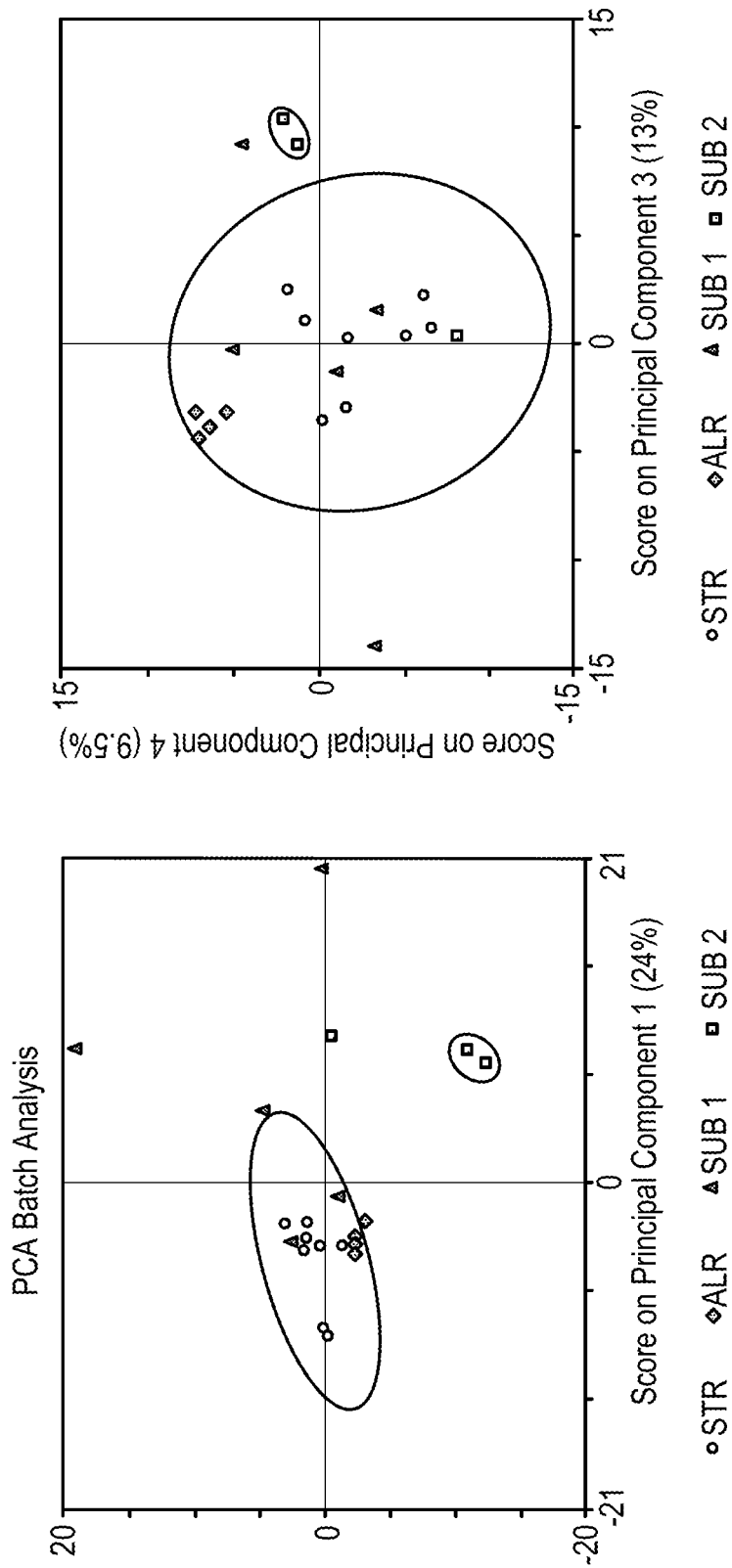
FIG. 20 shows the Principle Components Scores of SUB 2 Cultures performed at Three Scales with Two Bioprocess container Materials—New Bioprocess container Data Highlighted.
Figure 21:
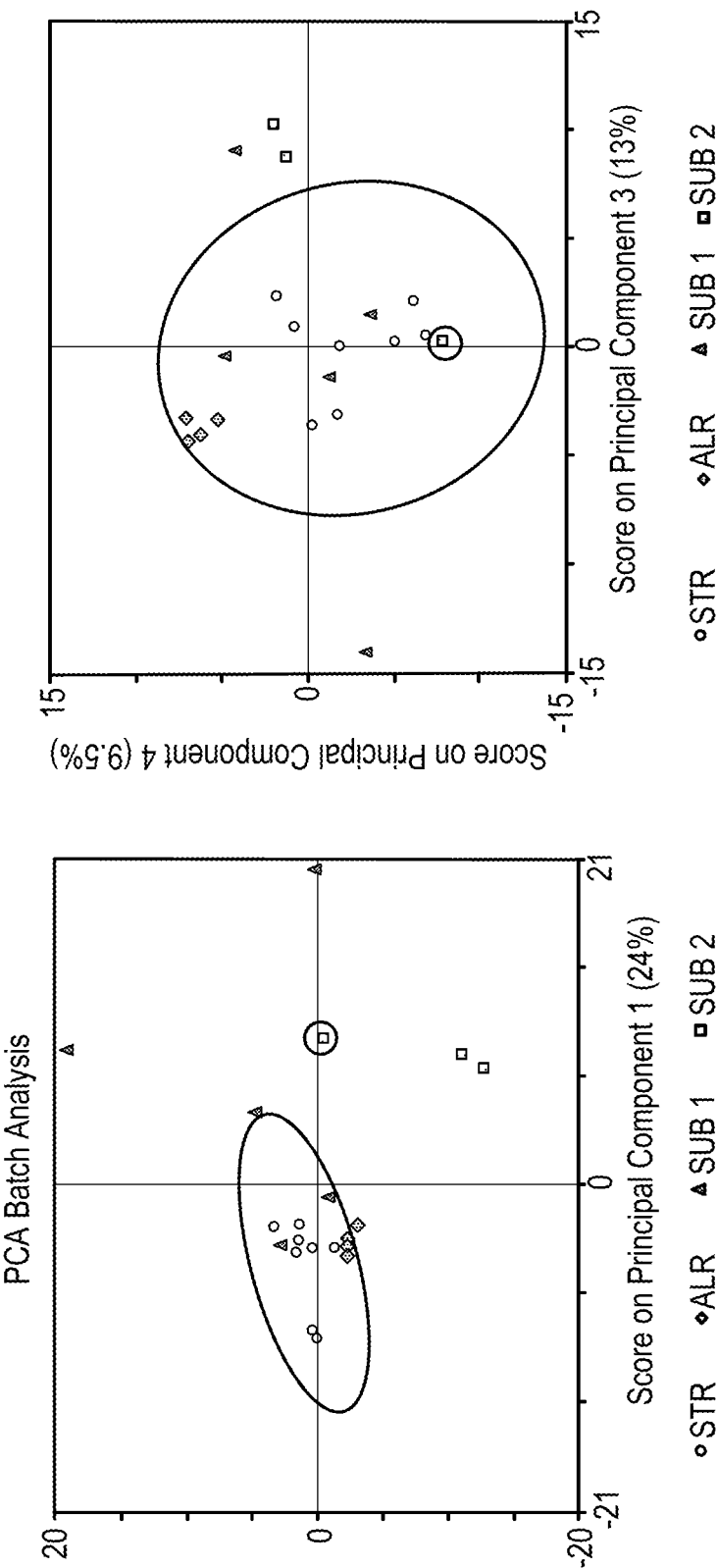
FIG. 21 shows the Principle Components Scores of SUB 2 Cultures performed at Three Scales with Two Bioprocess container Materials—Old Bioprocess container Data Highlighted.
Figure 22:
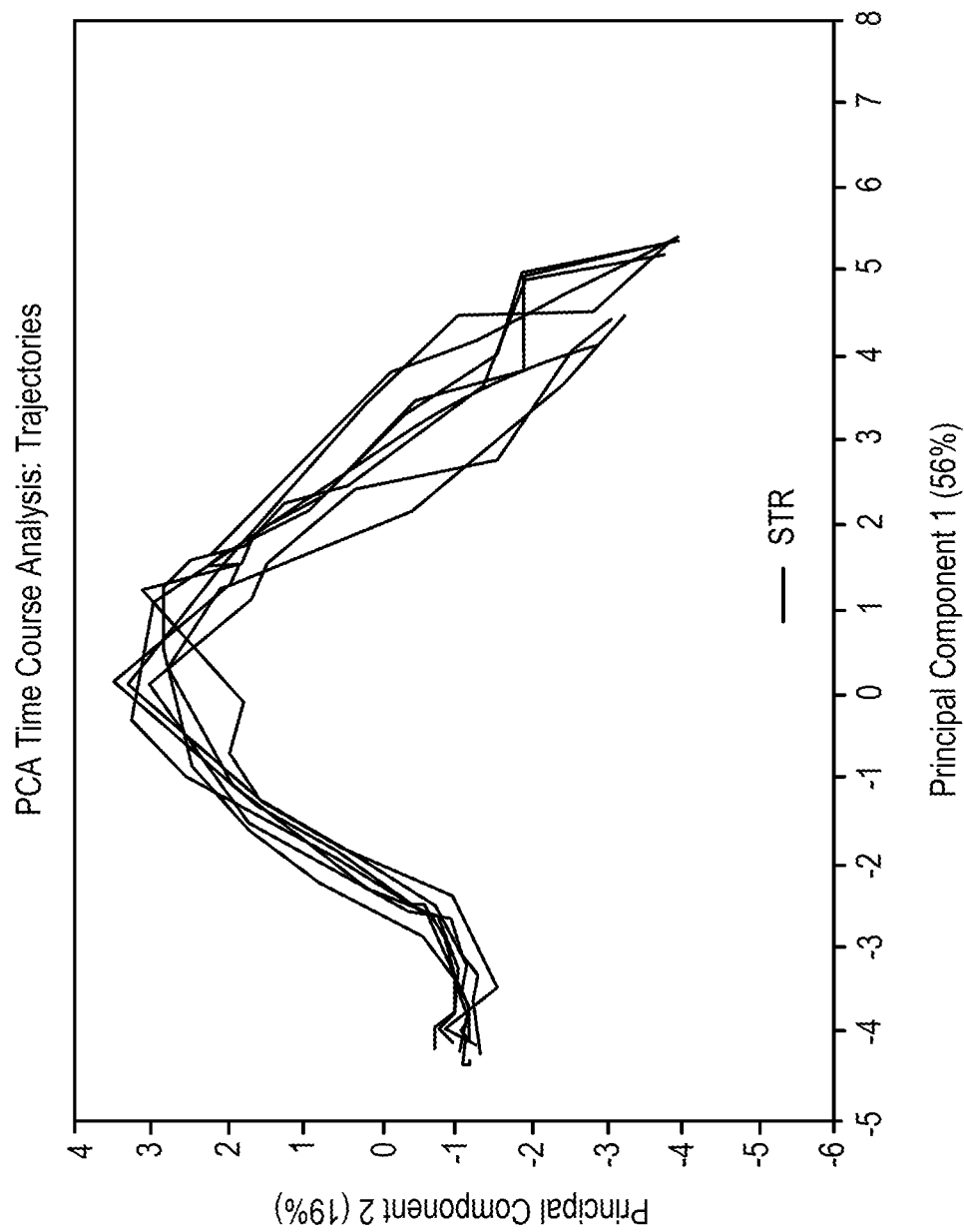
FIG. 22 shows the Principle Components Scores Plots of Data from Cultures Performed in Four Vessel Designs of STRs.
Figure 23:
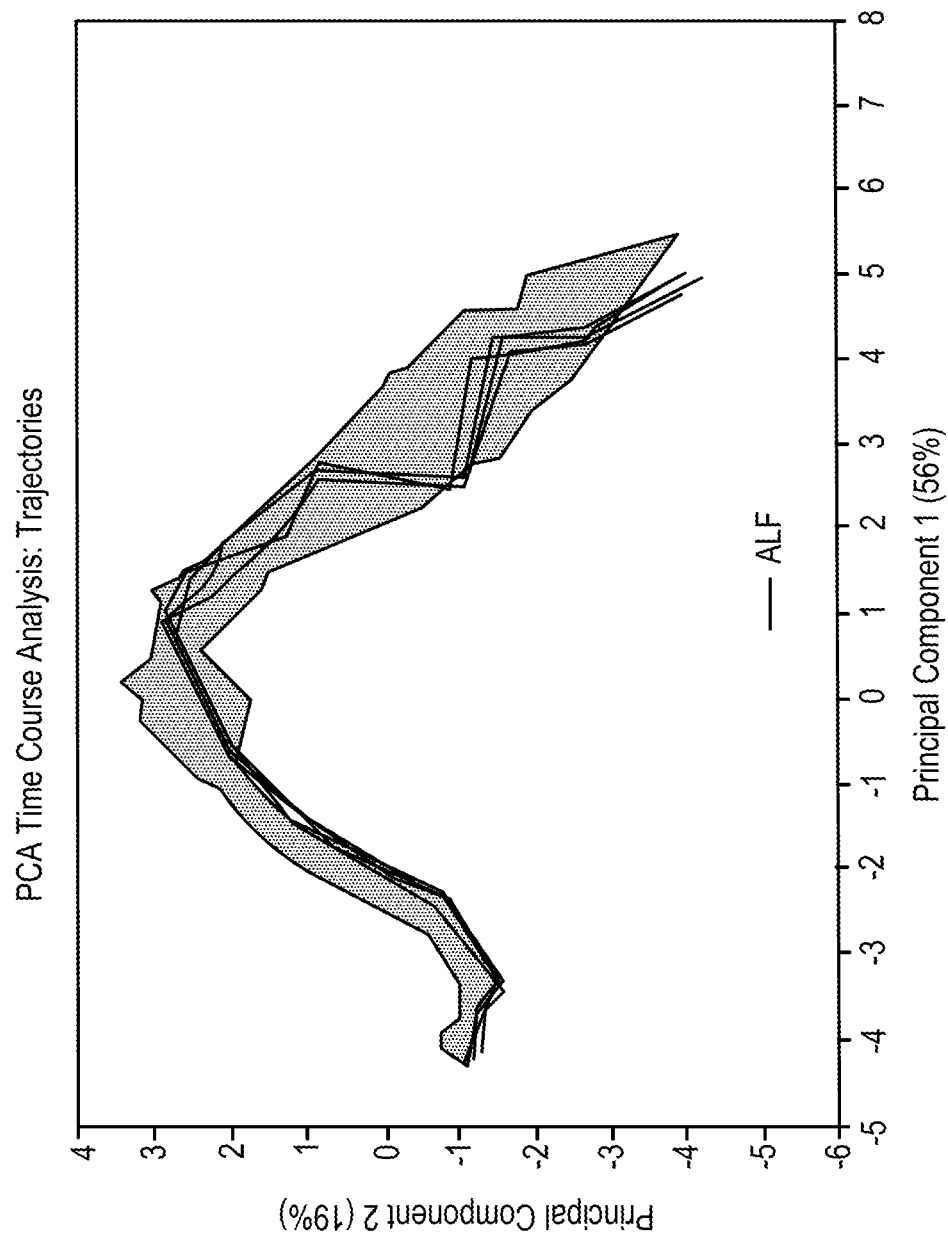
FIG. 23 shows the Principle Components Scores Plots of Data from Cultures Performed in Four Vessel Designs of ALRs.
Figure 24:
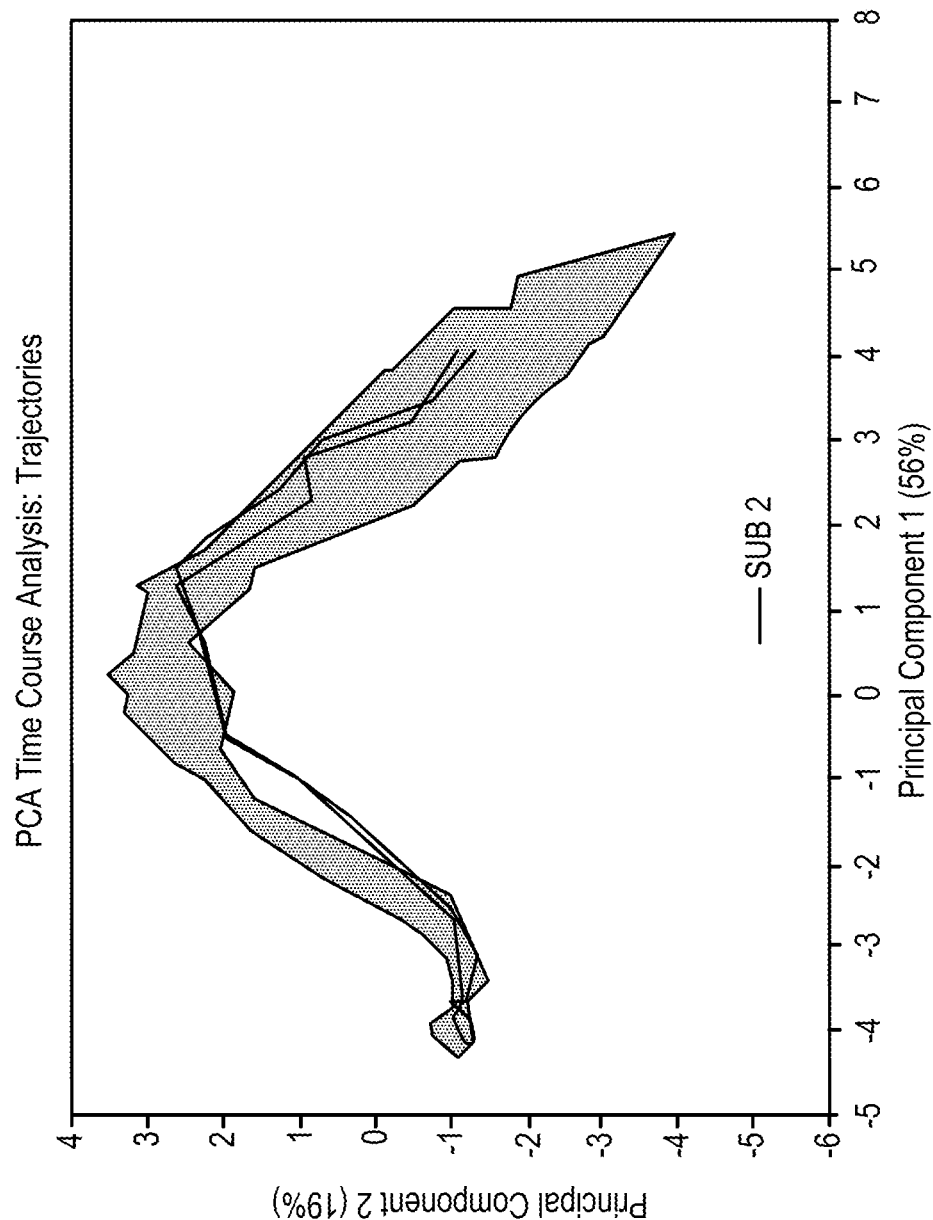
FIG. 24 shows the Principle Components Scores Plots of Data from Cultures Performed in Four Vessel Designs of SUB 2.
Figure 25:
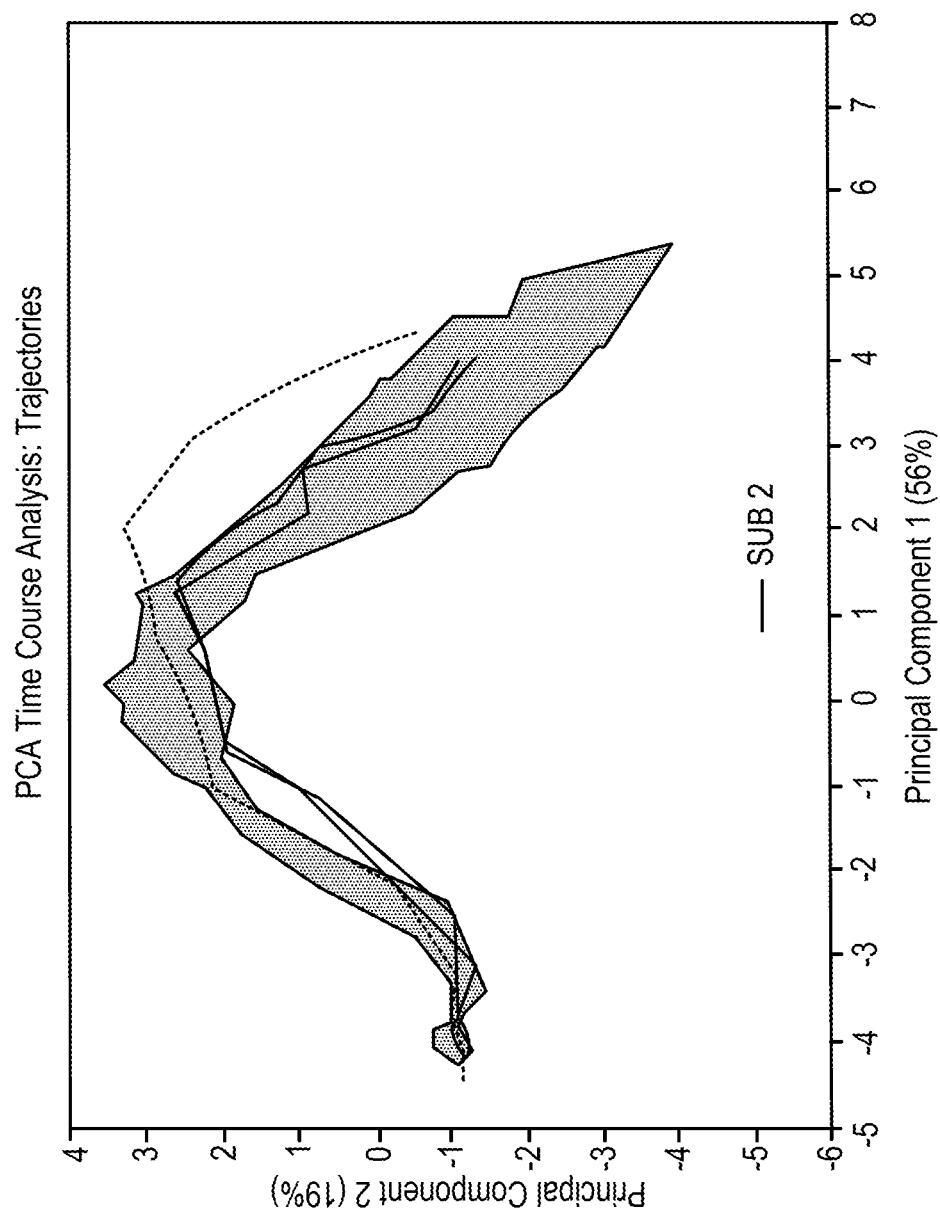
FIG. 25 shows the Principle Components Scores Plots of Data from Cultures Performed in Four Vessel Designs of SUB 2 with New Bioprocess container Material.
Figure 26:
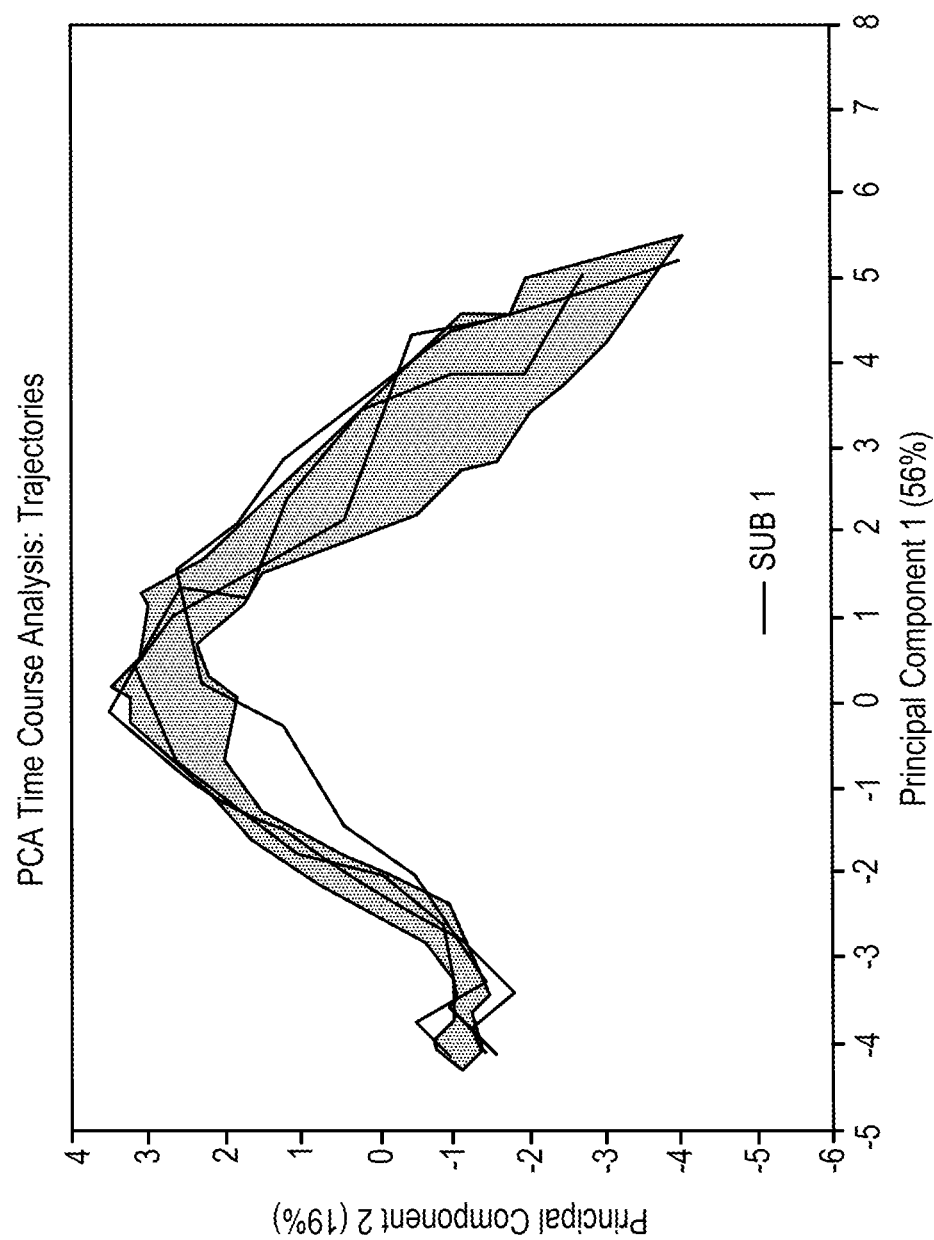
FIG. 26 shows the Principle Components Scores Plots of Data from Cultures Performed in Four Vessel Designs of SUB 1.
Figure 27:
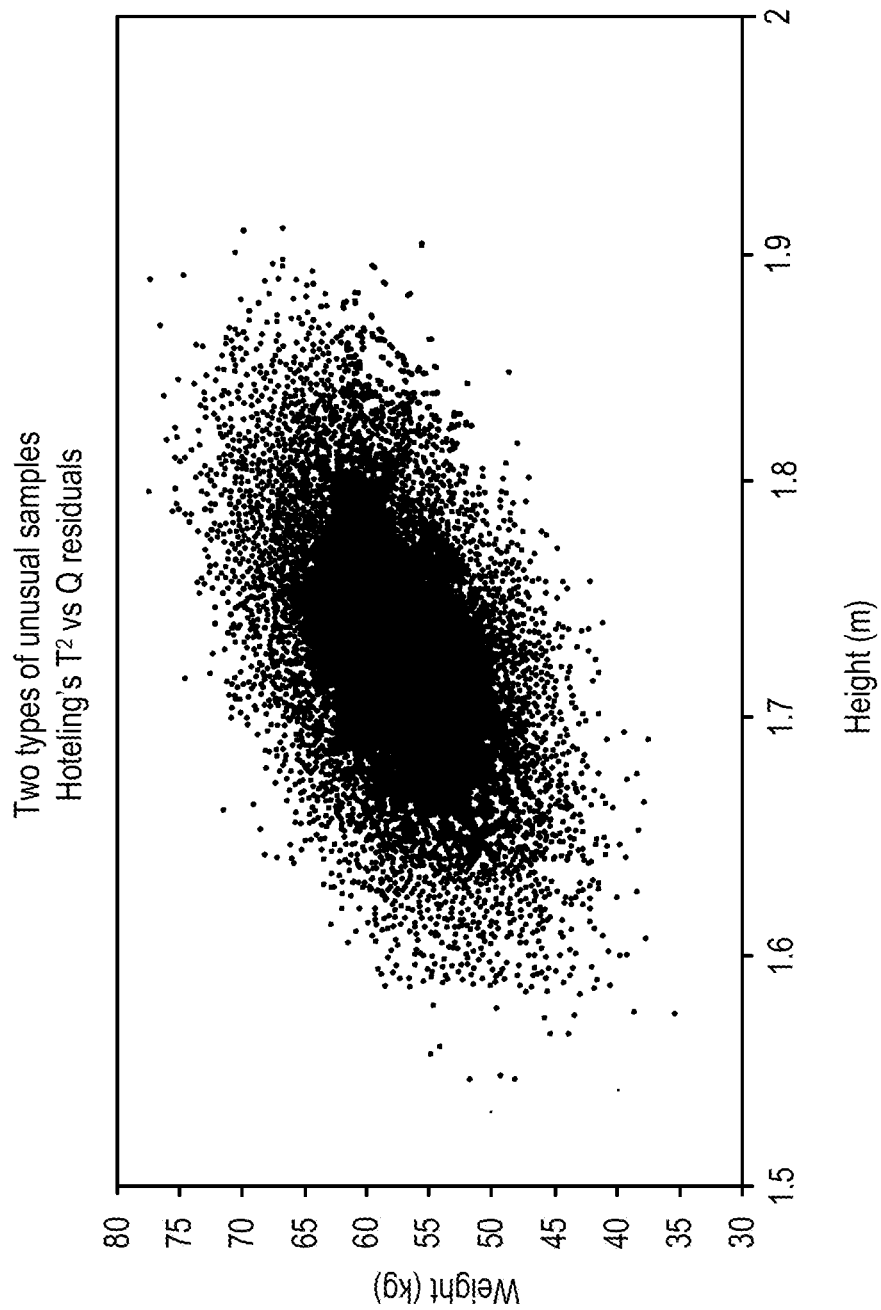
FIG. 27 shows the Hoteling's T2 vs Q residuals.
Figure 28:
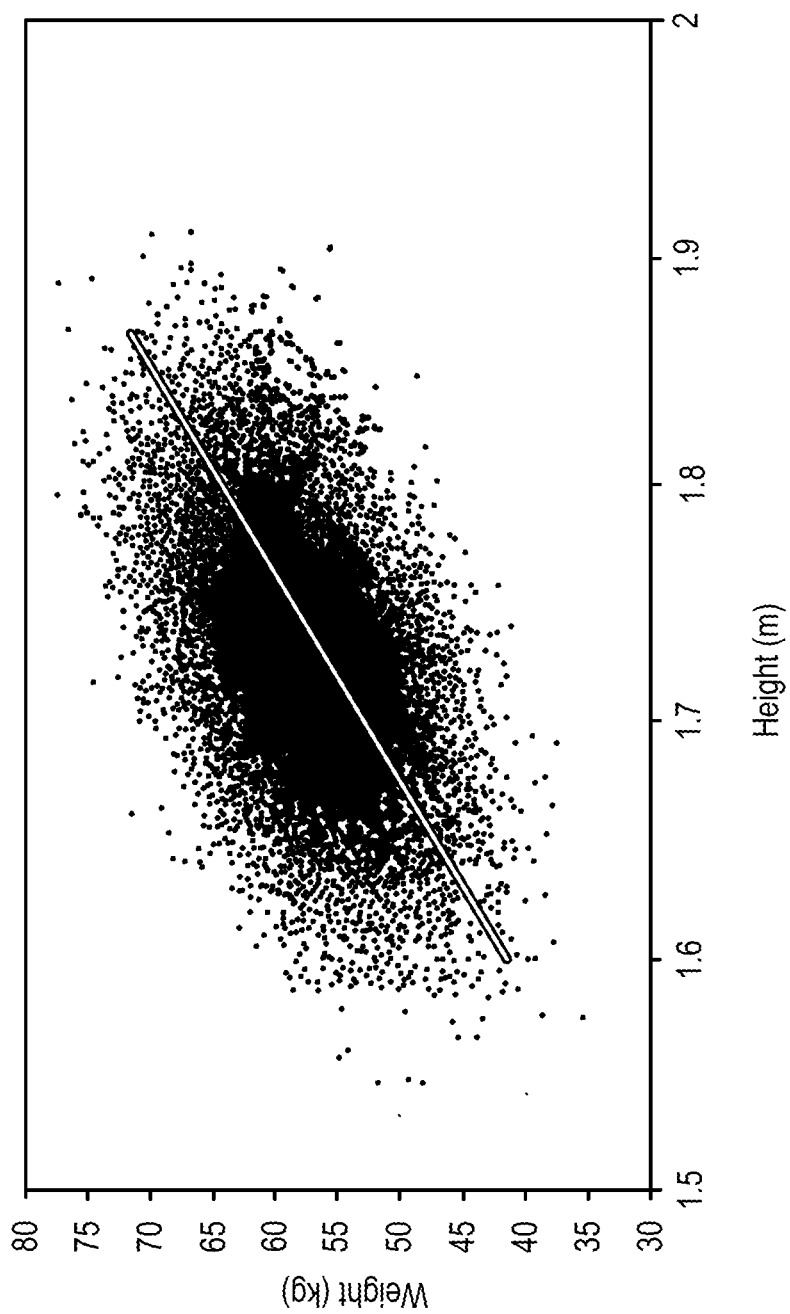
FIG. 28 shows a graph showing Height vs. Weight.
Figure 29:
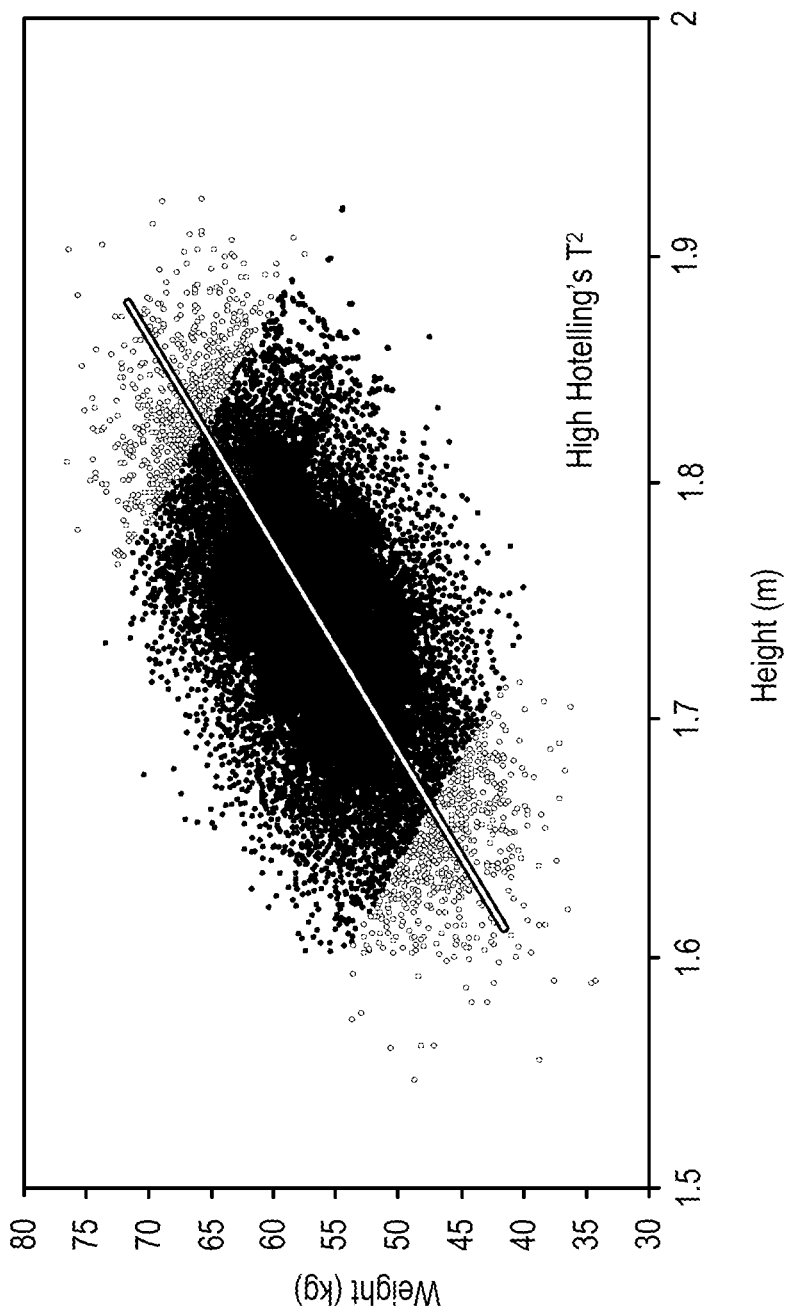
FIG. 29 is a graph showing High T2 Statistics.
Figure 30:
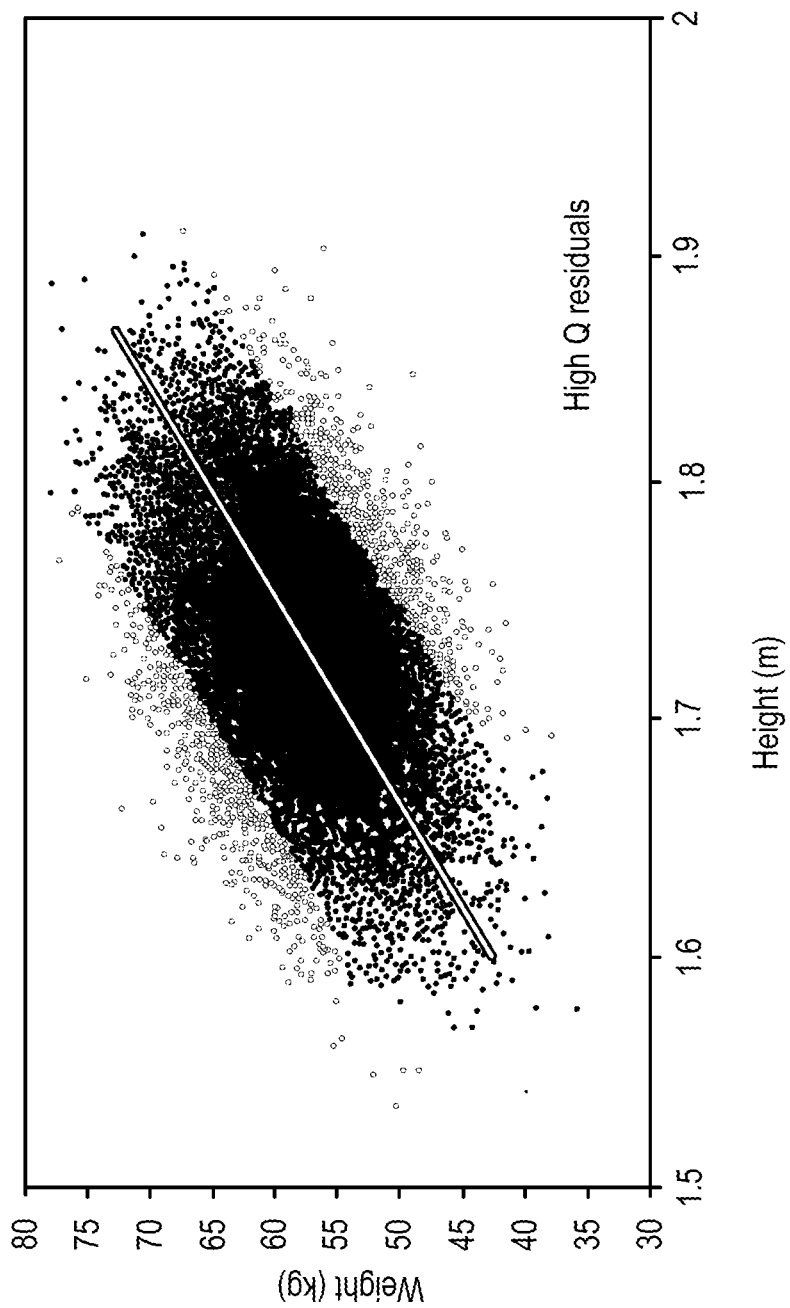
FIG. 30 is a graph showing High Hoteling's.
Figure 31:
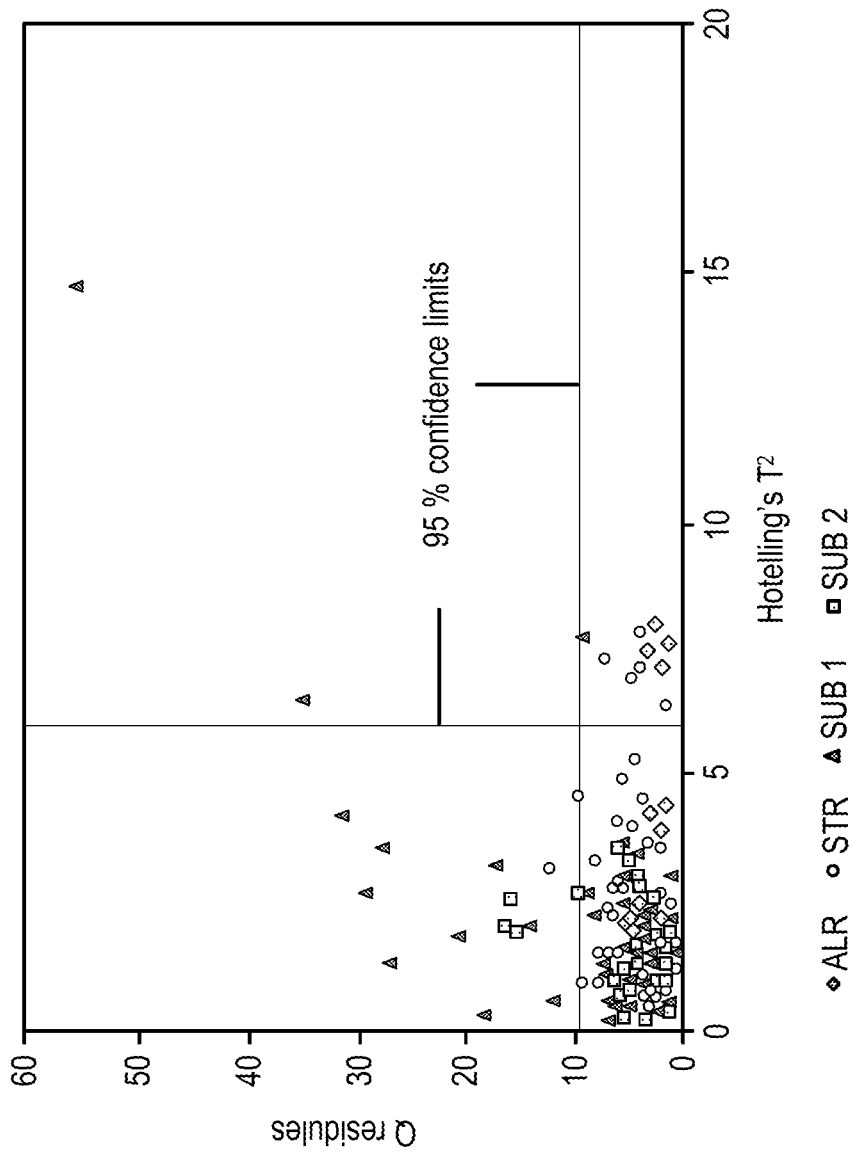
FIG. 31 is a graph showing Hoteling's T2 Statistic and Q Residuals for the Model generated using the Trajectory Approach.
Figure 32:
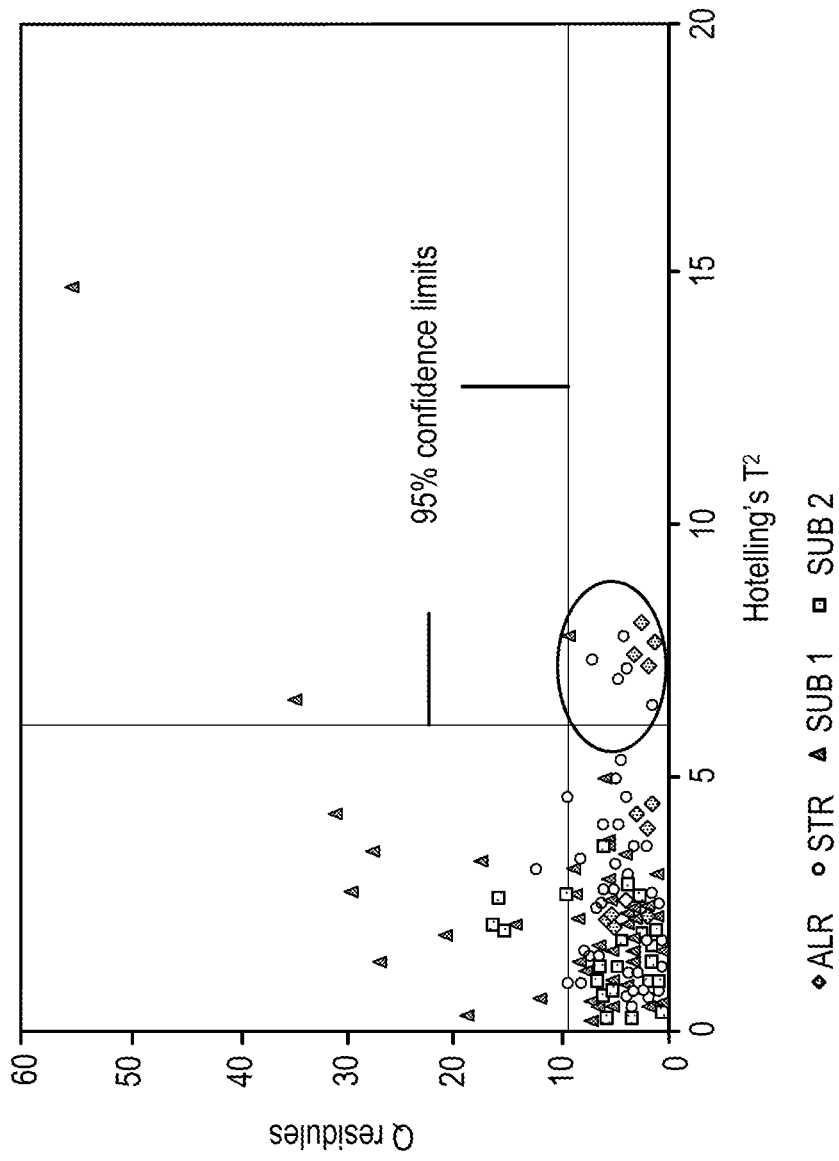
FIG. 32 is a graph showing Hoteling's T2 Statistic and Q Residuals for the Model generated using the Trajectory Approach Focusing on STR and ALR.
Figure 33:
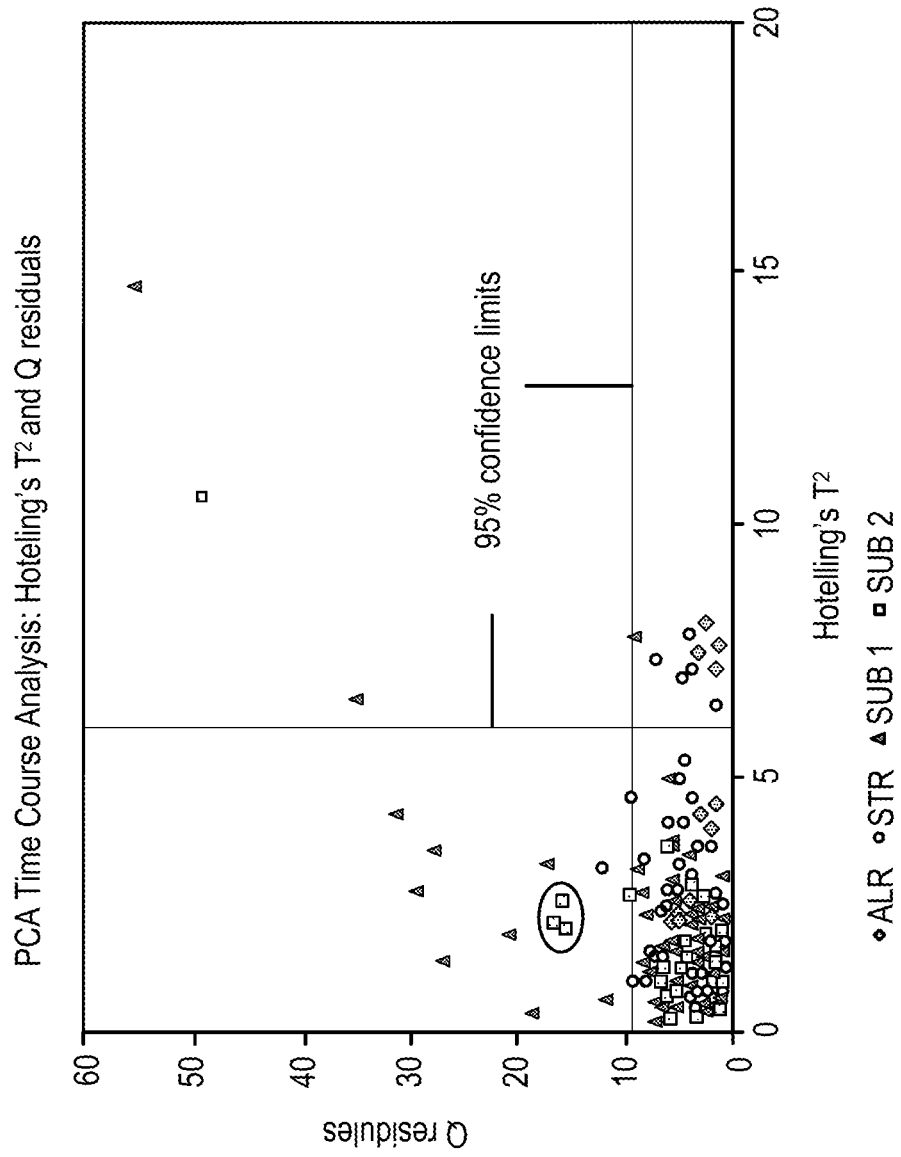
FIG. 33 is a graph showing Hoteling's T2 Statistic and Q Residuals for the Model generated using the Trajectory Approach focusing on SUB 2.
Figure 34:
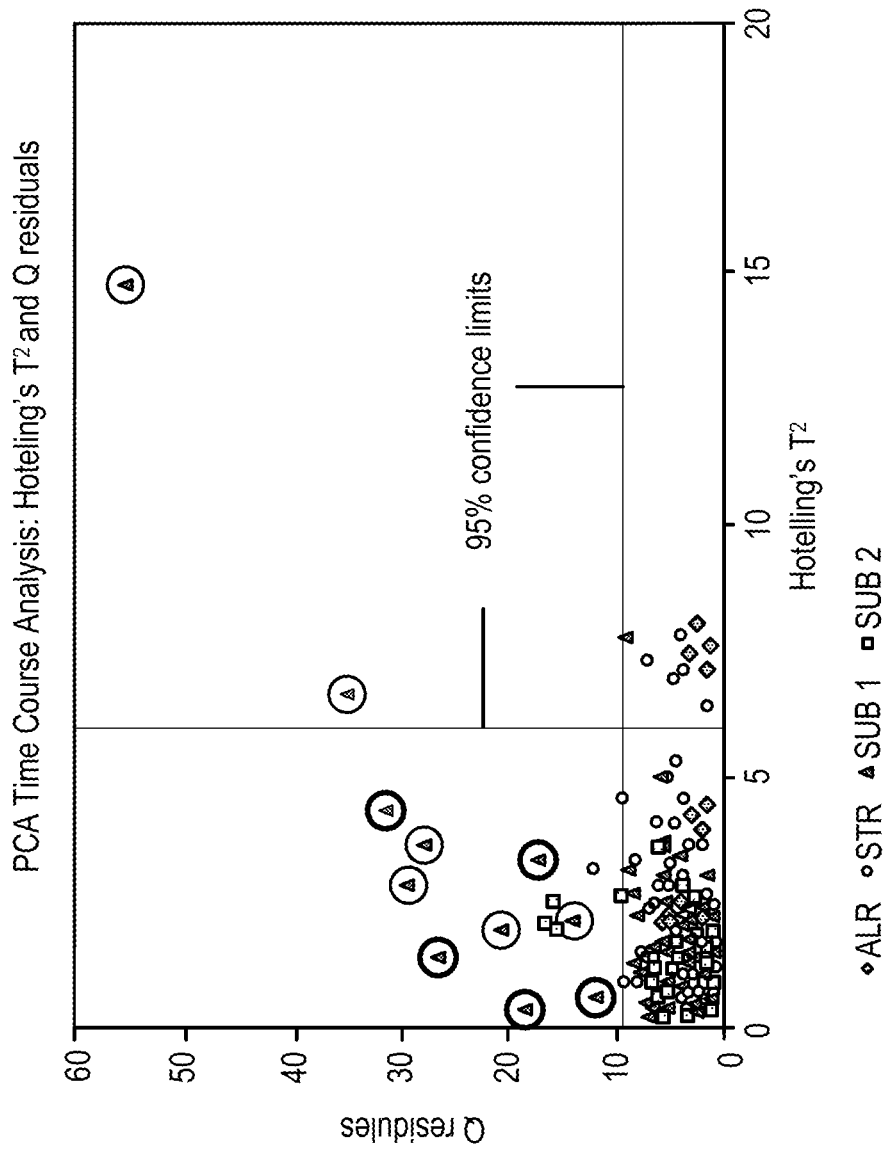
FIG. 34 is a graph showing Hoteling's T2 Statistic and Q Residuals for the Model generated using the Trajectory Approach.
Figure 35:
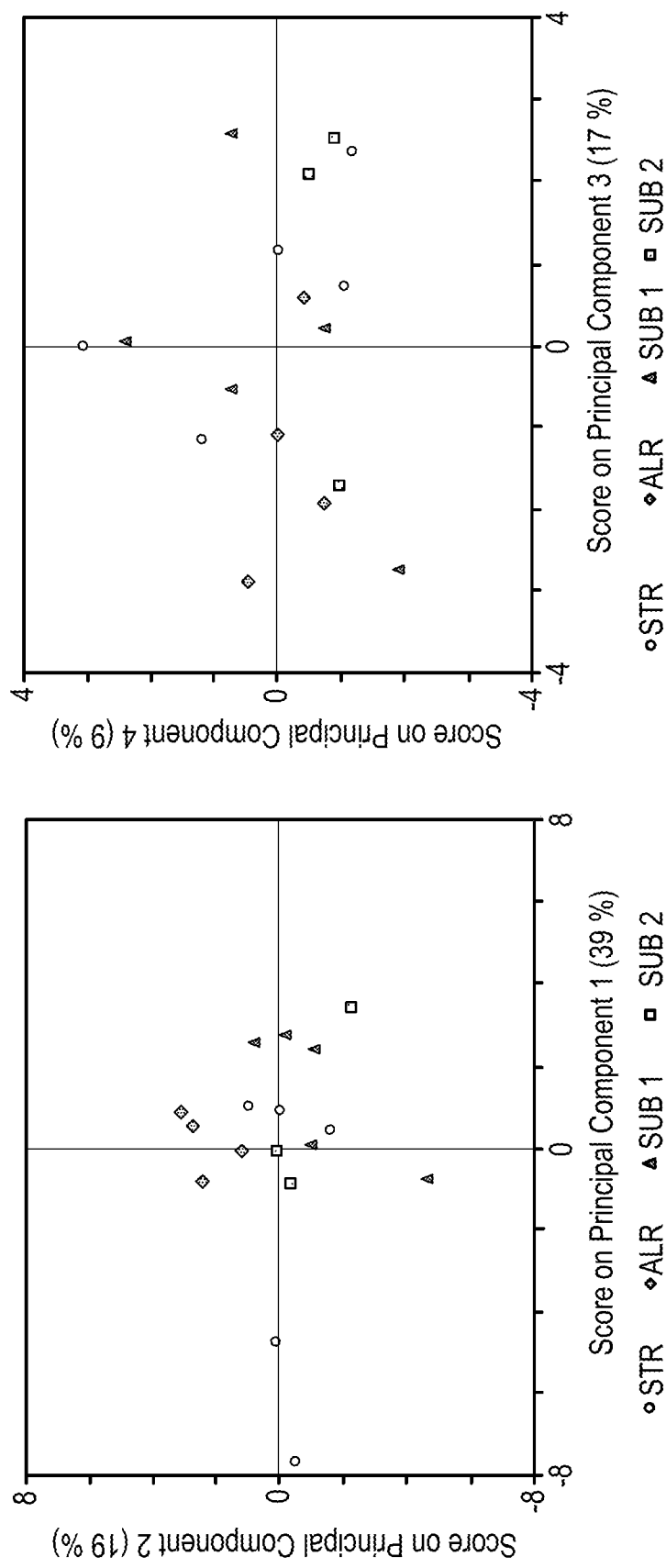
FIG. 35 are the Scores Plots from Principal Component Analysis of the Product Characteristics Data of Principal Components 2 and 4.

The impact of operating at half volume was investigated for one vessel design at two different vessel volumes, as shown in FIGS. 18-19. Here, the data show that the cultures in SUB1 at two scales, which contains at least partially Lonza's geometry, performed similarly at full volume with the STR cultures on all principal components. However, when at half volume, that those same SUB at two scales displayed substantial differences in performance on the first three principal components indicates dissimilarity in culture properties.

Multivariate data analysis showed that there was considerable difference in behavior of the cultures performed at half volume when compared to cultures performed in the conventional scale-down model. For example, in FIGS. 20-21, cultures in SUB2 were performed at three scales with two bioprocess container materials.

The experiments conducted in Example 2 highlight the importance of bioreactor design, including the single-use bioreactors that are the object of the present disclosure. For example, loadings for principal component one normally track growth and/or culture progression. Loadings for a model built with STR data alone followed this norm. However, when the tests were expanded to include all four vessels designs of ALR, STR, SUB1, and SUB2, growth and/or culture progression was relegated to principal component two.

Additionally, Example 2 shows that geometric similarity is indicative of performance. The analysis indicated that there was also a difference in behavior of the half-volume cultures in different size vessels. Specifically, SUB 1 and STR cultures cluster well at full volume but not at half volume. At full volume, SUB 1 has a high degree of geometric similarity to the STR. However, at half volume, just one of these geometric parameters has been altered. Furthermore, culture performance was radically altered. Interestingly, Lath performance was not altered. Half-volume SUB1 's performance was not consistent across scales as shown by the data where half volume cultures don't form a cluster.

Furthermore, the selection of bioprocess container material has an impact on SUB 2 culture performance. This is additionally supported by FIGS. 22-35 where the principal components were assessed over time for the various fills, volumes, and bioprocess container materials.

This indicated a lack of scalability between half-volume cultures performed in different scale vessels, which was not apparent when the same vessels were run at full volume.

Single-use bioreactor geometry does matter when scaling processes up and should be a key consideration in a quality by design approach to minimizing differences in culture behavior during cell culture process scale up. Moreover, multivariate data analysis can provide useful supplemental insight in bioreactor process performance comparisons.

Example 3

A 1,000 L Bioreactor Set Up

The single-use bioreactors of the present disclosure are suitable for use in the production processes described in WO 2017/072201 A2, which is incorporated by reference in its entirety herein.

The bioprocess container shell was a jacketed stainless steel container, which supported the SUB container. The shell incorporated two doors that open outwards for operators to fit the SUB bioprocess container. These were fastened shut by clamps. The shell incorporated a water jacket at the bottom for regulation of temperature. This was connected to the controller of the present disclosure.

At the bottom of the shell there was a drain port for harvesting and two openings for control probes and sampling. For non-disposable probes the shell had shelving set at 15 degrees from horizontal to support the probes.

At the top of the bioprocess container holder there was a motor to which the SUB container impeller was connected via a magnetic coupling. The motor attached to the 200 liter shell could be moved, but in the motor attached to the 1000 liter shell was fixed. There was a gas filter holder, pressure sensor and manual pressure relief valve situated on the arm of the motor.

The SUB bioprocess container incorporated a pressure release valve which actuated if pressure exceeded 100 mbar. Both the pressure transmitter and the relief valve were connected to the SUB container via a 0.22 um filter.

The controller of the present disclosure contained: two Watson Marlow pumps one for acid and one for base control, rotameters for control of gas flow, a human machine interface (HMI), a thermocirculator and gas mass flow controllers (MFCs) built into the tower. The pH probes, dissolved oxygen tension (DOT) probes, temperature probes, pressure sensor and vent heater were external to but connected to a controller of the present disclosure.

Set points were entered into the HMI screen for all control parameters. The controller used these values to regulate culture temperature, gas flow rates and pump speed. The HMI also displayed current values of all measured parameters.

Temperature measurement was performed using a pt100 probe inserted into a pocket in the SUB container.

Inside the SUB container there was: (i) an agitator shaft with a choice of two impeller designs (see FIG. 1A and FIG. 1B); (ii) disposable optical pH and DOT probes; (iii) a combination sparger (option of micro (0.15 mm) macro (0.8 mm) holes; and (iv) surface and subsurface feed lines.

On the outside of the SUB bioprocess container there were C flex lines for inoculum, medium and feed additions and OPTA connections for gas filters and feed additions. At the bottom of the SUB bioprocess container there were four connections for non-disposable probes, a sample line, and an insert for a pt100 probe. The harvest line was at the bottom of the SUB bioprocess container.

Hydrophobic 0.22 μm gas filters came autoclaved separately and were connected to the SUB bioprocess container using OPTA connections. Each SUB bioprocess container had connections for two gas outlet filters, one pressure sensor filter, one filter for headspace aeration and filter each for micro and macro spargers.

The pressure filter was connected to the pressure sensor and the gas inlet and outlet filters were open before inflation was started.

The sparger and head space gas filters were connected to the controller of the present disclosure using silicon tubing, which in turn was connected to the main gas supplies via nylon tubing. The main gas supply pressures were set to 1.8 barg for all gases. The MFCs had a turn down ratio of 1:50 and range of up to 100 L/min. As a result an additional calibrated rotameter was required supply of the $CO_2$ ballast because this flow rate was too low to control with the MFC.

For safety reasons it was important to ensure that gas outlet line and pressure sensor line were not kinked during inflation.

Inflation of the SUB bioprocess container was started slowly with a low gas flow rate. A scientist had to hold the SUB bioprocess container in place until the agitator shaft 8 and motor were magnetically coupled. To prevent damage to the SUB bioprocess container it had to be inflated such that no components inside the bioprocess container (agitator blades or dip tubes) touched the bioprocess container. Inflation had to be stopped once it was possible to couple the agitator and the motor.

The agitator magnetic coupling was then slowly lifted up to the motor. Once in place the SUB bioprocess container was rotated slowly into position to align the probe ports with the probe holders and to align the seal of the SUB bioprocess container with the middle of where the two doors met. When in final position the agitator shaft 8 was secured in place to the motor using a tri clamp. The filters were fitted into position on the filter holder. A vent heater was placed around the gas outlet filter. The SUB bioprocess container was then fully inflated. A continuous air flow (at the air cap described in the pilot fermentation process description (FPD)) was maintained through the sparger and headspace in order to keep the SUB bioprocess container inflated.

One standard pH and one standard DOT probe were calibrated prior to starting each batch using the standard calibration procedure used the Slough pilot plant. These probes were fitted into the probe sleeves with connections and autoclaved on a fluid cycle. The probes were fitted into the SUB bioprocess container using the connections and placed onto the probe holder shelf set at a 15° degree angle to the horizontal.

Once pH and DOT probes were fitted the medium or buffer as appropriate was filtered into the SUB bioprocess container using a pre irradiated 0.1 μm filter welded on onto the dip tube. The Bioprocess container holders tested did not have a load cell, so a floor balance was used to weigh in the medium/buffer. During medium fill/buffer fill a constant air flow (at the air cap described in the pilot FPD) was maintained to avoid liquid going into the gas inlet line.

Once the required volume was achieved the jacket was filled with DI water and temperature and agitation control was initiated. Following medium fill pH control was initiated based on the reusable probe using $CO_2$ to prevent the pH from drifting outside the acceptable range for medium hold. The disposable pH and DOT probes were then activated. The pH and DOT probes were left to equilibrate overnight in the medium or buffer.

Sample bioprocess containers were welded onto the sample line situated next to the disposable pH and DOT probes in order to ensure the sample was representative of the environment experience by the probes. Samples were removed the day after the vessel was filled and analyzed for pH and $pCO_2$. The results from these measurements were used to perform single point calibrations on the DOT and pH probes.

For inoculation an S200 cell bioprocess container was connected to the SUB bioprocess container using sterile c flex tubing attached to the dip tube line. The required volume of inoculum was pumped to the SUB bioprocess container using a calibrated Watson Marlow 600 series pump.

The feeds, alkali and antifoam were all welded onto the SUB bioprocess container using c flex tubing, each had dedicated lines. Alkali addition was via the Watson Marlow 100 series alkali pump built into the control tower. Alkali was added as required to control the pH. Antifoam was added manually using the second Watson Marlow 100 series pump built into the control tower.

Feeds were added using Watson Marlow 500 series pumps. Flow rates and addition volumes were determined using appropriately sized balances correcting for the density of the feeds. The flow rate of the continuous feeds SF70 and 400 g/L D glucose were adjusted on a daily basis according to the viable cell concentration (VCC) and glucose concentration of the culture. Shot feeds SF71, SF72 and SF73 were added according to the FPD.

Each day samples were taken as part of daily monitoring of the bioreactors to check cell concentrations, viabilities, metabolites and dissolved gases using sample bioprocess containers attached to the sample line.

One point adjustments for online pH probes were performed when necessary according to UKSL 182 using results from a calibrated offline pH probe (Mettle Toledo offline 405 DPAS SC K8S/120 with pHM220 meter).

Example 4

Use of a Single Use Bioreactor in a Production System

In another example, this single-use bioreactor can also be used in the systems and methods disclosed in WO 2017/072201 A2, the entirety of which is incorporated by reference.

In WO 2017/072201 A2, bioreactors are used during both the inoculum expansion and production process steps. The single-use bioreactors of the present disclosure provide advantages to this system because they can be made ready for different runs more quickly and efficiently, thereby reducing bioreactor "down time" needed for cleaning and sterilizing.

This will allow the systems of WO 2017/072201 A2 to produce high quality, safe, and cost effective active pharmaceutical ingredients (APIs) and biopharmaceutical products in a more timely and cost-effective manner. For instance, there would be greater flexibility in vessel architecture and components used when designing processes to manufacture proteins and cells, significantly reduced operating costs (e.g., labor, utility, and maintenance), improved facility throughput as batch turnaround times are condensed, clean in place and steam in place operations.

As part of the process disclosed in WO 2017/072201 A2, there are purification steps. During the purification processes, numerous resins can be used during purification, including but not limited to, MabSelect SuRe/MabSelect SuRe LX/MabSelect SuRe pcc (GE Healthcare), Amsphere A and Amsphere A3 (JSR micro), Praesto AP and Praesto AC (Purolite), KanCapA (Pall), Toyopearl AF-rProtein A HC (Tosoh), Poros MabCapture A (Thermo-Fisher), and the like. Other purification material would be known to a person of ordinary skill in the art and this is by no means an exhaustive list.

It should be recognized that the one or more examples in the disclosure are non-limiting examples and that the present disclosure is intended to encompass variations and equivalents of these examples.

The invention claimed is:

1. A bioreactor comprising: a bioprocess container made from a liquid impermeable and flexible shape-conforming material, the bioprocess container having a bottom and at least one side wall, the bioprocess container defining a hollow enclosure for receiving a culture media, the bioprocess container including an interior surface configured to contact a culture media contained in the hollow enclosure and an opposite exterior surface, wherein the flexible shape-conforming material comprises a polymer film, the hollow enclosure having a volume of from about 2 L to about 50,000 L; a rigid shell defining an interior volume and having a shape configured to receive the bioprocess container therein, the rigid she having a bottom portion defining an interior surface, the bioprocess container conforming to the interior surface of the bottom portion of the rigid shell; a mixing device comprising a rotatable shaft coupled to at least one impeller that extends into the hollow enclosure of the bioprocess container; a drain line in fluid communication with the bioprocess container, the drain line being located at the bottom of the bioprocess container; a fluid collecting device positioned between the hollow enclosure of the bioprocess container and the drain line, the fluid collecting device having a shape configured to induce a vortex flow of fluids from the bioprocess container into the drain line; and a vortex breaker for avoiding air entrapment during draining, the vortex breaker being located adjacent the bottom portion of the rigid shell and being separate from the fluid collecting device and the mixing device, and wherein the vortex breaker is located below the bottom portion of the rigid shell.

2. A bioreactor as defined in claim 1, wherein the hollow enclosure of the bioprocess container has a volume and wherein the drain line has a cross-sectional area and wherein the cross-sectional area of the drain line is proportional to the volume of the hollow enclosure, the drain line having a cross-sectional area of from about 0.3 mm$^2$ to about 0.7 mm$^2$ per liter of volume of the hollow enclosure.

3. A bioreactor as defined in claim 1, wherein the bottom of the bioprocess container has a dome-shape for facilitating drainage.

4. A bioreactor as defined in claim 1, wherein the rigid shell includes a dished bottom.

5. A bioreactor as defined in claim 4, wherein the dished bottom of the rigid shell is circular, dished and flanged.

6. A bioreactor as defined in claim 1, wherein the drain line is positioned at a bottom central region of the bioprocess container, the drain line being positioned also at a center of a lowest point on the bioprocess container.

7. A bioreactor as defined in claim 1, wherein the impeller to bioprocess container diameter ratio is from about 0.35 to about 0.55.

8. A bioreactor as defined in claim 1, wherein the bioreactor includes a top impeller and a bottom impeller and wherein the flow number ($N_q$) of the top impeller and the bottom impeller is from about 0.4 to about 0.9.

9. A bioreactor as defined in claim 1, further comprising at least one baffle being configured to extend adjacent to the side wall of the bioprocess container in a longitudinal direction, the baffle having a shape that extends radially inward from the side wall an amount sufficient to affect fluid flow in the hollow enclosure during mixing of a culture media by the mixing device, the baffle being positioned between the interior surface of the rigid shell and the exterior surface of the bioprocess container.

10. A bioreactor as defined in claim 1, wherein the bioreactor further comprises at least one sparger and wherein the sparger comprises a ballast sparger, the ballast sparger comprising a gas tube that has a longitudinal portion and a lateral portion, the longitudinal portion extending vertically into the hollow enclosure of the bioprocess container, the lateral portion being located at an end of the longitudinal portion below the impeller, the lateral portion defining a plurality of holes for releasing a gas into a culture media contained within the bioprocess container.

11. A bioreactor as defined in claim 1, further comprising a controller in communication with at least one sensor, the controller being configured to receive information from the at least one sensor and, based on the information, to control a fluid supply for varying a flow rate of a fluid from the fluid supply into the hollow enclosure of the bioprocess container for maintaining at least one parameter of a culture media contained within the hollow enclosure within preset limits.

12. A bioreactor as defined in claim 11, wherein the fluid supply comprises a carbon dioxide gas supply in fluid communication with the bioprocess container and a liquid alkali supply also in fluid communication with the bioprocess container, the at least one sensor comprising a pH sensor and wherein the controller is configured to regulate pH levels of a culture media within preset limits by adding amounts of carbon dioxide gas from the carbon dioxide gas supply for selectively lowering the pH or by adding amounts of an alkali from the liquid alkali supply for selectively increasing the pH.

13. A bioreactor as defined in claim 11, wherein the fluid supply comprises an oxygen gas supply and wherein the at least one sensor comprises a dissolved oxygen sensor and wherein the controller regulates dissolved oxygen levels within a culture media within present limits by periodically adding amounts of oxygen gas from the oxygen gas supply to a culture media within the hollow enclosure of the bioprocess container based on information received from the dissolved oxygen sensor.

14. A bioreactor as defined in claim 11, wherein the fluid supply comprises a carbon dioxide gas supply and wherein the at least one sensor comprises a dissolved carbon dioxide sensor and wherein the controller regulates dissolved carbon dioxide levels within a culture media within present limits by periodically adding amounts of carbon dioxide gas from the carbon dioxide gas supply to a culture media within the hollow enclosure of the bioprocess container based on information received from the dissolved carbon dioxide sensor.

15. A bioreactor as defined in claim 11, further comprising a thermal jacket surrounding the bioprocess container, the thermal jacket being in fluid communication with at least one of a heated fluid or a chilled fluid, the bioreactor further comprising a temperature sensor for sensing a temperature of a culture media contained within the bioprocess container, the temperature sensor being in communication with the controller, and wherein the controller is configured to receive information from the temperature sensor and, based on the information, control flow of a fluid into the thermal jacket for increasing or decreasing the temperature of a culture media contained in the bioprocess container for maintaining a culture media within preset temperature limits.

16. A bioreactor as defined in claim 11, wherein the at least one sensor comprises a pH sensor and a dissolved oxygen sensor that are both in communication with the controller and wherein the controller receives information from the pH sensor and the dissolved oxygen sensor and controls a flow of different fluids into the bioprocess container for maintaining pH levels and dissolved oxygen levels of a culture media contained within the bioprocess container within preset limits.

17. A bioreactor as defined in claim 1, further comprising at least one feed line that extends into the hollow enclosure for feeding fluids into the bioprocess container, the feed line including a subsurface fluid outlet positioned adjacent the agitator, the fluid outlet being associated with a fluid control device that only permits fluid to flow out of the fluid outlet and prevents fluid flow in an opposite direction.

18. A bioreactor as defined in claim 1, further comprising at least one feed line positioned at a top of the bioprocess container, the feed line including a supersurface fluid discharge positioned above a volume of culture media residing in the bioprocess container, the supersurface fluid discharge being located such that a fluid flowing through the fluid discharge makes direct contact with a culture media contained within the bioprocess container.

19. A bioreactor as defined in claim 18, wherein a top impeller forms a circumference when rotated and wherein the supersurface fluid discharge of the feed line is positioned above the circumference of the top impeller such that fluids flowing through the fluid discharge contact a culture media within the circumference.

20. A bioreactor as defined in claim 1, wherein the interior surface of the polymer film comprises a modified polyolefin.

21. A bioreactor comprising: a bioprocess container made from a liquid impermeable and flexible shape-conforming material, the bioprocess container having a bottom and at least one side wall, the bioprocess container defining a hollow enclosure for receiving a culture media, the bioprocess container including an interior surface configured to contact a culture media contained in the hollow enclosure and an opposite exterior surface, wherein the flexible shape-conforming material comprises a polymer film, the hollow enclosure having a volume of from about 2 L to about 50,000 L; a rigid shell defining an interior volume and having a shape configured to receive the bioprocess container therein, the rigid shell having a bottom portion defining an interior surface, the bioprocess container conforming to the interior surface of the bottom portion of the rigid shell; a mixing device comprising a rotatable shaft coupled to at least one impeller that extends into the hollow enclosure of the bioprocess container; a drain line in fluid communication with the bioprocess container, the drain line being located at the bottom of the bioprocess container, and wherein the hollow enclosure of the bioprocess container has a volume and wherein the drain line has a cross-sectional area and wherein the cross-sectional area of the drain line is proportional to the volume of the hollow enclosure, the drain line having a cross-sectional area of from about 0.3 mm$^2$ to about 0.7 mm$^2$ per later of volume of the hollow enclosure; and a vortex breaker for avoiding air entrapment during draining, the vortex breaker being located adjacent the bottom portion of the rigid shell and being separate from the mixing device, and wherein the vortex breaker is located below the bottom portion of the rigid shell.

* * * * *